US011773336B2

United States Patent
Bao et al.

(10) Patent No.: US 11,773,336 B2
(45) Date of Patent: Oct. 3, 2023

(54) PROCESSES AND SYSTEMS FOR UPGRADING ALKANES AND ALKYL AROMATIC HYDROCARBONS

(71) Applicant: ExxonMobil Chemical Patents Inc., Baytown, TX (US)

(72) Inventors: Xiaoying Bao, Houston, TX (US); James R. Lattner, La Porte, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/745,433

(22) Filed: May 16, 2022

(65) Prior Publication Data
US 2022/0275289 A1 Sep. 1, 2022

Related U.S. Application Data

(63) Continuation-in-part of application No. PCT/US2021/026639, filed on Apr. 9, 2021.
(Continued)

(30) Foreign Application Priority Data

Jun. 11, 2020 (EP) .................................... 20179510

(51) Int. Cl.
*C10G 29/04* (2006.01)
*C10G 25/00* (2006.01)
*C10G 31/06* (2006.01)

(52) U.S. Cl.
CPC ........... *C10G 29/04* (2013.01); *C10G 25/003* (2013.01); *C10G 31/06* (2013.01)

(58) Field of Classification Search
CPC ...... C10G 25/003; C10G 29/04; C10G 31/06; B01J 21/04; B01J 21/10; B01J 23/626;
(Continued)

(56) References Cited

U.S. PATENT DOCUMENTS 3,888,762 A   6/1975   Gerhold .................. 208/120
4,502,947 A   3/1985   Haddad et al. ........... 208/161
(Continued)

FOREIGN PATENT DOCUMENTS

EP            0098622        3/1986   ............. B01J 23/62
WO     WO2001/085872       11/2001   ............. C10G 11/18
(Continued)

OTHER PUBLICATIONS

DeWilde, J. (2014) "Gas-Solid Fluidized Beds in Vortex Chambers," *Chem. Engin. Processing: Process Intensification*, v.85, pp. 256-290.
(Continued)

*Primary Examiner* — Brian A Mccaig

(57) ABSTRACT

Processes for upgrading a hydrocarbon. In some embodiments, the process can include contacting a hydrocarbon-containing feed with a first catalyst that can include a Group 8-10 element disposed on a support within a first conversion zone to effect dehydrogenation, dehydroaromatization, and/or dehydrocyclization of a portion of the feed to produce first conversion zone effluent that includes one or more upgraded hydrocarbons, molecular hydrogen, and unconverted feed. The process can also include contacting the first conversion zone effluent with a second catalyst that can include a Group 8-10 element disposed on a support within a second conversion zone to effect dehydrogenation, dehydroaromatization, and/or dehydrocyclization of at least a portion of the unconverted feed to produce a second conversion zone effluent that includes an additional quantity of upgraded hydrocarbon(s) and molecular hydrogen. A temperature of the second conversion zone effluent can be greater than a temperature of the first conversion zone effluent.

26 Claims, 3 Drawing Sheets

Related U.S. Application Data

(60) Provisional application No. 63/022,034, filed on May 8, 2020.

(58) Field of Classification Search
CPC ... B01J 37/088; B01J 37/0201; C07C 5/3337; C07C 2521/04; C07C 2521/10; C07C 2523/14; C07C 2523/42; C07C 2523/62; Y02P 20/52
See application file for complete search history.

(56) References Cited

U.S. PATENT DOCUMENTS

| | | | | |
|---|---|---|---|---|
| 4,788,371 | A | 11/1988 | Imai et al. | 585/443 |
| 4,962,265 | A | 10/1990 | De Clippeleir et al. | 585/660 |
| 4,985,136 | A | 1/1991 | Bartholic | 208/153 |
| 5,248,411 | A | 9/1993 | Chan | 208/161 |
| 5,321,192 | A | 6/1994 | Cottrell | 585/659 |
| 5,922,925 | A | 7/1999 | Akporiaye et al. | 585/660 |
| 7,038,098 | B2 * | 5/2006 | Walsdorff | C07C 5/327 585/440 |
| 7,102,050 | B1 | 9/2006 | Lattner et al. | 585/640 |
| 7,122,160 | B2 | 10/2006 | Brookhart | 422/145 |
| 7,195,741 | B2 | 3/2007 | Lattner et al. | 422/141 |
| 8,653,317 | B2 | 2/2014 | Pierce et al. | 585/659 |
| 2004/0082824 | A1 | 4/2004 | Lattner | 585/638 |
| 2008/0194891 | A1 | 8/2008 | Pretz et al. | 585/252 |
| 2017/0088487 | A1 | 3/2017 | Buchanan et al. | C07C 2/76 |
| 2021/0276002 | A1 | 9/2021 | Bao et al. | B01J 38/32 |
| 2021/0276932 | A1 | 9/2021 | Bao | C07C 5/3337 |
| 2022/0274901 | A1 | 9/2022 | Bao et al. | C07C 5/3337 |
| 2022/0282165 | A1 | 9/2022 | Bao | C10G 29/04 |

FOREIGN PATENT DOCUMENTS

| | | | |
|---|---|---|---|
| WO | WO2004/029178 | 4/2004 | C10G 3/00 |
| WO | WO2005/077867 | 8/2005 | C07C 5/00 |
| WO | WO2014/081545 | 5/2014 | C07C 5/333 |
| WO | WO2016/140574 | 9/2016 | C07C 5/333 |

OTHER PUBLICATIONS

Gent, R. (1968) "Thermal Cracking of Propane," *Kinetics and Product Distributions*, v.7(3), pp. 435-447.

Reichle, W. T. (1985) "Catalytic Reactions by Thermally Activated, Synthetic, Anionic Clay Minerals," *Journal of Catlysis*, v.94(2), p. 547-557.

Schaper, H. et al. (1989) "Stabilized Magnesia: A Novel Catalyst (Support) Material," *Applied Catalysis*, v. 54(1), pp. 79-90.

Teleki, A. et al. (2008) "Distinguishing Between Aggregates and Agglomerates of Flame-Made $TiO_2$ by High-Pressure Dispersion," *Powder Tech.*, v.181(3), pp. 292-300.

VanDamme, P. S. (1975) "Thermal Cracking of Propane and Propane-Propylene Mixtures: Pilot Plant Versus Industrial Data," *AIChE Jrnl.*, v.21(6), pp. 1065-1073.

* cited by examiner

US 11,773,336 B2

PROCESSES AND SYSTEMS FOR UPGRADING ALKANES AND ALKYL AROMATIC HYDROCARBONS

CROSS-REFERENCE TO RELATED APPLICATIONS

This application is a continuation-in-part of International Application No. PCT/US2021/026639, filed on Apr. 9, 2021, and published as WO2021/225747, which claims priority to and the benefit of U.S. Provisional Application No. 63/022,034, filed on May 8, 2020, and European Patent Application No. 20179510.1, filed on Jun. 11, 2020, which are all incorporated herein by reference in their entirety.

FIELD

This disclosure relates to processes and systems for upgrading alkanes and/or alkyl aromatic hydrocarbons. More particularly, this disclosure relates to multistage processes and systems for dehydrogenating, dehydroaromatizing, and/or dehydrocyclizing one or more alkanes and/or one or more alkyl aromatic hydrocarbons in the presence of at least a first catalyst to produce a first effluent and a second catalyst to produce a second effluent that includes one or more upgraded hydrocarbons and molecular hydrogen.

BACKGROUND

Catalytic dehydrogenation, dehydroaromatization, and dehydrocyclization of alkanes and/or alkyl aromatic hydrocarbons are industrially important chemical conversion processes that are endothermic and equilibrium-limited. The dehydrogenation of alkanes, e.g., $C_2$-$C_{16}$ alkanes, and/or alkyl aromatic hydrocarbons, e.g., ethylbenzene, can be done through a variety of different supported catalyst particle systems such as the Pt-based, Cr-based, Ga-based, V-based, Zr-based, In-based, W-based, Mo-based, Zn-based, and Fe-based systems. Among the existing propane dehydrogenation processes, a certain process uses an alumina supported chromia catalyst that provides one of the highest propylene yields at approximately 50% (55% propane conversion at 90% propylene selectivity), which is obtained at a temperature of approximately 560° C. to 650° C. and at a low pressure of 20 kPa-absolute to 50 kPa-absolute. It is desirable to increase the propylene yield without having to operate at such low pressure to increase the efficiency of the dehydrogenation process.

Increasing the temperature of the dehydrogenation process is one way to increase the conversion of the process according to the thermodynamics of the process. For example, at 670° C., 100 kPa-absolute, in the absence of any inert/diluent, the equilibrium propylene yield has been estimated via simulation to be approximately 74%. At such high temperature, however, the catalyst particles deactivate very rapidly and/or the propylene selectivity becomes uneconomically low. The rapid deactivation of the catalyst particles is believed to be caused by coke depositing onto the catalyst particles and/or agglomeration of the active phase. Coke can be removed by combustion using an oxygen-containing gas, however, agglomeration of the active phase is believed to be exacerbated during the combustion process, which rapidly reduces the activity and stability of the catalyst particles.

There is a need, therefore, for improved processes and systems for dehydrogenating, dehydroaromatizing, and/or dehydrocyclizing alkanes and/or alkyl aromatic hydrocarbons. This disclosure satisfies this and other needs.

SUMMARY

Multi-stage processes and systems for upgrading alkanes and/or alkyl aromatic hydrocarbons are provided. In some embodiments, the multi-stage hydrocarbon upgrading process can include (I) contacting a hydrocarbon-containing feed with a first catalyst that can include a Group 8-10 element disposed on a support within a first conversion zone to effect one or more of dehydrogenation, dehydroaromatization, and dehydrocyclization of a portion of the hydrocarbon-containing feed to produce a first conversion zone effluent that can include one or more upgraded hydrocarbons, molecular hydrogen, and unconverted hydrocarbon-containing feed. The process can also include (II) contacting the first conversion zone effluent with a second catalyst that can include a Group 8-10 element disposed on a support within a second conversion zone to effect one or more of dehydrogenation, dehydroaromatization, and dehydrocyclization of at least a portion of the unconverted hydrocarbon-containing feed to produce a second conversion zone effluent that can include an additional quantity of one or more upgraded hydrocarbons and molecular hydrogen. The hydrocarbon-containing feed can include one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof. The hydrocarbon-containing feed and the first catalyst can be contacted for a time period in a range from 0.1 seconds to 3 hours, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatic hydrocarbons in the hydrocarbon-containing feed. The first conversion zone effluent and the second catalyst can be contacted for a time period in a range from 0.1 seconds to 3 hours, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatic hydrocarbons in the first conversion zone effluent. The first conversion zone effluent can have a temperature in a range from 300° C. to 850° C. The second conversion zone effluent can have a temperature in a range from 350° C. to 900° C. A temperature of the second conversion zone effluent can be greater than a temperature of the first conversion zone effluent. The first catalyst and the second catalyst can have the same composition or a different composition. The first catalyst and the second catalyst each include from 0.001 wt % to 6 wt % of the Group 8-10 element based on the weight of the support. The support can include at least one of: w wt % of one or more Group 2 elements, x wt % of one or more Group 4 elements, y wt % of one or more Group 12 elements, and z wt % of one or more elements having an atomic number of 21, 39, or 57-71, based on the weight of the support, where w, x, y, and z are independently in a range from 0 to 100, where w+x+y+z is ≤100, and where any Group 2 element present is associated with a wt % m based on the weight of the support, any Group 4 element present is associated with a wt % n based on the weight of the support, any group 12 element present is associated with a wt % p based on the weight of the support, and any element having an atomic number of 21, 39, or 57-71 present is associated with a wt % q based on the weight of the support, m, n, p, and q are each equal to 1, 2, 15, or 30, or m=1, n=15, p=15, and q=1, and a sum of w/m+x/n+y/p+z/q is ≥1, based on the weight of the support.

The one or more upgraded hydrocarbons can include a dehydrogenated hydrocarbon, a dehydroaromatized hydrocarbon, a dehydrocyclized hydrocarbon, or a mixture thereof.

In other embodiments, the multi-stage hydrocarbon upgrading process can include (I) contacting a hydrocarbon-containing feed with a first plurality of fluidized catalyst particles that can include a Group 8-10 element disposed on a support within a first conversion zone to effect one or more of dehydrogenation, dehydroaromatization, and dehydrocyclization of a first portion of the hydrocarbon-containing feed to produce a first conversion zone effluent that can include coked first catalyst particles, one or more upgraded hydrocarbons, molecular hydrogen, and unconverted hydrocarbon-containing feed. The process can also include (II) contacting the first conversion zone effluent with a second plurality of fluidized catalyst particles that can include a Group 8-10 element disposed on a support within a second conversion zone to effect one or more of dehydrogenation, dehydroaromatization, and dehydrocyclization of at least a portion of the unconverted hydrocarbon-containing feed to produce a second conversion zone effluent that can include coked second catalyst particles, an additional quantity of upgraded hydrocarbons, and an additional quantity of molecular hydrogen. The hydrocarbon-containing feed can include one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof. The hydrocarbon-containing feed and the first plurality of fluidized catalyst particles can be contacted for a time period in a range from 0.1 seconds to 2 minutes, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatic hydrocarbons in the hydrocarbon-containing feed. The first conversion zone effluent and the second plurality of fluidized catalyst particles can be contacted for a time period in a range from 0.1 seconds to 2 minutes, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatic hydrocarbons in the first conversion zone effluent. The first conversion zone effluent can have a temperature in a range from 300° C. to 850° C. The second conversion zone effluent can have a temperature in a range from 350° C. to 900° C. A temperature of the second conversion zone effluent can be greater than a temperature of the first conversion zone effluent. The one or more upgraded hydrocarbons can include a dehydrogenated hydrocarbon, a dehydroaromatized hydrocarbon, a dehydrocyclized hydrocarbon, or a mixture thereof. The process can also include (III) obtaining from the second conversion zone effluent a first gaseous stream rich in the upgraded hydrocarbons and molecular hydrogen and a first particle stream rich in the coked first catalyst particles and the coked second catalyst particles. The process can also include (IV) splitting the first particle stream into a second particle stream and a third particle stream. The process can also include (V) recycling the second particle stream to the first conversion zone as the first plurality of fluidized particles. The process can also include (VI) contacting the third particle stream with an oxidant in a combustion zone to effect combustion of at least a portion of the coke to produce a combustion effluent that can include regenerated catalyst particles lean in coke and a combustion gas. The process can also include (VII) obtaining from the combustion effluent a second gaseous stream rich in the combustion gas and a fourth particle stream rich in the regenerated catalyst particles. The process can also include (VIII) recycling the fourth particle stream to the second conversion zone as the second plurality of fluidized catalyst particles.

In some embodiment, the multistage hydrocarbon upgrading system, can include a first conversion zone that can be adapted for contacting a hydrocarbon-containing feed with a first plurality of fluidized catalyst particles to effect one or more of dehydrogenation, dehydroaromatization, and dehydrocyclization of a first portion of the hydrocarbon-containing feed to produce a first conversion zone effluent that can include coked first catalyst particles, one or more upgraded hydrocarbons, molecular hydrogen, and unconverted hydrocarbon-containing feed. The system can also include a second conversion zone that can be adapted for contacting the first conversion zone effluent with a second plurality of fluidized catalyst particles to effect one or more of dehydrogenation, dehydroaromatization, and dehydrocyclization of at least a portion of the unconverted hydrocarbon-containing feed to produce a second conversion zone effluent that can include coked second catalyst particles, an additional quantity of upgraded hydrocarbons, and an additional quantity of molecular hydrogen. The system can also include a first separator that can be adapted for separating the second conversion zone effluent into a first gaseous stream rich in the upgraded hydrocarbons and the molecular hydrogen and a first particle stream rich in the coked first catalyst particles and the coked second catalyst particles. The system can also include a second separator that can be adapted for separating the first particle stream into a second particle stream that can include a first portion of the first particle stream and a third particle stream that can include a second portion of the first particle stream. The system can also include a first channel that can be adapted for feeding at least a portion of the second particle stream into the first conversion zone as the first plurality of fluidized catalyst particles. The system can also include a second channel that can be adapted for feeding at least a portion of the third particle stream into a combustion zone. The combustion zone can be adapted for contacting the third particle stream and an oxidant to effect combustion of at least a portion of the coke to produce a combustion effluent that can include regenerated catalyst particles lean in coke and a combustion gas. The system can also include a third separator that can be adapted for separating the combustion effluent into a second gaseous stream rich in the combustion gas and a fourth particle stream rich in the regenerated catalyst particles. The system can also include a third channel that can be adapted for feeding at least a portion of the fourth particle stream into the second conversion zone as the second plurality of fluidized catalyst particles.

DETAILED DESCRIPTION

Figure 1:
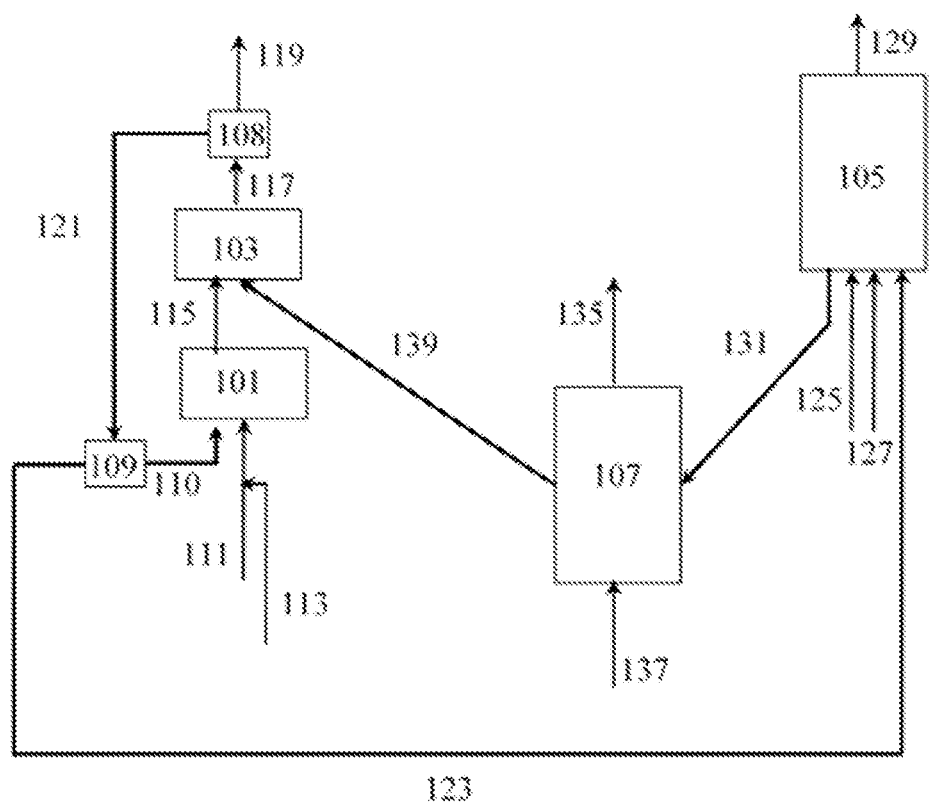
FIG. 1 depicts an illustrative system for upgrading a hydrocarbon-containing feed that includes a first reactor, a second reactor, a regenerator, and a reduction reactor, according to one or more embodiments described.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In this disclosure, a process is described as comprising at least one "step." It should be understood that each step is an action or operation that may be carried out once or multiple times in the process, in a continuous or discontinuous fashion. Unless specified to the contrary or the context clearly indicates otherwise, multiple steps in a process may be conducted sequentially in the order as they are listed, with or without overlapping with one or more other steps, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in this disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contains a certain level of error due to the limitation of the technique and/or equipment used for acquiring the measurement.

Certain embodiments and features are described herein using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated.

The indefinite article "a" or "an", as used herein, means "at least one" unless specified to the contrary or the context clearly indicates otherwise. Thus, embodiments using "a reactor" or "a conversion zone" include embodiments where one, two or more reactors or conversion zones are used, unless specified to the contrary or the context clearly indicates that only one reactor or conversion zone is used.

The terms "up" and "down"; "upward" and "downward"; "upper" and "lower"; "upwardly" and "downwardly"; "above" and "below"; and other like terms used herein refer to relative positions to one another and are not intended to denote a particular spatial orientation since the apparatus and methods of using the same may be equally effective at various angles or orientations.

The term "hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). Thus, a $C_2$ hydrocarbon can be ethane, ethylene, acetylene, or mixtures of at least two of these compounds at any proportion. A "Cm to Cn hydrocarbon" or "Cm-Cn hydrocarbon," where m and n are positive integers and m<n, means any of Cm, Cm+1, Cm+2, . . . , Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cn+ hydrocarbon" means (i) any hydrocarbon compound comprising carbon atom(s) in its molecule at the total number of at least n, or (ii) any mixture of two or more such hydrocarbon compounds in (i). A "Cn− hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s).

For the purposes of this disclosure, the nomenclature of elements is pursuant to the version of the Periodic Table of Elements (under the new notation) as provided in Hawley's Condensed Chemical Dictionary, 16$^{th}$ Ed., John Wiley & Sons, Inc., (2016), Appendix V. For example, a Group 8 element includes Fe, a Group 9 element includes Co, and a group 10 element includes Ni. The term "metalloid", as used herein, refers to the following elements: B, Si, Ge, As, Sb, Te, and At. In this disclosure, when a given element is indicated as present, it can be present in the elemental state or as any chemical compound thereof, unless it is specified otherwise or clearly indicated otherwise by the context.

The term "alkane" means a saturated hydrocarbon. The term "cyclic alkane" means a saturated hydrocarbon comprising a cyclic carbon ring in the molecular structure thereof. An alkane can be linear, branched, or cyclic.

The term "aromatic" is to be understood in accordance with its art-recognized scope, which includes alkyl substituted and unsubstituted mono- and polynuclear compounds.

The term "rich" when used in phrases such as "X-rich" or "rich in X" means, with respect to an outgoing stream obtained from a device, e.g., a conversion zone, that the stream comprises material X at a concentration higher than in the feed material fed to the same device from which the stream is derived. The term "lean" when used in phrases such as "X-lean" or "lean in X" means, with respect to an outgoing stream obtained from a device, e.g., a conversion zone, that the stream comprises material X at a concentration lower than in the feed material fed to the same device from which the stream is derived.

The term "mixed metal oxide" refers to a composition that includes oxygen atoms and at least two different metal atoms that are mixed on an atomic scale. For example, a "mixed Mg/Al metal oxide" has O, Mg, and Al atoms mixed on an atomic scale and is substantially the same as or identical to a composition obtained by calcining an Mg/Al hydrotalcite that has the general chemical formula

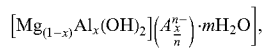

where A is a counter anion of a negative charge n, x is in a range of from >0 to <1, and m is ≥0. A material consisting of nm sized MgO particles and nm sized $Al_2O_3$ particles mixed together is not a mixed metal oxide because the Mg and Al atoms are not mixed on an atomic scale but are instead mixed on a nm scale.

The term "selectivity" refers to the production (on a carbon mole basis) of a specified compound in a catalytic reaction. As an example, the phrase "an alkane hydrocarbon conversion reaction has a 100% selectivity for an olefin hydrocarbon" means that 100% of the alkane hydrocarbon (carbon mole basis) that is converted in the reaction is converted to the olefin hydrocarbon. When used in connection with a specified reactant, the term "conversion" means the amount of the reactant consumed in the reaction. For example, when the specified reactant is propane, 100% conversion means 100% of the propane is consumed in the reaction. Yield (carbon mole basis) is conversion times selectivity. In another example, when the specified reactant is propane, if one mole of propane converts to one mole of methane and one mole of ethylene, the selectivity to methane is 33.3% and the selectivity to ethylene is 66.7%.

The terms "first conversion zone effluent", "second conversion zone effluent", and "intermediate conversion zone effluents", collectively "conversion zone effluents", refer to fluid components, i.e., gas and/or liquid components, and exclude solid components that can be present, e.g., fluidized catalyst particles, in the conversion zone effluents. As such, when the temperatures of the conversion zone effluents are discussed, the temperatures refer to the temperatures of the fluid components, i.e., gas and/or liquid components, and not to the temperature of any solid components.

The term "substantially adiabatic", when used to describe the first conversion zone, the second conversion zone, and the optional one or more intermediate conversion zones, means the conversion zone is adiabatic except for unavoidable heat losses to the environment.

Overview

The hydrocarbon-containing feed can be or can include, but is not limited to, one or more alkanes, e.g., $C_2$-$C_{16}$ linear or branched alkanes and/or $C_4$-$C_{16}$ cyclic alkanes, and/or one or more alkyl aromatic hydrocarbons, e.g., $C_8$-$C_{16}$ alkyl aromatic hydrocarbons. In some embodiments, the hydrocarbon-containing feed can optionally include 0.1 vol % to 50 vol % of steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include <0.1 vol % of steam or can be free of steam, based on the total volume of any $C_2$-$C_{16}$ alkanes and any $C_8$-$C_{16}$ alkyl aromatic hydrocarbons in the hydrocarbon-containing feed.

In some embodiments, the hydrocarbon-containing feed can be contacted with a first catalyst that includes one or more Group 8-10 elements, e.g., Pt, disposed on a support within a first conversion zone to effect one or more of dehydrogenation, dehydroaromatization, and dehydrocyclization of a portion of the hydrocarbon-containing feed to produce a first conversion zone effluent that can include one or more upgraded hydrocarbons, molecular hydrogen, and unconverted hydrocarbon-containing feed. The one or more upgraded hydrocarbons can be or can include one or more dehydrogenated hydrocarbons, one or more dehydroaromatized hydrocarbons, one or more dehydrocyclized hydrocarbons, or a mixture thereof. The hydrocarbon-containing feed and the first catalyst can be contacted for a time period in a range from 0.1 seconds to 3 hours, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatic hydrocarbons in the hydrocarbon-containing feed. The first conversion zone effluent can have a temperature in a range from 300° C. to 850° C.

The first conversion zone effluent can be contacted with a second catalyst that includes one or more Group 8-10 elements, e.g., Pt, disposed on a support within a second conversion zone to effect one or more of dehydrogenation, dehydroaromatization, and dehydrocyclization of at least a portion of the unconverted hydrocarbon-containing feed to produce a second conversion zone effluent that can include an additional quantity of one or more upgraded hydrocarbons and molecular hydrogen. It should be understood that the Group 8-10 element in the first catalyst and the Group 8-10 element in the second catalyst can be the same or different. The first conversion zone effluent and the second catalyst can be contacted for a time period in a range from 0.1 seconds to 3 hours, under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatic hydrocarbons in the first conversion zone effluent. The second conversion zone effluent can have a temperature in a range from 350° C. to 900° C.

For fixed bed reactors, it should be recognized that the temperature of an effluent recovered from a given conversion zone is dependent, at least in part, on the heat of reaction, the temperature/flow rate/heat capacity of the feed fed into a given conversion zone, and the temperature/mass/heat capacity (for non-steady processes) of the catalyst in a given conversion zone before contacting the feed. For fluidized bed reactors, it should be recognized that the temperature of a given conversion zone effluent is dependent, at least in part, on the heat of reaction, the temperature/flow rate/heat capacity of the feed fed into a given conversion zone, and the temperature/mass flow rate/heat capacity of the catalyst feed introduced into a given conversion zone. Therefore, in some embodiments, the first conversion zone effluent can be contacted with the second catalyst at a temperature that can be greater than a temperature of the first catalyst when the hydrocarbon-containing feed contacts the first catalyst. As such, the temperature of the second conversion zone effluent can be greater than a temperature of the first conversion zone effluent. For example, the temperature of the second conversion zone effluent can be 30° C., 40° C., 50° C., 60° C., 70° C., or 80° C. to 90° C., 100° C., 110° C., 120° C., 150° C., or 170° C. greater than the temperature of the first conversion zone effluent.

It should be understood that for fluidized bed reactors, the temperature of the effluents not only depend on the temperature of the catalyst but also on other factors such as the flow rate of the catalyst; for fixed-bed reactors (non-steady processes), the temperature of the effluents not only depend on the temperature of the catalyst but also on other factors such as the mass of the catalyst in the reactor. As such, in other embodiments, the first conversion zone effluent can be contacted with the second catalyst at a temperature that can be lower than a temperature of the first catalyst when the hydrocarbon-containing feed contacts the first catalyst, but the temperature of the second conversion zone effluent can still be greater than the temperature of the first conversion zone effluent. For example, the temperature of the second conversion zone effluent can be 30° C., 40° C., 50° C., 60° C., 70° C., or 80° C. to 90° C., 100° C., 110° C., 120° C., 150° C., or 170° C. greater than the temperature of the first conversion zone effluent.

It has been surprisingly and unexpectedly discovered that contacting the hydrocarbon-containing feed with the first catalyst to produce the first conversion zone effluent having the first temperature followed by contacting the first conversion zone effluent with the second catalyst to produce the second conversion zone effluent having the second temperature, where the second temperature is greater than the first temperature, and where the first catalyst and the second catalyst have the same composition, can significantly increase the yield of a desired upgraded hydrocarbon, e.g., propylene, as compared to contacting the same hydrocarbon-containing feed with a catalyst having the same composition as the first and second catalysts within a single conversion such that the single conversion zone effluent has the same temperature as the second conversion zone effluent. It has also been surprisingly and unexpectedly discovered that contacting the hydrocarbon-containing feed with the first catalyst to produce the first conversion zone effluent having the first temperature followed by contacting the first conversion zone effluent with the second catalyst to produce the second conversion zone effluent having the second temperature, where the second temperature is greater than the first temperature, and where the first catalyst and the second catalyst have the same composition can significantly increase the selectivity of a desired upgraded hydrocarbon, e.g., propylene, as compared to contacting the same hydrocarbon-containing feed with a catalyst having the same composition as the first and second catalysts within a single conversion zone such that the single conversion zone effluent has the same temperature as the second conversion zone effluent.

Without wishing to be bound by theory, it is believed that the first conversion zone produces a partially upgraded hydrocarbon. For example, if the hydrocarbon to be upgraded is propane, the first conversion zone effluent includes some propylene, but also includes a relatively large amount of unconverted propane that otherwise would have been converted to propylene or other conversion products if the temperature within the first conversion zone had been greater. It is believed that only partially upgrading the hydrocarbon-containing feed within the first conversion zone produces a first conversion zone effluent that is significantly less susceptible to thermal cracking within the second conversion zone operated at the second temperature, where the temperature of the second conversion zone effluent is greater than the temperature of the first conversion zone effluent.

Furthermore, very high propylene yields have been obtained via the processes and catalysts described herein. In some embodiments, when the hydrocarbon-containing feed includes propane and the upgraded hydrocarbon includes propylene, contacting the hydrocarbon-containing feed with the first catalyst and contacting the first conversion zone effluent with the second catalyst can produce a propylene yield of at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, or at least 69% at a propylene selectivity of at least 75%, at least 80%, at least 85%, at least 90%, or at least 95%. In other embodiments, when the hydrocarbon-containing feed includes at least 70 vol % of propane, based on a total volume of the hydrocarbon-containing feed, contacting the hydrocarbon-containing feed with the first catalyst and contacting the first conversion zone effluent with the second catalyst under a propane partial pressure of at least 20 kPa-absolute, a propylene yield of at least 48%, at least 49%, at least 50%, at least 51%, at least 52%, at least 53%, at least 54%, at least 55%, at least 56%, at least 57%, at least 58%, at least 59%, at least 60%, at least 62%, at least 62%, at least 63%, at least 64%, at least 65%, at least 66%, at least 67%, at least 68%, or at least 69% at a propylene selectivity of at least 75%, at least 80%, at least 85%, at least 90%, or at least 95% can be obtained. It is believed that the propylene yield can be further increased to at least 70%, at least 72%, at least 75%, at least 77%, at least 80%, or at least 82% at a propylene selectivity of at least 75%, at least 80%, at least 85%, at least 90%, or at least 95%. In some embodiments, the propylene yield can be obtained by contacting the hydrocarbon-containing feed with the first catalyst to produce the first conversion zone effluent having a temperature of ≤620° C., ≤610° C., ≤600° C., ≤590° C., or ≤580° C. and by contacting the first conversion zone effluent with the second catalyst to produce the second conversion zone effluent having a temperature of ≥620° C., ≥630° C., ≥640° C., ≥650° C., ≥655° C., ≥660° C., ≥670° C., ≥680° C., ≥690° C., ≥700° C., ≥715° C., ≥725° C., ≥735° C., or ≥750° C. Such a high propylene yield under such processing conditions was not thought possible for first and second catalysts that include a Group 8-10 element, e.g., Pt.

Contacting the hydrocarbon containing feed with the first catalyst and contacting the first conversion zone effluent with the second catalyst can produce a coked first catalyst and a coked second catalyst. At least a portion of the coked first catalyst and/or at least a portion of the coked second catalyst can be contacted with one or more oxidants to effect combustion of at least a portion of the coke to produce a regenerated first catalyst lean in coke and/or a regenerated second catalyst lean in coke and combustion gas(es). In some embodiments the process can optionally include contacting at least a portion of the regenerated first catalyst and/or at least a portion of the regenerated second catalyst with a reducing gas to produce a regenerated and reduced first catalyst and/or a regenerated and reduced second catalyst.

Multi-Stage Hydrocarbon Upgrading Process

The hydrocarbon-containing feed can be contacted with the first catalyst within any suitable first conversion zone to effect one or more of dehydrogenation, dehydroaromatization, and dehydrocyclization of a portion of the hydrocarbon-containing feed to produce the first conversion zone effluent that can include the one or more upgraded hydrocarbons, the molecular hydrogen, and unconverted hydrocarbon-containing feed. The first conversion zone effluent can be contacted with the second catalyst within any suitable second conversion zone to effect one or more of dehydrogenation, dehydroaromatization, and dehydrocyclization of at least a portion of the unconverted hydrocarbon-containing feed in the first conversion zone effluent to produce the second conversion zone effluent that can include an additional quantity of one or more upgraded hydrocarbons and an additional quantity of molecular hydrogen. In some embodiments, a temperature of the second conversion zone effluent can be greater than a temperature of the first conversion zone effluent.

In some embodiments, the process can optionally include contacting the first conversion zone effluent with one or more intermediate catalysts that includes one or more Group 8-10 elements, e.g., Pt, disposed on a support within one or more intermediate conversion zones at one or more intermediate temperatures to effect one or more of dehydrogenation, dehydroaromatization, and dehydrocyclization of a portion of the unconverted hydrocarbon-containing feed in the first conversion zone effluent to produce one or more intermediate conversion zone effluents that can include unconverted hydrocarbon-containing feed and an additional quantity of one or more upgraded hydrocarbons and molecular hydrogen, where a last intermediate conversion zone effluent is contacted with the second catalyst in the second conversion zone. It should be understood that the Group 8-10 element in the one or more intermediate catalysts can be the same or different with respect to one another, can be the same or different with respect to the Group 8-10 element in the first catalyst, and can be the same or different with respect to the Group 8-10 element in the second catalyst. In some embodiments, the number of intermediate conversion zones can be 1, 2, 3, 4, 5, 6, 7, 8, or more. In some embodiments, the temperature of the intermediate conversion zone effluents within any intermediate conversion zone can increase relative to the temperature of the first conversion zone effluent or a previous intermediate conversion zone effluent with the last intermediate conversion zone effluent having a temperature less than the temperature of the second conversion zone effluent. As such, in some embodiments, the temperature of a given intermediate conversion zone effluent can be 5° C., 10° C., 15° C., 20° C., 25° C., 30° C., 35° C., 40° C., 45° C., or 50° C. to 55° C., 60° C., 65° C., 70° C., 75° C., 80° C., 85° C., 90° C., 95° C., 100° C., 105° C., 110° C., 115° C. or 120° C. greater than (i) the temperature of the first conversion zone effluent or (ii) the temperature of any intermediate conversion zone effluent(s) prior to the given intermediate conversion zone effluent. The temperature of the second conversion zone effluent can be greater than the temperature of any intermediate conversion zone effluent(s).

In some embodiments, the first conversion zone, the second conversion zone, and any intermediate conversion zone(s) can all be located within separate reactors. In other embodiments, the first conversion zone, the second conversion zone, and any intermediate conversion zone(s) can all be located within a single reactor, e.g., a riser reactor or a downer reactor, operated such that a temperature gradient increases from an inlet to an outlet of the reactor. In other embodiments, the first conversion zone and, optionally, one or more intermediate conversion zones can be located within a first reactor and the second conversion zone and, optionally, one or more intermediate conversion zones can be located within a second reactor.

In some embodiments, at least one of the first catalyst and the second catalyst and any optional intermediate catalyst(s) can be disposed within a fixed bed. In some embodiments, the first conversion zone and the second conversion zone and any optional intermediate conversion zone(s) can be disposed within a fixed-bed reactor or separate fixed-bed reactors. In some embodiments, the first conversion zone and the second conversion zone and any optional intermediate conversion zone(s) can be disposed within one or more reverse-flow reactors.

In some embodiments, at least one of the first catalyst, the second catalyst, and any optional intermediate catalyst(s) can be in the form of fluidized catalyst particles. In some embodiments, if the first catalyst, the second catalyst, and any intermediate catalyst(s) are all in the form of fluidized catalyst particles, the hydrocarbon-containing feed, the first conversion zone effluent, and any intermediate conversion zone effluent(s) can be contacted within conversion zones disposed within a continuous type process commonly employed in fluidized bed reactors. In some embodiments, the first conversion zone and the second conversion zone and any optional intermediate conversion zone(s) can be disposed within a riser reactor or a downer reactor. In at least one embodiment, the first conversion zone can be disposed within a riser reactor and the second conversion zone can be disposed in a downer reactor or the first conversion zone can be disposed within a downer reactor and the second conversion zone can be disposed within a riser reactor. If any intermediate conversion zone(s) is present, the intermediate conversion zone(s) can be disposed in a downer reactor and/or a riser reactor. In other embodiments, the first conversion zone can be disposed within a first vortex reactor and the second conversion zone can be disposed within a second vortex reactor and any optional intermediate conversion zone(s) can be disposed in one or more intermediate vortex reactors. Suitable vortex reactors can include those described in Chemical Engineering and Processing 85 (2014) 256-290. In other embodiments, the first conversion zone, the second conversion zone, and any intermediate conversion zone(s) can be disposed within one or more reactors that can allow the fluidized catalyst particles to form a relatively dense turbulent fluidized bed therein during contact with the hydrocarbon-containing feed. A relatively dense turbulent fluidized bed refers to a fluidized bed that is at a superficial gas velocity above the transition velocity designated as the critical velocity between the transition of a bubbling and turbulent bed, but below the transport velocity that demarcates a fast fluidization regime in which the catalyst particles are conveyed such as in a riser reactor.

Any number of reactors can be operated in series and/or in parallel. Any two or more types of reactors can be used in combination with one another. In some embodiments, suitable reactors can be or can include, but are not limited to, high gas velocity riser reactors, high gas velocity downer reactors, vortex reactors, reactors having a relatively dense fluidized catalyst bed at a first or bottom end (first conversion zone) and a relatively less dense fluidized catalyst within a riser located at a second or top end (second conversion zone), multiple riser reactors and/or downer reactors operated in parallel and/or series, or combinations thereof. It has been found that shorter gas residence times can achieve a higher product selectivity (see Example 5+6 versus Example 2+3 below), with the shorter gas residence times preferably achieved in reactors with high gas velocities.

In some embodiments, when the catalysts are in the form of fluidized catalyst particles, the first fluidized catalyst particles, the second fluidized catalyst particles, and any intermediate fluidized catalyst particles can be pneumatically moved through the reaction system, e.g., fed into the first conversion zone, fed into any intermediate conversion zone, fed into the second conversion zone, fed into a combustion zone, fed into a reduction zone, transported through conduits connecting two or more locations, and the like, via a carrier fluid or transport fluid. The transport fluid can be or can include, but is not limited to, a diluent, one or more of the reactants in gaseous form, i.e., the one or more $C_2$-$C_{16}$ alkanes, the one or more $C_8$-$C_{16}$ alkyl aromatic hydrocarbons, or a mixture thereof. Suitable transport fluids can be or can include, but are not limited to, molecular hydrogen, molecular nitrogen, volatile hydrocarbons such as methane ($CH_4$), ethane ($C_2H_6$), and/or propane ($C_3H_8$), argon (Ar), carbon monoxide (CO), carbon dioxide ($CO_2$), steam ($H_2O$), and mixtures thereof. The amount of transport fluid can be sufficient to maintain the catalyst particles in a fluidized state and to transport the catalyst particles from one location, e.g., the combustion zone or the regeneration zone, to a second location, e.g., the first conversion zone or the second conversion zone. In some embodiments, a weight ratio of the fluidized catalyst particles to the transport fluid can be in a range from 5, 10, 15, or 20 to 50, 60, 80, 90, or 100. Injection points for the transport fluid, as can be made at multiple points along any one or more transfer lines that connect any two zones or other locations such as the combustion zone and the second conversion zone or the regeneration zone and the second conversion zone.

The hydrocarbon-containing feed and the first catalyst can be contacted to produce the first conversion zone effluent that can have a temperature in a range from 300° C., 350° C., 400° C., 450° C., 500° C., 550° C., 600° C., 620° C., 630° C., 640° C., or 650° C. to 660° C., 670° C., 680° C., 690° C., 700° C. to 725° C., 750° C., 760° C., 780° C., 800° C., 825° C., or 850° C. In some embodiments, the hydrocarbon-containing feed and the first catalyst can be contacted to produce the first conversion zone effluent that can have a temperature of ≤800° C., ≤750° C., ≤700° C., ≤650° C., ≤620° C., ≤600° C., ≤590° C., or ≤580° C. The hydrocarbon-containing feed and the first catalyst can be contacted for a time period in a range from 0.1 seconds, 0.5 seconds, 1 second, 2 seconds, 5 seconds, 10 seconds, 30 seconds, 45 seconds, or 1 minute to 5 minutes, 30 minutes, 1 hour, 1.5 hours, 2 hours, 2.5 hours, or 3 hours.

The hydrocarbon-containing feed and the first catalyst can be contacted under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. In some embodiments, the hydrocarbon partial pressure during contact of the hydrocarbon-containing feed and the first catalyst can be in a range from 20 kPa-absolute, 50 kPa-absolute, 100 kPa-absolute, at least 150 kPa, at least 200 kPa 300 kPa-absolute, 500 kPa-absolute, 750 kPa-absolute, or 1,000 kPa-absolute to 1,500 kPa-absolute, 2,500 kPa-absolute, 4,000 kPa-absolute, 5,000 kPa-absolute, 7,000 kPa-absolute, 8,500 kPa-absolute, or 10,000 kPa-absolute, where the hydrocarbon partial pressure is the total partial pressure of any $C_2$-$C_{16}$ alkanes and any $C_8$-$C_{16}$ alkyl aromatics in the hydrocarbon-containing feed. In other embodiments, the hydrocarbon partial pressure during contact of the hydrocarbon-containing feed and the first catalyst can be in a range from 20 kPa-absolute, 50 kPa-absolute, 100 kPa-absolute, 150 kPa-absolute, 200 kPa-absolute, 250 kPa-absolute, or 300 kPa-absolute to 500 kPa-absolute, 600 kPa-absolute, 700 kPa-absolute, 800 kPa-absolute, 900 kPa-absolute, or 1,000 kPa-absolute, where the hydrocarbon partial pressure is the total partial pressure of any $C_2$-$C_{16}$ alkanes and any $C_8$-$C_{16}$ alkyl aromatics in the hydrocarbon-containing feed.

In some embodiments, the hydrocarbon-containing feed can include at least 60 vol %, at least 65 vol %, at least 70 vol %, at least 75 vol %, at least 80 vol %, at least 85 vol %, at least 90 vol %, at least 95 vol %, or at least 99 vol % of a single $C_2$-$C_{16}$ alkane, e.g., propane, based on a total volume of the hydrocarbon-containing feed. The hydrocarbon-containing feed and the first catalyst can be contacted under a single $C_2$-$C_{16}$ alkane, e.g., propane, pressure of at least 20 kPa-absolute, at least 50 kPa-absolute, at least 100 kPa-absolute, at least 150 kPa-absolute, at least 250 kPa-absolute, at least 300 kPa-absolute, at least 400 kPa-absolute, at least 500 kPa-absolute, or at least 1,000 kPa-absolute.

The hydrocarbon-containing feed can be contacted with the first catalyst within the first conversion zone at any weight hourly space velocity (WHSV) effective for carrying out the upgrading process. In some embodiments, the WHSV within the first conversion zone can be 0.01 hr$^{-1}$, 0.1 hr$^{-1}$, 1 hr$^{-1}$, 2 hr$^{-1}$, 5 hr$^{-1}$, 10 hr$^{-1}$, 20 hr$^{-1}$, 30 hr$^{-1}$, or 50 hr$^{-1}$ to 100 hr$^{-1}$, 250 hr$^{-1}$, 500 hr$^{-1}$, or 1,000 hr$^{1}$.

In some embodiments, if the hydrocarbon upgrading process includes a fluidized or otherwise moving first catalyst particles, a ratio of the first catalyst particles to a combined amount of any $C_2$-$C_{16}$ alkanes and any $C_8$-$C_{16}$ alkyl aromatics in the hydrocarbon-containing feed within the first conversion zone can be in a range from 1, 3, 5, 10, 15, 20, 25, 30, or 40 to 50, 60, 70, 80, 90, 100, 110, 125, or 150 on a weight to weight basis. In some embodiments, if the hydrocarbon upgrading process includes a fluidized or otherwise moving first catalyst particles, a temperature of the first catalyst particles introduced into the first conversion zone can be in a range of from 10° C., 20° C., 30° C., 40° C., 50° C., 60° C., 70° C. or 80° C. to 100° C., 115° C., 130° C., 150° C., 175° C., or 200° C. greater than a temperature of the first conversion zone effluent. In other embodiments, if the hydrocarbon upgrading process includes a fluidized or otherwise moving first catalyst particles, a ratio of the first catalyst particles to a combined amount of any $C_2$-$C_{16}$ alkanes and any $C_8$-$C_{16}$ alkyl aromatics in the hydrocarbon-containing feed within the first conversion zone can be in a range from 10 to 100, or from 15 to 80, or from 20 to 70, or from 25 to 60 and a temperature of the first catalyst particles introduced into the first conversion zone can be in a range of from 10° C., 20° C., 30° C., or 40° C. to 70° C., 80° C., 90° C., or 100° C. greater than a temperature of the first conversion zone effluent.

The first conversion zone effluent and the second catalyst can be contacted to produce a second conversion zone effluent that can have a temperature in a range from 350° C., 400° C., 450° C., 500° C., 550° C., 600° C., 620° C., 630° C., 640° C., 650° C., 660° C., 670° C., 680° C., 690° C., or 700° C. to 725° C., 750° C., 760° C., 780° C., 800° C., 825° C., 850° C., 875° C., or 900° C. In some embodiments, the first conversion zone effluent and the second catalyst can be contacted to produce a second conversion zone effluent that can have a temperature of at least 600° C., at least 620° C., at least 630° C., at least 640° C., at least 650° C., at least 660° C., at least 670° C., at least 680° C., at least 690° C., or at least 700° C. to 725° C., 750° C., 760° C., 780° C., 800° C., 825° C., 850° C., 875° C., or 900° C. In some embodiments, the first conversion zone effluent and the second catalyst can be contacted for a time period in a range from 0.1 seconds, 0.5 seconds, 1 second, 2 seconds, 5 seconds, 10 seconds, 30 seconds, 45 seconds, or 1 minute to 5 minutes, 30 minutes, 1 hour, 1.5 hours, 2 hours, 2.5 hours, or 3 hours.

The first conversion zone effluent and the second catalyst can be contacted under a hydrocarbon partial pressure of at least 20 kPa-absolute, where the hydrocarbon partial pressure is the total partial pressure of any $C_2$-$C_{16}$ alkanes and any $C_8$-$C_{16}$ alkyl aromatics in the first conversion zone effluent. In some embodiments, the hydrocarbon partial pressure during contact of the first conversion zone effluent and the second catalyst can be in a range from 20 kPa-absolute, 50 kPa-absolute, 100 kPa-absolute, at least 150 kPa, at least 200 kPa 300 kPa-absolute, 500 kPa-absolute, 750 kPa-absolute, or 1,000 kPa-absolute to 1,500 kPa-absolute, 2,500 kPa-absolute, 4,000 kPa-absolute, 5,000 kPa-absolute, 7,000 kPa-absolute, 8,500 kPa-absolute, or 10,000 kPa-absolute, where the hydrocarbon partial pressure is the total partial pressure of any $C_2$-$C_{16}$ alkanes and any $C_8$-$C_{16}$ alkyl aromatics in the first conversion zone effluent. In other embodiments, the hydrocarbon partial pressure during contact of the first conversion zone effluent and the second catalyst can be in a range from 20 kPa-absolute, 50 kPa-absolute, 100 kPa-absolute, 150 kPa-absolute, 200 kPa-absolute, 250 kPa-absolute, or 300 kPa-absolute to 500 kPa-absolute, 600 kPa-absolute, 700 kPa-absolute, 800 kPa-absolute, 900 kPa-absolute, or 1,000 kPa-absolute, where the hydrocarbon partial pressure is the total partial pressure of any $C_2$-$C_{16}$ alkanes and any $C_8$-$C_{16}$ alkyl aromatics in the first conversion zone effluent.

In some embodiments, the conversion of the hydrocarbon in the first conversion zone can be in a range of from 10%, 15%, 20%, or 25%, to 30%, 35%, 40%, 45%, 50%, 55%, 60% or 65% based on a total volume of the upgraded hydrocarbons, any $C_2$-$C_{16}$ alkanes, any $C_4$-$C_{16}$ cyclic alkanes, and any $C_8$-$C_{16}$ alkyl aromatics in the first conversion zone effluent. The first conversion zone effluent and the second catalyst can be contacted under a single $C_2$-$C_{16}$ alkane, e.g., propane, pressure of at least 20 kPa-absolute, at least 50 kPa-absolute, at least 100 kPa-absolute, at least 150 kPa-absolute, at least 250 kPa-absolute, at least 300 kPa-absolute, at least 400 kPa-absolute, at least 500 kPa-absolute, or at least 1,000 kPa-absolute.

The first conversion zone effluent can be contacted with the second catalyst within the second conversion zone at any weight hourly space velocity (WHSV) effective for carrying out the upgrading process. In some embodiments, the WHSV in the second conversion zone can be 0.01 hr$^{-1}$, 0.1 hr$^{-1}$, 1 hr$^{-1}$, 2 hr$^{-1}$, 5 hr$^{-1}$, 10 hr$^{-1}$, 20 hr$^{-1}$, 30 hr$^{-1}$, or 50 hr$^{-1}$ to 100 hr$^{-1}$, 250 hr$^{-1}$, 500 hr$^{-1}$, or 1,000 hr$^{-1}$. In some embodiments, if the hydrocarbon upgrading process includes a fluidized or otherwise moving second catalyst particles, a ratio of the second catalyst particles to a combined amount of any $C_2$-$C_{16}$ alkanes and any $C_8$-$C_{16}$ alkyl aromatics in the first conversion zone effluent within the second conversion zone can be in a range from 1, 3, 5, 10, 15, 20, or 25 to 30, 40, 50, 60, or 70 on a weight to weight basis. In some embodiments, if the hydrocarbon upgrading process includes a fluidized or otherwise moving first catalyst particles and second catalyst particles, a ratio of a combined amount of the first catalyst particles and the second catalyst particles to a combined amount of any $C_2$-$C_{16}$ alkanes and any $C_8$-$C_{16}$ alkyl aromatics in the first conversion zone effluent within the second conversion zone can be in a range from 2, 3, 5, 10, 15, 20, 25, 30, or 40 to 50, 60, 70, 80, 90, 100, 110, 125, 150, 170, 200, or 220 on a weight to weight basis.

In some embodiments, if the hydrocarbon process includes fluidized or otherwise moving first and second catalyst particles, the weight ratio of the first catalyst particles to the combined amount of any $C_2$-$C_{16}$ alkanes and any $C_8$-$C_{16}$ alkyl aromatics within the second conversion zone can be greater than the weight ratio of the second catalyst particles to the combined amount of any $C_2$-$C_{16}$ alkanes and any $C_8$-$C_{16}$ alkyl aromatics within the second conversion zone. In some embodiments, if the hydrocarbon upgrading process includes fluidized or otherwise moving second catalyst particles, a temperature of the second catalyst particles introduced into the second conversion zone can be in a range of from 30° C., 50° C., 100° C., or 150° C. to 200° C., 250° C., 275° C., or 300° C. greater than a temperature of the first conversion zone effluent.

In some embodiments, if the upgrading process includes one or more intermediate conversion zones, the process conditions can be substantially the same as the process conditions within the first conversion zone and/or the second conversion zone. In some embodiments, the temperature of the effluent recovered from the one or more intermediate conversion zones can be greater than the temperature of the first conversion zone effluent and less than the temperature of the second conversion zone effluent. In some embodiments, if the upgrading process includes two or more intermediate conversion zones, the temperature of the effluents in successive intermediate conversion zone can be greater than the preceding intermediate conversion zone effluent. In some embodiments, if the hydrocarbon upgrading process includes fluidized or otherwise moving one or more pluralities of intermediate catalyst particles, a ratio of each the one or more pluralities of intermediate catalyst particles to a combined amount of any $C_2$-$C_{16}$ alkanes and any $C_8$-$C_{16}$ alkyl aromatics in each of the first conversion zone effluent or any preceding intermediate conversion zone effluents can be in a range from 1, 3, 5, 10, 15, 20, 25, 30, or 40 to 50, 60, 70, 80, 90, 100, 110, 125, or 150 on a weight to weight basis. In some embodiments, if the hydrocarbon upgrading process includes a fluidized or otherwise moving first catalyst particles, one or more intermediate catalyst particles, and second catalyst particles, a ratio of a combined amount of the first catalyst particles, the one or more intermediate catalyst particles, and the second catalyst particles to a combined amount of any $C_2$-$C_{16}$ alkanes and any $C_8$-$C_{16}$ alkyl aromatics in the first conversion zone effluent or a last intermediate conversion zone effluent within the second conversion zone can be in a range from 3, 5, 10, 15, 20, 25, 30, or 40 to 50, 60, 70, 80, 90, 100, 110, 125, or 150, 175, 200, 250, or 300 on a weight to weight basis.

In some embodiments, if the hydrocarbon upgrading process includes a fluidized or otherwise moving first catalyst particles, optionally one or more intermediate catalyst particles, and second catalyst particles, a ratio of the second catalyst particles to a combined amount of any $C_2$-$C_{16}$ alkanes and any $C_8$-$C_{16}$ alkyl aromatics in the first conversion zone effluent or a last intermediate conversion zone effluent within the second conversion zone can be in a range from 1, 5, 10, 15, or 20 to 30, 40, 45, or 50 on a weight to weight basis; a ratio of a combined amount of the first catalyst particles, any intermediate catalyst particles, and the second catalyst particles to a combined amount of any $C_2$-$C_{16}$ alkanes and any $C_8$-$C_{16}$ alkyl aromatics in the first conversion zone effluent or a last intermediate conversion zone effluent within the second conversion zone can be in a range from 3, 5, 10, 15, 20, 25, 30, or 35 to 45, 50, 60, 70, or 80 on a weight to weight basis, and a temperature of a combined mixture of the first catalyst particles, any intermediate catalyst particles, and the second catalyst particles introduced into the second conversion zone can be in a range of from 5° C., 7° C., 10° C., or 15° C. to 20° C., 30° C., 40° C., or 50° C. greater than a temperature of the second conversion zone effluent.

In some embodiments, if the first catalyst, any intermediate catalyst, and/or the second catalyst are in the form of fluidized catalyst particles, at least a portion of the fluidized catalyst particles within the first conversion zone, any intermediate conversion zone, and/or the second conversion zone can be removed, fed into a heat input device where the catalyst particles can be heated, and the heated catalyst particles can be fed back into the conversion zone. The heat can be indirectly transferred from any suitable heat transfer medium, provided via an electric heater, or any other suitable heater typically used to indirectly heat catalyst particles. In another embodiment, a way of effecting a temperature gradient within one or more of the conversion zones can be to have a countercurrent flow of reactant and the catalyst. The temperature of the catalyst decreases while travelling through the reactor due to the endothermicity of the reaction while the temperature of the product/reactant increases while travelling through the reactor due to the hotter catalyst coming in from the other end of the reactor. Such counter current flow can be carried out as described in WO Publication No. WO 2014/081545. In some embodiments, if the first catalyst, any intermediate catalyst, and the second catalyst are in the form of fluidized catalyst particles, the conversion reactions within the first conversion zone, any intermediate conversion zone, and the second conversion zone can be carried out substantially adiabatically, such that there is no addition or removal of heat from the conversion zones other than natural heat losses from the conversion zones to the environment. The heat required for the reactions within the first conversion zone, any intermediate conversion zone(s), and the second conversion zone can come from the first catalyst, any intermediate catalyst, and the second catalyst flowing through the conversion zones.

In other embodiments, heat can be applied within the conversion zone directly. As such, heat can be input into one or more of the first conversion zone, any intermediate conversion zone(s), and/or the second conversion zone where the catalyst(s) is in the form of fluidized catalyst particles, disposed within packed beds, is in the form of monolithic structures, or the like. In some embodiments, one or more tubes or channels can be embedded or otherwise located within the conversion zone and a heated fluid can flow through the tube or channel and indirectly transfer heat into one or more of the conversion zones. In other embodiments, electric heating elements can be used to provide heat within one or more of the conversion zones. In other embodiments, one or more heating jackets can be disposed about one or more of the conversion zones to transfer heat into the conversion zone. In other embodiments, when the first catalyst, any intermediate catalyst, and the second catalyst are disposed within one or more fixed bed reactors, the catalyst and/or inert solids can be heated in a separate cycle from the dehydrogenation, dehydroaromatization, and/or dehydrocyclization reactions occurring within the conversion zones. Such heating can occur from combustion of coke disposed on the first catalyst, any intermediate catalyst, and the second catalyst in the presence of an oxidant, e.g., air, and/or from combustion of a supplemental fuel. After heating the solids sufficiently, the reactor(s) can be cycled back to the dehydrogenation, dehydroaromatization, and/or dehydrocyclization reactions. When the flow of combustion gas and the flow of reacting gases are in opposite directions, this is referred to as a reverse flow reactor. The optional supplemental fuel can be or can include, but is not limited to, molecular hydrogen, methane, ethane, propane, or a mixture thereof. The optional supplemental fuel can be mixed with an inert gas such as argon, neon, helium, molecular nitrogen, methane, or a mixture thereof.

In some embodiments, if the first catalyst, any intermediate catalyst, and/or the second catalyst are in the form of fluidized catalyst particles, conversion zone effluent(s) can be separated or otherwise obtained from the coked catalyst(s) via any suitable apparatus. In some embodiments, the conversion zone effluent(s) can be separated or otherwise obtained via one or more solid-gas impingement separators, e.g., one or more cyclone separators. In some examples, the cyclone separator can be or can include a two staged or "coupled" configuration including both positive and negative pressure configurations. In some embodiments, suitable cyclone separators can include those disclosed in U.S. Pat. Nos. 4,502,947; 4,985,136; and 5,248,411. In other embodiments, the coked catalyst particles and the conversion zone effluents can be obtained from the conversion zine effluent(s) via a "T" shaped conduit that can cause the catalyst particles to flow in one direction via gravity and the gaseous components to flow in the other direction.

Contacting the hydrocarbon-containing feed with the first catalyst and contacting the first conversion zone effluent with the second catalyst or intermediate catalyst(s) or contacting the first conversion zone effluent or the intermediate conversion zone effluent with the second catalyst can produce a coked first catalyst, a coked intermediate catalyst(s), and a coked second catalyst. When the activity of the coked first catalyst, any coked intermediate catalyst, and/or the coked second catalyst decreases below a desired minimum amount, the coked first catalyst or at least a portion thereof, the coked intermediate catalyst or at least a portion thereof, and/or the coked second catalyst or at least a portion thereof can be contacted with one or more oxidants within the respective conversion zone or within a combustion zone that is separate and apart from the conversion zones, depending on the particular reactor configuration and whether the catalysts are in fixed beds or fluidized particles, to produce a regenerated first catalyst, a regenerated intermediate catalyst(s), and/or a regenerated second catalyst each lean in coke and combustion gas(es).

The oxidant can be or can include, but is not limited to, molecular oxygen ($O_2$), ozone ($O_3$), carbon dioxide ($CO_2$), steam ($H_2O$), or a mixture thereof. For simplicity and ease of description the term "coked catalyst(s)" will be used in describing the process conditions for combustion of the coked catalyst and optional reduction of the regenerated catalyst. It should be understood that the coked catalyst(s) can be or can include the coked first catalyst, any coked intermediate catalyst, the coked second catalyst, or, when the catalysts are all the form of fluidized particles, a mixture of the coked first catalyst, any coked intermediate catalyst, and the coked second catalyst when the first catalyst, any intermediate catalyst, and the second catalyst. In some embodiments, an amount of oxidant in excess of that needed to combust 100% of the coke on the coked catalyst(s) can be used to increase the rate of coke removal from the catalyst(s), so that the time needed for coke removal can be reduced and lead to an increased yield in the upgraded product produced within a given period of time.

The coked catalyst(s) and oxidant can be contacted with one another at a temperature in a range from 500° C., 550° C., 580° C., 600° C., 650° C., 700° C., 750° C., or 800° C. to 900° C., 950° C., 1,000° C., 1,050° C., or 1,100° C. to produce the regenerated catalyst(s). In some embodiments, the coked catalyst(s) and oxidant can be contacted with one another at a temperature in a range from 500° C. to 1,100° C., 600° C. to 1,000° C., 650° C. to 950° C., 700° C. to 900° C., or 750° C. to 850° C. to produce the regenerated catalyst.

The coked catalyst(s) and oxidant can be contacted with one another for a time period of ≤2 hours, ≤1 hour, ≤45 minutes, ≤30 minutes, ≤25 minutes, ≤20 minutes, ≤15 minutes, ≤10 minutes, ≤5 minutes, ≤1 min, ≤30 seconds, ≤10 seconds, ≤5 seconds, or ≤1 second. For example, the coked catalyst(s) and oxidant can be contacted with one another for a time period in a range from 2 seconds to 2 hours. In some embodiments, the coked catalyst(s) and oxidant can be contacted for a time period sufficient to remove ≥50 wt %, ≥75 wt %, or ≥90 wt % or ≥99% of any coke disposed on the catalyst(s).

The coked catalyst(s) and oxidant can be contacted with one another under an oxidant partial pressure in a range from 5 kPa-absolute, 10 kPa-absolute, 15 kPa-absolute, 20 kPa-absolute, 50 kPa-absolute, 100 kPa-absolute, 300 kPa-absolute, 500 kPa-absolute, 750 kPa-absolute, or 1,000 kPa-absolute to 1,500 kPa-absolute, 2,500 kPa-absolute, 4,000 kPa-absolute, 5,000 kPa-absolute, 7,000 kPa-absolute, 8,500 kPa-absolute, or 10,000 kPa-absolute. In other embodiments, the oxidant partial pressure during contact with the coked catalyst(s) can be in a range from 5 kPa-absolute, 10 kPa-absolute, 15 kPa-absolute, 20 kPa-absolute, or 50 kPa-absolute to 100 kPa-absolute, 150 kPa-absolute, 200 kPa-absolute, 250 kPa-absolute, 300 kPa-absolute to 500 kPa-absolute, 600 kPa-absolute, 700 kPa-absolute, 800 kPa-absolute, 900 kPa-absolute, or 1,000 kPa-absolute to produce the regenerated catalyst(s).

In some embodiments, in addition to the coked catalyst particles, one or more supplemental fuels can also be contacted with the oxidant within the respective conversion zone or within the combustion zone to effect combustion of at least a portion of the supplemental fuel to produce heat and additional combustion gas. The optional supplemental fuel can be or can include, but is not limited to, molecular hydrogen ($H_2$), methane ($CH_4$), ethane ($C_2H_6$), propane ($C_3H_8$), or a mixture thereof. The optional supplemental fuel can be mixed with an inert gas such as argon (Ar), neon (Ne), helium (He), molecular nitrogen ($N_2$), or a mixture thereof.

Without wishing to be bound by theory, it is believed that at least a portion of the Group 8-10 element, e.g., Pt, disposed on the coked catalyst(s) can be agglomerated as compared to the catalyst(s) prior to contact with the hydrocarbon-containing feed, the first conversion zone effluent, and any intermediate conversion zone effluent(s). It is believed that during combustion of at least a portion of the coke on the coked catalyst(s) that at least a portion of the Group 8-10 element can be re-dispersed about the support. Re-dispersing at least a portion of any agglomerated Group 8-10 element can increase the activity and improve the stability of the catalyst(s) over many cycles.

In some embodiments, at least a portion of the Group 8-10 element, e.g., Pt, in the regenerated catalyst(s) can be at a higher oxidized state as compared to the Group 8-10 element in the catalyst(s) contacted with the hydrocarbon-containing feed, the first conversion zone effluent, any intermediate conversion zone effluent, and as compared to the Group 8-10 element in the coked catalyst(s). The regenerated catalyst(s) disclosed herein may exhibit improved activity and selectivity after undergoing an additional reduction step prior to recontact with the hydrocarbon-containing feed, the first conversion zone effluent, or any intermediate conversion zone effluent. As such, as noted above, in some embodiments the process can optionally include contacting at least a portion of the regenerated catalyst(s) with a reducing gas to produce regenerated and reduced catalyst(s). Suitable reducing gases (reducing agent) can be or can include, but are not limited to, molecular hydrogen ($H_2$), carbon monoxide (CO), methane ($CH_4$), ethane ($C_2H_6$), propane ($C_3H_8$), ethylene ($C_2H4$), propylene ($C_3H_6$), steam, or a mixture thereof. In some embodiments, the reducing gas can be mixed with an inert gas such as argon (Ar), neon (Ne), helium (He), molecular nitrogen ($N_2$), carbon dioxide ($CO_2$), steam ($H_2O$), or a mixture thereof. In such embodiments, at least a portion of the Group 8-10 element in the regenerated and reduced catalyst(s) can be reduced to a lower oxidation state, e.g., the elemental state, as compared to the Group 8-10 element in the regenerated catalyst(s).

In some embodiments, the regenerated catalyst(s) and the reducing gas can be contacted at a temperature in a range from 400° C., 450° C., 500° C., 550° C., 600° C., 620° C., 650° C., or 670° C. to 720° C., 750° C., 800° C., or 900° C. In other embodiments, the regenerated catalyst(s) and the reducing gas can be contacted substantially adiabatically, i.e., no heat is intentionally added or removed during the contacting but some heat may be lost to the environment, such that the heat can be provided from the regenerated catalyst(s). The regenerated catalyst(s) and the reducing gas can be contacted for a time period in a range from 0.1 second, 1 second, 5 seconds, 10 seconds, 20 seconds, 30 seconds, or 1 minute to 5 minutes, 10 minutes, 15 minutes, 20 minutes, 25 minutes, 30 minutes, 35 minutes, 40 minutes, 45 minutes 50 minutes, 55 minutes, or 60 minutes. The regenerated catalyst(s) and reducing gas can be contacted at a reducing agent partial pressure of 0.01 kPa-absolute, 0.1 kPa-absolute, 0.5 kPa-absolute, 1 kPa-absolute, 5 kPa-absolute, 10 kPa-absolute, 20 kPa-absolute, 50 kPa-absolute, or 100 kPa-absolute, 300 kPa-absolute, 500 kPa-absolute, 750 kPa-absolute, or 1,000 kPa-absolute to 1,500 kPa-absolute, 2,500 kPa-absolute, 4,000 kPa-absolute, 5,000 kPa-absolute, 7,000 kPa-absolute, 8,500 kPa-absolute, or 10,000 kPa-absolute. In other embodiments, the reducing agent partial pressure during contact with the regenerated catalyst(s) can be in a range from 0.01 kPa-absolute, 0.1 kPa-absolute, 0.5 kPa-absolute, 1 kPa-absolute, 5 kPa-absolute, 10 kPa-absolute, 20 kPa-absolute, 50 kPa-absolute, 100 kPa-absolute, 150 kPa-absolute, 200 kPa-absolute, 250 kPa-absolute, or 300 kPa-absolute to 500 kPa-absolute, 600 kPa-absolute, 700 kPa-absolute, 800 kPa-absolute, 900 kPa-absolute, or 1,000 kPa-absolute to produce the regenerated and reduced catalyst(s).

At least a portion of the regenerated catalyst(s), the regenerated and reduced catalyst(s), new or fresh catalyst, or a mixture thereof can be contacted with an additional quantity of the hydrocarbon-containing feed, first conversion zone effluent, and any intermediate conversion zone effluents within the respective conversion zone to produce additional effluents and additional coked catalyst(s).

In some embodiments, one or more additional feeds, e.g., one or more sweep fluids, can be utilized between flows of the hydrocarbon-containing feed and the oxidant, between the oxidant and the optional reducing gas if used, between the oxidant and the additional hydrocarbon-containing feed, and/or between the reducing gas and the additional hydrocarbon-containing feed. The sweep fluid can, among other things, purge or otherwise urge undesired material from the conversion zones, such as non-combustible particulates including soot. In some embodiments, the additional feed(s) can be inert under the dehydrogenation, dehydroaromatization, and dehydrocyclization, combustion, and/or reducing conditions. Suitable sweep fluids can be of can include, but are not limited to, molecular nitrogen ($N_2$), helium (He), argon (Ar), carbon dioxide ($CO_2$), steam ($H_2O$), carbon dioxide ($CO_2$), methane ($CH_4$), or a mixture thereof. In some embodiments, if the process utilizes a sweep fluid the duration or time period the sweep fluid is used can be in a range from 1 second, 5 seconds, 10 seconds, 20 seconds, 30 seconds, or 1 minute to 10 minutes, 30 minutes, or 60 minutes.

It has been surprisingly and unexpectedly discovered that the first catalyst, the intermediate catalyst, and the second catalyst that include the Group 8-10 element, e.g., Pt, disposed on the support can remain sufficiently active and stable after many cycles, e.g., at least 15, at least 20, at least 30, at least 40, at least 50, at least 60, at least 70, at least 100 cycles, at least 125 cycles, at least 150 cycles, at least 175 cycles, or at least 200 cycles with each cycle time lasting for ≤3 hours. In some embodiments, the cycle time can be ≤5 hours, ≤4 hours, ≤3 hours, ≤2 hours, ≤1 hour, ≤50 minutes, ≤45 minutes, ≤30 minutes, ≤15 minutes, ≤10 minutes, ≤5 minutes, ≤1 minute, ≤30 seconds, or ≤10 seconds. In some embodiments, the cycle time can be from 5 seconds, 30 seconds, 1 minute or 5 minutes to 10 minutes, 20 minutes, 30 minutes, 45 minutes, 50 minutes, 60 minutes, 70 minutes, 2 hours, 3 hours, 4 hours, or 5 hours. The first cycle begins upon contact of the second catalyst with the first conversion zone effluent or the last intermediate conversion zone effluent, followed by contact of at least a portion of the coked first catalyst, at least a portion of any coked intermediate catalysts, at least a portion of the coked second catalyst, or a mixture thereof with at least the oxidant to produce the regenerated second catalyst or at least the oxidant and the optional reducing gas to produce the regenerated and reduced second catalyst, and the first cycle ends upon contact of the regenerated second catalyst or the regenerated and reduced second catalyst particles with an additional quantity of the first conversion zone effluent or the last intermediate conversion zone effluent. The second and each subsequent cycle begins upon contact of the regenerated second catalyst or the regenerated and reduced second catalyst and the additional quantity of the first conversion zone effluent or the last intermediate conversion zone effluent and the second and each subsequent cycle ends upon contact of additional or subsequently regenerated second catalyst or regenerated and reduced second catalyst with the additional quantity of the first conversion zone effluent or the last intermediate conversion zone effluent.

In some embodiments, after the performance of the catalyst(s) stabilize (sometimes the first few cycles can have a relatively poor or relatively good performance, but the performance can eventually stabilize), the process can produce an upgraded hydrocarbon product yield, e.g., propylene when the hydrocarbon-containing feed includes propane, at an upgraded hydrocarbon selectivity, e.g., propylene, of ≥_75%, ≥80%, ≥85%, or ≥90%, or ≥95% when initially contacted with the hydrocarbon-containing feed, the first conversion zone effluent, and any intermediate conversion zone effluent(s), and can have a second upgraded hydrocarbon product yield upon completion of the last cycle (at least 15 cycles total) that can be at least 90%, at least 93%, at least 95%, at least 97%, at least 98%, at least 99%, at least 99.5%, or at least 100% of the first upgraded hydrocarbon product yield at an upgraded hydrocarbon selectivity, e.g., propylene, of ≥75%, ≥80%, ≥85%, or ≥90%, or >95%. Prior to this discovery, it was believed that catalyst(s) having the Group 8-10 element, e.g., Pt, as the active component would not maintain sufficient activity and stability when subjected to so many short cycles with a simple oxidative regeneration that requires no addition of halogen.

In some embodiments, when the first catalyst, the second catalyst, and any intermediate catalysts are in the form of fluidized catalyst particles the catalyst particles can move with the conversion zone effluents through each conversion zone. In such embodiments, a gaseous stream rich in upgraded hydrocarbon(s) and a particle stream rich in coked catalyst particles, i.e., the coked first catalyst, any coked intermediate catalyst, and the coked second catalyst can be obtained from the second conversion zone effluent. In some embodiments, a first portion of the coked catalyst particles in the particle stream rich in coked catalyst particles can be fed into the combustion zone for regeneration of the first portion of the coked catalyst particles and a second portion of the coked catalyst particles can be recycled directly back into the first conversion zone and/or one or more of the intermediate conversion zones. In other embodiments, a first portion of the coked catalyst particles in the particle stream rich in coked catalyst particles can be fed into the combustion zone for regeneration of the first portion of the coked catalyst particles, a second portion of the coked catalyst particles can be recycled directly back into the first conversion zone and/or one or more intermediate conversion zones, and a third portion of the coked catalyst particles can be fed into the reduction zone. In any of these embodiments, on a continuous basis or intermittent basis, a portion of the coked catalyst particles, a portion of the regenerated catalyst particles, and/or a portion of the regenerated and reduced catalyst particles can be removed from the process and new or make-up catalyst particles can be introduced into the process. The removal of catalyst particles can be done as the catalyst particles break down in size, become inactivated, or begin to convert the hydrocarbon-containing feed at an undesirable rate of conversion.

In some embodiments, one or more additional feeds, e.g., one or more stripping fluids, can be utilized to remove at least a portion of any entrained gaseous components from the catalyst(s). In some examples, the coked catalyst(s) can be contacted with a stripping fluid prior to contact with the oxidant and/or reducing gas to remove at least a portion of any entrained upgraded hydrocarbons and/or molecular hydrogen, and/or other gaseous components. Similarly, the regenerated catalyst particles and/or the regenerated and reduced catalyst particles can be contacted with a stripping gas to remove at least a portion of any entrained combustion gas or reducing gas therefrom. In some embodiments, the stripping gas can be inert under the dehydrogenation, dehydroaromatization, and dehydrocyclization, combustion, and/or reducing conditions. Suitable stripping fluids can be or can include, but are not limited to, molecular nitrogen ($N_2$), helium (He), argon (Ar), carbon dioxide ($CO_2$), steam ($H_2O$), methane ($CH_4$), or a mixture thereof. The stripping gas can be contacted with the coked catalyst particles, the regenerated catalyst particles, and/or the regenerated and reduced catalyst particles at a volume ratio of about 0.01 $m^3$ to 10 $m^3$ of stripping gas per cubic meter of catalyst particles.

In some embodiments, a riser configuration can be implemented in which the hydrocarbon-containing feed can be admixed with a dilution gas and contacted with heated and fluidized first catalyst particles within the first conversion zone disposed within the riser toward a first end of the riser. The dilution gas can be or can include, but is not limited to, molecular nitrogen, methane, steam, molecular hydrogen, or a mixture thereof. The combined gas can convect or otherwise convey the fluidized first catalyst particles through the first conversion zone while contacting and reacting as the mixture flows through the first conversion zone to produce the first conversion zone effluent that includes the upgraded hydrocarbons, molecular hydrogen, coked catalyst particles, and unconverted hydrocarbon-containing feed. The second catalyst particles can be fed into the second conversion zone disposed within the riser between the first conversion zone and a second end of the riser. The combined first conversion zone effluent, first catalyst, and second catalyst can convect or otherwise convey the fluidized first catalyst particles and the fluidized second catalyst particles through the second conversion zone while contacting and reacting as the mixture flows through the second conversion zone to produce the second conversion zone effluent that includes an additional quantity of upgraded hydrocarbons and molecular hydrogen. In this embodiment, one or more intermediate conversion zones can optional be disposed within the riser between the first conversion zone and the second conversion zone.

A residence time of the hydrocarbon-containing feed and the fluidized first catalyst particles within the first conversion zone can be sufficient to achieve a desired conversion of the hydrocarbon-containing feed to one or more upgraded hydrocarbons. A residence time of the first conversion zone effluent, the fluidized first catalyst particles, and the fluidized second catalyst particles within the second conversion zone can be sufficient to achieve a desired conversion of the unconverted hydrocarbon-containing feed to the additional upgraded hydrocarbon. The upgraded hydrocarbons and the fluidized first and second catalyst particles can be separated through the use of a gas-solid separation device, where the gas can be sent for recovery and the catalyst particles can be recovered. The specific design of the riser, including fabrication and dimensions, can be dependent, at least in part, on the intended chemistry, but typically can require velocities in excess of 4.5 m/s under average gas composition. To reduce thermal cracking of the hydrocarbon, the conversion effluent can be quenched via one or more of a number of different methods after desired conversion of the hydrocarbon-containing feed is achieved but before solid-gas separation. Such methods can include direct injection of a cooling medium such as steam into the second conversion zone effluent, passing the second conversion zone effluent through a heat exchanger, etc. The gaseous product after the gas-solid separation device can also be quenched using similar methods to avoid or reduce thermal cracking.

Some systems that can be modified to carry out the processes disclosed herein can include systems that are well-known in the art such as the fluidized reactors disclosed in U.S. Pat. Nos. 3,888,762; 7,102,050; 7,195,741; 7,122,160; and 8,653,317; U.S. Patent Application Publication Nos. 2004/0082824; 2008/0194891; and WO Publication Nos. WO2001/85872; WO2004/029178; and WO2005/077867.

Catalyst Particles

The first catalyst, the second catalyst, and any intermediate catalyst(s) can each include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of the Group 8-10 element, based on the total weight of the support. In some embodiments, the first catalyst, the second catalyst, and any intermediate catalyst(s) can include ≤5.5 wt %, ≤4.5 wt %, ≤3.5 wt %, ≤2.5 wt %, ≤1.5 wt %, ≤1 wt %, ≤0.9 wt %, ≤0.8 wt %, ≤0.7 wt %, ≤0.6 wt %, ≤0.5 wt %, ≤0.4 wt %, ≤0.3 wt %, ≤0.2 wt %, ≤0.15 wt %, ≤0.1 wt %, ≤0.09 wt %, ≤0.08 wt %, ≤0.07 wt %, ≤0.06 wt %, ≤0.05 wt %, ≤0.04 wt %, ≤0.03 wt %, ≤0.02 wt %, ≤0.01 wt %, ≤0.009 wt %, ≤0.008 wt %, ≤0.007 wt %, ≤0.006 wt %, ≤0.005 wt %, ≤0.004 wt %, ≤0.003 wt %, or ≤0.002 of the Group 8-10 element, based on the total weight of the support. In some embodiments, the first catalyst, the second catalyst, and any intermediate catalyst(s) can include >0.001, >0.003 wt %, >0.005 wt %, >0.007 wt %, >0.009 wt %, >0.01 wt %, >0.02 wt %, >0.04 wt %, >0.06 wt %, >0.08 wt %, >0.1 wt %, >0.13 wt %, >0.15 wt %, >0.17 wt %, >0.2 wt %, >0.2 wt %, >0.23, 0.25 wt %, >0.27 wt %, or >0.3 wt % and <0.5 wt %, <1 wt %, <2 wt %, <3 wt %, <4 wt %, <5 wt %, or <6 wt % of the Group 8-10 element based on the total weight of the support. In other embodiments, the first catalyst, the second catalyst, and any intermediate catalyst(s) can each include >0.025 wt %, >0.05 wt %, >0.1 wt %, >0.13 wt %, >0.15 wt %, >0.17 wt %, >0.2 wt %, >0.2 wt %, >0.23, >0.25 wt %, >0.27 wt %, or >0.3 wt % and <0.5 wt %, <1 wt %, <2 wt %, <3 wt %, <4 wt %, <5 wt %, or <6 wt % of the Group 8-10 element based on the total weight of the support.

In some embodiments, the Group 8-10 element can be or can include, but is not limited to, Fe, Co, Ni, Ru, Pd, Os, Ir, Pt, a combination thereof, or a mixture thereof. In at least one embodiment, the Group 8-10 element can be or can include Pt. If two or more Group 8-10 elements are disposed on the support, the first catalyst, the second catalyst, and any intermediate catalyst(s) can each include 0.001 wt %, 0.002 wt %, 0.003 wt %, 0.004 wt %, 0.005 wt %, 0.006 wt %, 0.007 wt %, 0.008 wt %, 0.009 wt %, 0.01 wt %, 0.015 wt %, 0.02 wt %, 0.025 wt %, 0.03 wt %, 0.035 wt %, 0.04 wt %, 0.045 wt %, 0.05 wt %, 0.055 wt %, 0.06 wt %, 0.065 wt %, 0.07 wt %, 0.075 wt %, 0.08 wt %, 0.085 wt %, 0.09 wt %, 0.095 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, 5 wt %, or 6 wt % of a combined amount of the two or more Group 8-10 elements disposed on the support, based on the weight of the total weight of the support.

The support in each of the first catalyst, the second catalyst, and any intermediate catalyst(s) can be or can include, but is not limited to, one or more elements having an atomic number of 4, 12, 20-22, 30, 38-40, 48, or 56-71. Said another way, the support in each of the first catalyst, the second catalyst, and any intermediate catalyst(s) can be or can include one or more Group 2 elements, one or more Group 4 elements, one or more Group 12 elements, one or more elements having an atomic number of 21, 39, or 57-71, combinations thereof, or mixture thereof. In some embodiments, the Group 2 element, the Group 4 element, the Group 12 element, and/or the element having an atomic number of 21, 39, or 57-71 can be present in its elemental form. In other embodiments, the Group 2 element, the Group 4 element, the Group 12 element, and/or the element having an atomic number of 21, 39, or 57-71 can be present in the form of a compound. For example, the Group 2 element, the Group 4 element, the Group 12 element, and/or the element having an atomic number of 21, 39, or 57-71 can be present as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, a mixture of any two or more compounds that include the Group 2 element, the Group 4 element, the Group 12 element, and/or the element having an atomic number of 21, 39, or 57-71 can be present in different forms. For example, a first compound can be an oxide and a second compound can be an aluminate where the first compound and the second compound include the same or different Group 2 element, Group 4 element, Group 12 element, and/or element having an atomic number of 21, 39, or 57-71, with respect to one another.

In some embodiments, the support in each of the first catalyst, the second catalyst, and any intermediate catalyst(s) can be or can include at least one of: w wt % of the one or more Group 2 elements, x wt % of the one or more Group 4 elements, y wt % of the one or more Group 12 elements, and z wt % of the one or more elements having an atomic number of 21, 39, or 57-71 based on the weight of the support, where w, x, y, and z are independently in a range from 0 to 100, and where w+x+y+z is <100. Any Group 2 element present in the support in each of the first catalyst, the second catalyst, and any intermediate catalyst(s) can be associated with a wt % m based on the weight of the support, any Group 4 element present in the support in each of the first catalyst, the second catalyst, and any intermediate catalyst(s) can be associated with a wt % n based on the weight of the support, any Group 12 element present in the support in each of the first catalyst, the second catalyst, and any intermediate catalyst(s) can be associated with a wt % p based on the weight of the support, and any element having an atomic number of 21, 39, or 57-71 present in the support in each of the first catalyst, the second catalyst, and any intermediate catalyst(s) can be associated with a wt % q based on the weight of the support, where m, n, p, and q can independently be a number that is in a range from 1 to 100. In some embodiments, m, n, p, and q can each be equal to 1, 2, 15, or 30, or m can be equal to 1, n can be equal to 15, p can be equal to 15, and q can be equal to 1.

As used herein, "m" represents the minimum wt % of all Group 2 elements in the support, if none of the Group 4 elements, none of the Group 12 elements, and none of the elements having an atomic number of 21, 39, or 57-71 are present in the support. Similarly, as used herein, "n" represents the minimum wt % of all Group 4 elements in the support, if none of the Group 2 elements, none of the Group 12 elements, and none of the elements having an atomic number of 21, 39, or 57-71 are present in the support. Similarly, "p" represents the minimum wt % of all Group 12 elements in the support, if none of the Group 2 elements, none of the Group 4 elements, and none of the elements having an atomic number of 21, 39, or 57-71 are present in the support, Finally, "q" represents the minimum wt % of all elements having an atomic number of 21, 39, or 57-71 that are present in the support, if none of the Group 2 elements, none of the Group 4 elements, and none of the Group 12 elements are present in the support.

In some embodiments, a sum of $w/m+x/n+y/p+z/q$ can be at least 1, based on the weight of the support in each of the first catalyst, the second catalyst, and any intermediate catalyst(s). In other embodiments, a sum of $w/m+x/n+y/p+z/q$ can be at least 1, at least 2, at least 4, at least 6, at least 8, at least 12, at least 24, at least 48, or at least 60, based on the weight of the support in each of the first catalyst, the second catalyst, and any intermediate catalyst(s). In other embodiments, a sum of $w/m+x/n+y/p+z/q$ can be in a range from 1, 2, 3, 4, 5, 6, 7, or 8 to 10, 12, 16, 24, 30, 48, or 60. In other embodiments, a sum of $w/m+x/n+y/p+z/q$ can be in a range from 1 to 2, 2 to 4, 4 to 6, 6 to 8, 8 to 12, 12 to 24, 24 to 48, or 48 to 60.

As such, the m, n, p, and q not only specify the minimum amount of each group of elements present in the support when the other groups of elements are not present in the support, but also specify the minimum amount of each group of elements in the support when any one or more of the other groups of elements are also present in the support, which is explained by the following Example.

In this Example: m=4, n=8, p=12, q=20. If none of the Group 4 elements, none of the Group 12 elements, and none of the elements having an atomic number of 21, 39, or 57-71 are present in the support, then the total amount of any Group 2 element(s) in the support has to be ≥4 wt %, i.e., $w/m \geq 1$. If none of the Group 2 elements, none of the Group 12 elements, and none of the elements having an atomic number of 21, 39, or 57-71 are present in the support, then the total amount of any Group 4 element(s) present in the support has to be ≥8 wt %, i.e., $x/n \geq 1$. If none of the Group 2 elements, none of the Group 4 elements, and none of the elements having an atomic number of 21, 39, or 57-71 are present in the support, then the total amount of any Group 12 element(s) present in the support has to be ≥12 wt %, i.e., $y/p \geq 1$. If none of the Group 2 elements, none of the Group 4 elements, and none of the Group 12 elements exist on the support, then the total amount of any element(s) having an atomic number of 21, 39, or 57-71 present in the support has to be ≥20 wt %, i.e., $z/q \geq 1$.

If both Group 2 and 4 elements are present in the support and none of the Group 12 elements and none of the elements having an atomic number of 21, 39, or 57-71 are present in the support, then there is no need for the total amount of Group 2 element(s) to be ≥4 wt % since the Group 4 element(s) on the support share the role of the Group 2 element(s). Similarly, there is no need for the total amount of Group 4 element(s) to be ≥8 wt % since the Group 2 element(s) on the support share the role of the Group 4 element(s). Such an interchangeable relationship between the Group 2 and 4 elements is defined by m and n. Since m=4 and n=8, two mass units of the Group 4 element(s) interchanges one mass unit of the Group 2 element(s). For example, if the total amount of the Group 2 element(s) is w=1.1 wt % and the total amount of the Group 4 element(s) is x=4.3 wt %, then w/m+x/n=1.1/4+4.3/8=0.8125, which is <1, i.e., the total amount of the Group 2 and 4 elements is too little for the support to satisfy $w/m+x/n+y/p+z/q$ is ≥1. In another example, if the total amount of the Group 2 element(s) is w=2.4 wt % and the total amount of the Group 4 element(s) is x=4.3 wt %, then w/m+x/n=2.4/4+4.3/8=1.1375, which is ≥1, such that the total amount of the Group 2 and Group 4 elements is sufficient to satisfy $w/m+x/n+y/p+z/q$ is ≥1, despite that both w and x (2.4 and 4.3) are less than m and n (4 and 8), respectively.

The same principle also applies to cases when the support includes at least one element from three of the group of elements, e.g., Group 2, Group 4, and Group 12, as well as when the support includes each group of elements, i.e., at least one Group 2 element, at least one Group 4 element, at least one Group 12 element, and at least one element having an atomic number of 21, 39, or 57-71. For example, if the support includes 0.5 wt % of Mg (Group 2 element), 2 wt % of Ca (Group 2 element), 4 wt % of Ce (atomic number of 58), 3 wt % of Zr (Group 4 element), and 6 wt % of Zn (Group 12 element), then the equation would be: (0.5+2)/4+4/20+3/8+6/12=1.7, which is >1. In summary, m, n, p, and q is the minimum amount of each Group of elements in the support when the other Groups of elements are not present in the support. The equation $w/m+x/n+y/p+z/q \geq 1$ defines how the 4 groups of elements can work together in the support.

In some embodiments, m can be one of ten values selected from: 2, 4, 6, 8, 10, 12, 14, 16, 18, and 20; n can be one of twelve values selected from: 2, 4, 6, 8, 10, 12, 14, 16, 18, 20, 22, and 24; p can be one of twelve values selected from: 2, 4, 6, 8, 10, 12, 14, 16, 18, 20, 22, and 24; and q can be one of twelve values selected from: 2, 4, 6, 10, 14, 18, 22, 26, 30, 34, 38, and 40, where m, n, p, and q can be any combination such that there are 17,280 (10×12×12×12) distinct combinations. In other embodiments, m can be equal to 2, 7, 10, or 20, n can be 2, 10, 20, or 25, p can be 2, 10, 20, or 25, and q can be 2, 10, 30, or 40, where m, n, p, and q can be any combination such that there are 256 (4×4×4×4) distinct combinations. In some embodiments, m, n, p, and q can each be equal to 2, 10, 15, or 30. In other embodiments, m can be equal to 7, n can be equal to 10, p can be equal to 10, and q can be equal to 10. In other embodiments, m can be equal to 7, n can be equal to 20, p can be equal to 20, and q can be equal to 10. In other embodiments, m can be equal to 10, n can be equal to 20, p can be equal to 20, and q can be equal to 30. In other embodiments, m can be equal to 7, n can be equal to 10, p can be equal to 10, and q can be equal to 30.

In some embodiments, w, x, y, and z can independently be 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100, where a sum of w, x, y, z is ≤100.

In some embodiments, when the support in the first catalyst, the second catalyst, and/or any intermediate catalyst(s) includes the Group 2 element, a molar ratio of the Group 2 element to the Group 8-10 element can be in a range from 0.24, 0.5, 1, 10, 50, 100, 300, 450, 600, 800, 1,000, 1,200, 1,500, 1,700, or 2,000 to 3,000, 3,500, 4,000, 4,500, 5,000, 5,500, 6,000, 6,500, 7,000, 7,500, 8,000, 8,500, 9,000, 9,500, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 200,000, 300,000, 400,000, 500,000, 600,000, 700,000, 800,000, or 900,000. In some embodiments, when the support in the first catalyst, the second catalyst, and/or any intermediate catalyst(s) includes the Group 4 element, a molar ratio of the Group 4 element to the Group 8-10 element can be in a range from 0.18, 0.3, 0.5, 1, 10, 50, 100, 200, 300, 400, 500, 600, 700, 810, 1,000, or 5,000 to 10,000, 20,000, 30,000, 40,000, 50,000, 60,000, 70,000, or 81,000. In some embodiments, when the support in the first catalyst, the second catalyst, and/or any intermediate catalyst(s) includes the Group 12 element, a molar ratio of the Group 12 element to the Group 8-10 element can be in a range from 0.29, 0.5, 1, 10, 50, or 100 to 200, 300, 400, 500, 590, 600, or 1,000 to 5,000, 10,000, 20,000, 30,000, 40,000, 50,000 or 59,000. In some embodiments, when the support in the first catalyst, the second catalyst, and/or any intermediate catalyst(s) includes the element having an atomic number of 21, 39, or 57-71, a molar ratio of the element having an atomic number of 21, 39, or 57-71 to the Group 8-10 element can be in a range from 0.19, 0.5, 1, 10, 50, 100, or 150 to 200, 250, 300, 350, 400, 438, 500, 750, or 1,000 to 5,000, 10,000, 20,000, 30,000, 40,000, or 43,800. In some embodiments, when the support in the first catalyst, the second catalyst, and/or any intermediate catalyst(s) includes two or more of the Group 2, 4, or 12 element and the element having an atomic number of 21, 39, or 57-71, a molar ratio of a combined amount of any Group 2 element, any Group 4 element, any Group 12 element, and any element having an atomic number of 21, 39, or 57-71 to the Group 8-10 element can be in a range from 0.18, 0.5, 1, 10, 50, 100, 300, 450, 600, 800, 1,000, 1,200, 1,500, 1,700, or 2,000 to 3,000, 3,500, 4,000, 4,500, 5,000, 5,500, 6,000, 6,500, 7,000, 7,500, 8,000, 8,500, 9,000, 9,500, 10,000, 15,000, 20,000, 25,000, 30,000, 35,000, 40,000, 43,800, 45,000, 50,000, 55,000, 59,000, 60,000, 65,000, 70,000, 75,000, 80,000, 81,000, 85,000, 90,000, 95,000, 100,000, 200,000, 300,000, 400,000, 500,000, 600,000, 700,000, 800,000, or 900,000.

In some embodiments, the support in the first catalyst, the second catalyst, and/or any intermediate catalyst(s) can be or can include, but is not limited to, one or more of the following compounds: $Mg_uZn_{1-u}O$, where u is a positive number; $Zn_vAl2O3_{+v}$, where v is a positive number; $Mg_wAl_2O_{3+w}$, where w is a positive number; $Ca_xAl_2O_{3+x}$, where x is a positive number; $Sr_yAl_2O_{3+y}$, where y is a positive number; $Ba_zAl_2O_{3+z}$, where z is a positive number. BeO; MgO; CaO; BaO; SrO; $BeCO_3$; $MgCO_3$; $CaCO_3$; $SrCO_3$; $BaCO_3$; $ZrO_2$; ZrC; ZrN; $ZrSiO_4$; $CaZrO_3$; $Ca_7ZrAl_6I_{18}$; $TiO_2$; TiC; TiN; $TiSiO_4$; $CaTiO_3$; $Ca_7Al_6O_{18}$; $HfO_2$; HfC; HfN; $HfSiO_4$; $HfZrO_3$; $Ca_7HfAl_6O_{18}$; ZnO; $Zn_3(PO_4)_2$; $Zn(ClO_3)_2$; $ZnSO_4$; $B_2O_6Zn_3$; $Zn_3N_2$; $ZnCO_3$; $CeO_2$; $Y_2O_3$; $La_2O_3$; $Sc_2O_3$; $Pr_6O_{11}$; $CePO_4$; $CeZrO_4$; $CeAlO_3$; $BaCeO_3$; $CePO_4$; Yttria-stabilized $ZrO_2$; one or more magnesium chromates, one or more magnesium tungstates, one or more magnesium molybdates combinations thereof, and mixtures thereof.

The $Mg_uZn_{1-u}O$, where u is a positive number, if present as the support or as a component of the support in the first catalyst, the second catalyst, and/or any intermediate catalyst(s) can have a molar ratio of Mg to Zn in a range from 1, 2, 3, or 6 to 12, 25, 50, or 100. The $Zn_vAl2O3_{+v}$, where v is a positive number, if present as the support or as a component of the support in the first catalyst, the second catalyst, and/or any intermediate catalyst(s) can have a molar ratio of Zn to Al in a range from 0.05, 0.3, or 0.6 to 0.9, 1.5, or 3 The $Mg_wAl_2O_{3+w}$, where w is a positive number, if present as the support or as a component of the support in the first catalyst, the second catalyst, and/or any intermediate catalyst(s) can have a molar ratio of Mg to Al in a range from 1, 2, 3, 4, or 5 to 6, 7, 8, 9, or 10. The $Ca_xAl_2O_{3+x}$, where x is a positive number, if present as the support or as a component of the support in the first catalyst, the second catalyst, and/or any intermediate catalyst(s) can have a molar ratio of Ca to Al in a range from 1:12, 1:4, 1:2, 2:3, 5:6, 1:1, 12:14, or 1.5:1. In some embodiments, the $Ca_xAl_2O_{3+x}$, can include tricalcium aluminate, dodecacalcium hepta-aluminate, moncalcium aluminate, moncalcium dialuminate, monocalcium hexa-aluminate, dicalcium aluminate, pentacalcium trialuminate, tetracalcium trialuminate, or any mixture thereof. The $Sr_yAl_2O_{3+y}$, where y is a positive number, if present as the support or as a component of the support in the first catalyst, the second catalyst, and/or any intermediate catalyst(s) can have a molar ratio of Sr to Al in a range from 0.05, 0.3, or 0.6 to 0.9, 1.5, or 3. The $Ba_zAl_2O_{3+z}$, where z is a positive number, if present as the support or as a component of the support in the first catalyst, the second catalyst, and/or any intermediate catalyst(s) can have a molar ratio of Ba to Al 0.05, 0.3, or 0.6 to 0.9, 1.5, or 3.

In some embodiments, the support in the first catalyst, the second catalyst, and/or any intermediate catalyst(s) can also include, but is not limited to, at least one metal element and/or at least one metalloid element selected from Groups 5, 6, 7, 11, 13, 14, 15, and 16 and/or at least one compound thereof. If the support in the first catalyst, the second catalyst, and/or any intermediate catalyst(s) also includes a compound that includes the metal element and/or metalloid element selected from Groups 5, 6, 7, 11, 13, 14, 15, and 16, the compound can be present in the support as an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide. In some embodiments, suitable compounds that include the metal element and/or metalloid element selected from Groups 5, 6, 7, 11, 13, 14, 15, and 16 can be or can include, but are not limited to, one or more of the following: $B_2O_3$, $AlBO_3$, $Al_2O_3$, $SiO_2$, SiC, $Si_3N_4$, an aluminosilicate, VO, $V_2O_3$, $VO_2$, $V_2O_5$, $Ga_2O_3$, $In_2O_3$, $Mn_2O_3$, $Mn_3O_4$, MnO, one or more molybdenum oxides, one or more tungsten oxides, one or more zeolites, and mixtures and combinations thereof.

In some embodiments, the support in the first catalyst, the second catalyst, and/or any intermediate catalyst(s) can include the Group 2 element and Al and can be in the form of a mixed Group 2 element/Al metal oxide that has O, Mg, and Al atoms mixed on an atomic scale. In some embodiments the support in the first catalyst, the second catalyst, and/or any intermediate catalyst(s) can be or can include the Group 2 element and Al in the form of an oxide or one or more oxides of the Group 2 element and $Al_2O_3$ that can be mixed on a nm scale. In some embodiments, the support in the first catalyst, the second catalyst, and/or any intermediate catalyst(s) can be or can include an oxide of the Group 2 element, e.g., MgO, and $Al_2O_3$ mixed on a nm scale. In some embodiments, the support in the first catalyst, the second catalyst, and/or any intermediate catalyst(s) can be produced by calcining hydrotalcite.

In some embodiments, the support in the first catalyst, the second catalyst, and/or any intermediate catalyst(s) can be or can include a first quantity of the Group 2 element and Al in the form of a mixed Group 2 element/Al metal oxide and a second quantity of the Group 2 element in the form of an oxide of the Group 2 element. In such embodiment, the mixed Group 2 element/Al metal oxide and the oxide of the Group 2 element can be mixed on the nm scale and the Group 2 element and Al in the mixed Group 2 element/Al metal oxide can be mixed on the atomic scale.

In other embodiments, the support in the first catalyst, the second catalyst, and/or any intermediate catalyst(s) can be or can include a first quantity of the Group 2 element and a first quantity of Al in the form of a mixed Group 2 element/Al metal oxide, a second quantity of the Group 2 element in the form of an oxide of the Group 2 element, and a second quantity of Al in the form of $Al_2O_3$. In such embodiment, the mixed Group 2 element/Al metal oxide, the oxide of the Group 2 element, and the $Al_2O_3$ can be mixed on a nm scale and the Group 2 element and Al in the mixed Group 2 element/Al metal oxide can be mixed on the atomic scale.

In some embodiments, when the support in the first catalyst, the second catalyst, and/or any intermediate catalyst(s) includes the Group 2 element and Al, a weight ratio of the Group 2 element to the Al in the support can be in a range from 0.001, 0.005, 0.01, 0.05, 0.1, 0.15, 0.2, 0.3, 0.5, 0.7, or 1 to 3, 6, 12.5, 25, 50, 75, 100, 200, 300, 400, 500, 600, 700, 800, 900, or 1,000. In some embodiments, when the support in the first catalyst, the second catalyst, and/or any intermediate catalyst(s) includes Al, the support can include Al in a range from 0.5 wt %, 1 wt %, 1.5 wt %, 2 wt %, 2.1 wt %, 2.3 wt %, 2.5 wt %, 2.7 wt %, 3 wt %, 4 wt %, 5 wt %, 6 wt %, 7 wt %, 8 wt %, 9 wt %, 10 wt %, or 11 wt % to 15 wt %, 20 wt %, 25 wt %, 30 wt %, 40 wt %, 45 wt %, or 50 wt %, based on the weight of the support.

In some embodiments, the support in the first catalyst, the second catalyst, and/or any intermediate catalyst(s) can include ≥3 wt %, ≥6 wt %, ≥11 wt %, ≥15 wt %, ≥20 wt %, ≥25 wt %, ≥, 30 wt %, or ≥ of a Group 2 element based on the weight of the support. In some embodiments, the Group 2 element can be or can include, but is not limited to, Mg. In some embodiments, the support in the first catalyst, the second catalyst, and/or any intermediate catalyst(s) can be or can include, but is not limited to, calcined hydrotalcite.

In some embodiments, the support in the first catalyst, the second catalyst, and/or any intermediate catalyst(s) can also include one or more promoters disposed thereon. The promoter can be or can include, but is not limited to, Sn, Ga, Zn, Ge, In, Re, Ag, Au, Cu, a combination thereof, or a mixture thereof. As such, the promoter if present as a component of the first catalyst, the second catalyst, and/or any intermediate catalyst(s), can be present as a component of the support, as a promoter disposed on the support, or both as a component of the support and as a promoter disposed on the support. In some embodiments, the promoter can be associated with the Group 8-10 element, e.g., Pt. For example, the promoter and the Group 8-10 element disposed on the support in the first catalyst, the second catalyst, and/or any intermediate catalyst(s) can form Group-8-10 element-promoter clusters that can be dispersed on the support. The promoter, if present, can improve the selectivity/activity/longevity of the catalyst for a given upgraded hydrocarbon. In some embodiments, the addition of the promoter can improve the propylene selectivity of the catalyst particles when the hydrocarbon-containing feed includes propane. The first catalyst, the second catalyst, and/or any intermediate catalyst(s) can include the promoter in an amount of 0.01 wt %, 0.05 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 3 wt %, 5 wt %, 7 wt %, or 10 wt %, based on the weight of the support.

In some embodiments, the support in the first catalyst, the second catalyst, and/or any intermediate catalyst(s) can also include one or more alkali metal elements disposed on the support. The alkali metal element, if present, can be or can include, but is not limited to, Li, Na, K, Rb, Cs, a combination thereof, or a mixture thereof. In at least some embodiments, the alkali metal element ca be or can include K and/or Cs. The alkali metal element, if present, can improve the selectivity of the catalyst particles for a given upgraded hydrocarbon. The first catalyst, the second catalyst, and/or any intermediate catalyst(s) can include the alkali metal element in an amount 0.01 wt %, 0.05 wt %, 0.1 wt %, 0.2 wt %, 0.3 wt %, 0.4 wt %, 0.5 wt %, 0.6 wt %, 0.7 wt %, 0.8 wt %, 0.9 wt %, or 1 wt % to 2 wt %, 3 wt %, 4 wt %, or 5 wt %, based on the weight of the support.

Catalyst Preparation

The preparation of the support of the first catalyst, the second catalyst, and/or any intermediate catalyst(s) can be accomplished via any known process. For simplicity and ease of description, the preparation of a suitable support that includes a mixed oxide of magnesium and aluminum (Mg (Al)O or $MgO/Al_2O_3$) will be described in more detail. Catalyst synthesis techniques are well-known and the following description is for illustrative purposes and not to be considered as limiting the synthesis of the support or any of the first catalyst, the second catalyst, and/or any intermediate catalyst(s). In some embodiments, to make the $MgO/Al_2O_3$ mixed oxide support, Mg and Al precursors such as $Mg(NO_3)_2$ and $Al(NO_3)_3$ can be mixed together, e.g., ball-milled, followed by calcination to produce the support. In another embodiment, the two precursors can be dissolved in $H_2O$, stirred until dry (with heat optionally applied), followed by calcination to produce the support. In another embodiment, the two precursors can be dissolved in $H_2O$, followed by the addition of a base and a carbonate, e.g., $NaOH/Na_2CO_3$ to produce hydrotalcite, followed by calcination to produce the support. In another embodiment, a commercial ready MgO and $Al_2O_3$ may be mixed and ball-milled. In another embodiment, the $Mg(NO_3)_2$ precursor can be dissolved in $H_2O$ and the solution can be impregnated onto an existing support, e.g., an $Al_2O_3$ support, that can be dried and calcined to produce the support. In another embodiment, Mg from $Mg(NO_3)_2$ can be loaded onto an existing $Al_2O_3$ support through ion adsorption, followed by liquid-solid separation, drying and calcination to produce the support. Without wishing to be bound by theory, it is believed that the support in the first catalyst, the second catalyst, and/or any intermediate catalyst(s) produced via any one of the above methods and/or other methods can include (i) the Mg and Al mixed together on the nm scale, (ii) the Mg and Al in the form of a mixed Mg/Al metal oxide, or (iii) a combination of (i) and (ii).

Group 8-10 metals and any promoter and/or any alkali metal element may be loaded onto the mixed oxide support by any known technique. For example, one or more Group 8-10 element precursors, e.g., chloroplatinic acid, tetramineplatinum(II) nitrate, and/or tetramineplatinum(II) hydroxide, one or more promoter precursors (if used), e.g., a salt such as $SnCl_4$ and/or $AgNO_3$, and one or more alkali metal element precursors (if used), e.g., $KNO_3$, KCl, and/or NaCl, can be dissolved in water. In some embodiments, the Group 8-10 element precursor can be or can include, but is not limited to, chloroplatinic acid hexahydrate, tetramineplatinum(II) nitrate, platinum(II) oxalate, platinum(II) acetylacetonate, platinum(II) bromide, platinum(II) iodide, platinum(II) chloride, platinum(IV) chloride, platinum(II) diammine dichloride, ammonium tetrachloroplatinate(II), tetraammineplatinum(II) chloride hydrate, tetraammineplatinum(II) hydroxide hydrate, iron nitrate, rhodium(III) nitrate, ruthenium(III) nitrate, cobalt(II) nitrate hexahydrate, nickel(II) nitrate hexahydrate, palladium(II) nitrate dihydrate, or any mixture thereof. In some embodiments, the promoter precursor can be or can include, but is not limited to, tin(II) oxide, tin(IV) oxide, tin(IV) chloride pentahydrate, tin(II) chloride dihydrate, tin citrate, tin sulfate, tin oxalate, tin(II) bromide, tin(IV) bromide, tin(II) acetylacetonate, tin(II) acetate, tin(IV) acetate, silver(I) nitrate, gold(III) nitrate, copper(II) nitrate, gallium(III) nitrate, or any mixture thereof. In some embodiments, the alkali metal element precursor can be or can include, but is not limited to, lithium nitrate, sodium nitrate, potassium nitrate, rubidium nitrate, cesium nitrate, or any mixture thereof.

The solution can be impregnated onto the support, followed by drying and calcination to produce the catalyst. In some embodiments, the Group 8-10 element precursor and optionally the promoter precursor and/or the alkali metal element precursor can be loaded onto the support at the same time, or separately in a sequence separated by drying and/or calcination steps to produce the catalyst. In other embodiments, the Group 8-10 element and, optionally the promoter and/or alkali metal element, can be loaded onto the support by chemical vapor deposition, where the precursors are volatilized and deposited onto the support, followed by calcination to produce the catalyst. In other embodiments, the Group 8-10 element precursor and, optionally, the promoter precursor and/or alkali metal precursor, can be loaded onto the support through ion adsorption, followed by liquid-solid separation, drying and calcination to produce the catalyst. Optionally, the first catalyst, the second catalyst, and/or any intermediate catalyst(s) can also be synthesized using a one-pot synthesis method where the precursors of the support, Group 8-10 metal active phase and the promoters are all mixed together, dry or wet, with or without any other additives to aid the synthesis, followed by drying or spray drying and calcination to produce the catalyst. In some embodiments, the drying or calcination may be carried out in an oxidative environment, or a reductive environment, or an inert environment, or a combination of two or more of the environments. In some embodiments, a suitable oxidative environment can be provided by air, enriched air, $O_2$, $O_2$ diluted by one or more inert gases, $O_3$, $O_3$ diluted by one or more inert gases, or any mixture thereof. In some embodiments, a suitable reductive environment can be provided by $H_2$, CO, syngas, or any reductive gas diluted by one or more inert gases. In some embodiments, a suitable inert environment can be provided by steam, $N_2$, Ar, He, or any mixture of the above. While drying/calcination is typically accompanied by the release of one or more volatiles, in some embodiments, the drying/calcination step can be preceded by an equilibration step where no release of volatiles is expected.

Suitable processes that can be used to prepare the first catalyst, the second catalyst, and/or any intermediate catalyst(s) disclosed herein can include the processes described in U.S. Pat. Nos. 4,788,371; 4,962,265; 5,922,925; 8,653, 317; EP Patent No. EP0098622; Journal of Catalysis 94 (1985), pp. 547-557; and/or Applied Catalysis 54 (1989), pp. 79-90.

The as-synthesized first catalyst, second catalyst, and/or any intermediate catalyst(s), when examined under scanning electron microscope or transmission electron microscope, can appear as either primary particles, as agglomerates of primary particles, as aggregates of primary particles, or a combination thereof. Primary particles, agglomerates of primary particles and aggregates of primary particles are described in Powder Technology 181 (2008) 292-300. The primary particles in the as-synthesized first catalyst, second catalyst, and/or any intermediate catalyst(s), when examined under scanning electron microscope or transmission electron microscope, can have an average cross-sectional length or average particle size, e.g., a diameter when spherical, in a range from 0.2 nm, 0.5 nm, 1 nm, 5 nm, 10 nm, 25 nm, 30 nm, 40 nm 50 nm, 60 nm, 70 nm, 80 nm, 90 nm, 100 nm, 150 nm, 200 nm, 250 nm, 300 nm, 350 nm, 400 nm, 450 nm, or 500 nm to 1 µm, 10 µm, 25 µm, 50 µm, 100 µm, 150 µm, 200 µm, 250 µm, 300 µm, 400 µm, or 500 µm. In some embodiments, the primary particles in the as-synthesized first catalyst, second catalyst, and/or any intermediate catalyst(s) can have an average particle size of 0.2 nm to 500 µm, 0.5 nm to 300 µm, 1 nm to 200 µm, 2 nm to 100 µm, 2 nm to 500 nm, or 2 nm to 100 nm, as measured by a transmission electron microscope.

The as-synthesized first catalyst, second catalyst, and/or any intermediate catalyst(s) can have a surface area in a range from 0.1 $m^2/g$, 1 $m^2/g$, 10 $m^2/g$, or 100 $m^2/g$ to 500 $m^2/g$, 800 $m^2/g$, 1,000 $m^2/g$, or 1,500 $m^2/g$. The surface area of the first catalyst, the second catalyst, and/or any intermediate catalyst(s) can be measured according to the Brunauer-Emmett-Teller (BET) method using adsorption-desorption of nitrogen (temperature of liquid nitrogen, 77 K) with a Micromeritics 3flex instrument after degassing of the powders for 4 hours at 350° C. More information regarding the method can be found, for example, in "Characterization of Porous Solids and Powders: Surface Area, Pore Size and Density," S. Lowell et al., Springer, 2004.

The as-synthesized first catalyst, second catalyst, and/or any intermediate catalyst(s) can be formulated into one or more appropriate forms for different short cycle (≤3 hours) hydrocarbon upgrading processes. Alternatively, the support of in the first catalyst, the second catalyst, and/or any intermediate catalyst(s) can be formulated into appropriate forms for different short cycle hydrocarbon upgrading processes, before the addition of the Group 8-10 element and, any optional promoter and/or alkali metal element. During formulation, one or more binders and/or additives can be added to the first catalyst, the second catalyst, and/or any intermediate catalyst(s) and/or support to improve the chemical/physical properties of the first catalyst, the second catalyst, and/or any intermediate catalyst(s) ultimately produced and used in the process. The binder/additives can be or can include, but are not limited to, silica, silica sol, silica-alumina, alumina, aluminum chlorhydrol, peptized alumina, aluminosilicates, smectites, kaolins, acid-treated metakaolins, illites, chlorites, attapulgites, pillared interlayered clays and mixed layer clays, silanes, alkoxysilanes, aryloxysilanes, acyloxysilanes, oximinosilanes, halo silanes aminoxysilanes, aminosilanes, amidosilanes, silazanes, silicones, or a mixture thereof.

In some embodiments, the first catalyst, the second catalyst, and/or any intermediate catalyst(s) can be formulated via the well-known spray drying process to produce spray dried catalyst particles. Spray-dried catalyst particles having an average cross-sectional area in a range from 20 µm, 40 µm, or 50 µm to 80 µm, 90 µm, or 100 µm are typically used in an FCC type fluid-bed reactor. To make spray-dried catalyst particles, the support, the Group 8-10 element, and any additional components, e.g., the promoter and/or the alkali metal, can be made into a slurry with binder/additive in the slurry before spray-drying and calcination. Alternatively, the Group 8-10 element, and any additional components, e.g., the promoter and/or the alkali metal, can be added to the formulated support to produce the formulated catalyst.

In some embodiments, the formulated first catalyst, second catalyst, and/or any intermediate catalyst(s) can have a particle density in a range from 0.5 g/cm$^3$, 0.7 g/cm$^3$, 0.9 g/cm$^3$, 1 g/cm$^3$, 1.2 g/cm$^3$, or 1.3 g/cm$^3$, to 1.5 g/cm$^3$, 1.8 g/cm$^3$, 2 g/cm$^3$, 2.3 g/cm$^3$, 2.5 g/cm$^3$, 2.7 g/cm$^3$, or 3 g/cm$^3$. The "particle density" refers to the density of the catalyst particles including the pore volume in g/cm$^3$ and can be measured by mercury porosimetry. The particle density of the catalyst particles can be measured according to UOP578-11. In some embodiments, the catalyst particles can have an average particle size and particle density consistent with a Geldart A definition.

Hydrocarbon-Containing Feed

The $C_2$-$C_{16}$ alkanes can be or can include, but are not limited to, ethane, propane, n-butane, isobutane, n-pentane, isopentane, n-hexane, 2-methylpentane, 3-methylpentane, 2,2-dimethylbutane, n-heptane, 2-methylhexane, 2,2,3-trimethylbutane, cyclopentane, cyclohexane, methylcyclopentane, ethylcyclopentane, n-propylcyclopentane, 1,3-dimethylcyclohexane, or a mixture thereof. For example, the hydrocarbon-containing feed can include propane, which can be dehydrogenated to produce propylene, and/or isobutane, which can be dehydrogenated to produce isobutylene. In another example, the hydrocarbon-containing feed can include liquid petroleum gas (LP gas), which can be in the gaseous phase when contacted with the catalyst particles. In some embodiments, the hydrocarbon in the hydrocarbon-containing feed can be composed of substantially a single alkane such as propane. In some embodiments, the hydrocarbon-containing feed can include ≥50 mol %, ≥75 mol %, ≥95 mol %, ≥98 mol %, or ≥99 mol % of a single $C_2$-$C_{16}$ alkane, e.g., propane, based on a total weight of all hydrocarbons in the hydrocarbon-containing feed. In some embodiments, the hydrocarbon-containing feed can include at least 50 vol %, at least 55 vol %, at least 60 vol %, at least 65 vol %, at least 70 vol %, at least 75 vol %, at least 80 vol %, at least 85 vol %, at least 90 vol %, at least 95 vol %, at least 97 vol %, or at least 99 vol % of a single $C_2$-$C_{16}$ alkane, e.g., propane, based on a total volume of the hydrocarbon-containing feed.

The $C_8$-$C_{16}$ alkyl aromatic hydrocarbons can be or can include, but are not limited to, ethylbenzene, propylbenzene, butylbenzene, one or more ethyl toluenes, or a mixture thereof. In some embodiments, the hydrocarbon-containing feed can include ≥50 mol %, ≥75 mol %, ≥95 mol %, ≥98 mol %, or ≥99 mol % of a single $C_8$-$C_{16}$ alkyl aromatic, e.g., ethylbenzene, based on a total weight of all hydrocarbons in the hydrocarbon-containing feed. In some embodiments, the ethylbenzene can be dehydrogenated to produce styrene. As such, in some embodiments, the processes disclosed herein can include propane dehydrogenation, butane dehydrogenation, isobutane dehydrogenation, pentane dehydrogenation, pentane dehydrocyclization to cyclopentadiene, naphtha reforming, ethylbenzene dehydrogenation, ethyltoluene dehydrogenation, and the like.

In some embodiments, the hydrocarbon-containing feed can be diluted with one or more diluent gases. Suitable diluents can be or can include, but are not limited to, argon, neon, helium, molecular nitrogen, carbon dioxide, methane, molecular hydrogen, or a mixture thereof. If the hydrocarbon containing-feed includes a diluent, the hydrocarbon-containing feed can include 0.1 vol %, 0.5 vol %, 1 vol %, or 2 vol % to 3 vol %, 8 vol %, 16 vol %, or 32 vol % of the diluent, based on a total volume of any $C_2$-$C_{16}$ alkanes and any $C_8$-$C_{16}$ alkyl aromatic hydrocarbons in the hydrocarbon-containing feed. When the diluent includes molecular hydrogen, a molar ratio of the molecular hydrogen to a combined amount of any $C_2$-$C_{16}$ alkane and any $C_8$-$C_{16}$ alkyl aromatic hydrocarbons can be in a range from 0.1, 0.3, 0.5, 0.7, or 1 to 2, 3, 4, 5, 6, 7, 8, 9, or 10. In some embodiments, if the diluent is used, the diluent can be mixed with the hydrocarbon-containing feed and/or introduced or otherwise fed into the conversion zone as a separate feed via one or more inlets dedicated to feeding the diluent into the conversion zone. Similarly, the hydrocarbon-containing feed can also be introduced into the conversion zone via one or more inlets dedicated to feeding the hydrocarbon-containing feed into the conversion zone.

In some embodiments, the hydrocarbon-containing feed can be substantially free of any steam, e.g., <0.1 vol % of steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include steam. For example, the hydrocarbon-containing feed can include 0.1 vol %, 0.3 vol %, 0.5 vol %, 0.7 vol %, 1 vol %, 3 vol %, or 5 vol % to 10 vol %, 15 vol %, 20 vol %, 25 vol %, 30 vol %, 35 vol %, 40 vol %, 45 vol %, or 50 vol % of steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include ≤50 vol %, ≤45 vol %, ≤40 vol %, ≤35 vol %, ≤30 vol %, ≤25 vol %, ≤20 vol %, ≤15 vol % of steam, based on a total volume of any $C_2$-$C_{16}$ alkanes and any $C_8$-$C_{16}$ alkyl aromatic hydrocarbons in the hydrocarbon-containing feed. In other embodiments, the hydrocarbon-containing feed can include at least 1 vol %, at least 3 vol %, at least 5 vol %, at least 10 vol %, at least 15 vol %, at least 20 vol %, at least 25 vol %, or at least 30 vol % of steam, based on a total volume of any $C_2$-$C_{16}$ alkanes and any $C_8$-$C_{16}$ alkyl aromatic hydrocarbons in the hydrocarbon-containing feed. Similar to the diluent, if steam is fed into the conversion zone, the steam can be fed into the conversion zone as a component of the hydrocarbon-containing feed or via one or more separate inlets dedicated to introducing the steam into the conversion zone.

In some embodiments, the hydrocarbon-containing feed can include sulfur. For example, the hydrocarbon-containing feed can include sulfur in a range from 0.5 ppm, 1 ppm, 5 ppm, 10 ppm, 20 ppm 30 ppm, 40 ppm, 50 ppm, 60 ppm, 70 ppm, or 80 ppm to 100 ppm, 150 ppm, 200 ppm, 300 ppm, 400 ppm, or 500 ppm. In other embodiments, the hydrocarbon-containing feed can include sulfur in a range from 1 ppm to 10 ppm, 10 ppm to 20 ppm, 20 ppm to 50 ppm, 50 ppm to 100 ppm, or 100 ppm to 500 ppm. The sulfur, if present in the hydrocarbon-containing feed, can be or can include, but is not limited to, $H_2S$, dimethyl disulfide, as one or more mercaptans, or any mixture thereof. In some embodiments, the sulfur can be introduced into the conversion zone as a separate feed, as a component of the diluent if used, and/or as a component of the steam if used.

The hydrocarbon-containing feed can be substantially free or free of molecular oxygen. In some embodiments, the hydrocarbon-containing feed can include ≤5 mol %, ≤3 mol %, or ≤1 mol % of molecular oxygen ($O_2$). It is believed that providing a hydrocarbon-containing feed substantially-free of molecular oxygen substantially prevents oxidative coupling reactions that would otherwise consume at least a portion of the alkane and/or the alkyl aromatic hydrocarbon in the hydrocarbon-containing feed.

Recovery and Use of the Upgraded Hydrocarbons

The upgraded hydrocarbon can include at least one upgraded hydrocarbon, e.g., an olefin, water, unreacted hydrocarbons, unreacted molecular hydrogen, etc. The upgraded hydrocarbon can be recovered or otherwise obtained via any convenient process, e.g., by one or more conventional processes. One such process can include cooling the effluent to condense at least a portion of any water and any heavy hydrocarbon that may be present, leaving the olefin and any unreacted alkane or alkyl aromatic primarily in the vapor phase. Olefin and unreacted alkane or alkyl aromatic hydrocarbons can then be removed from the reaction product in one or more separator drums. For example, one or more splitters can be used to separate the dehydrogenated product from the unreacted hydrocarbon-containing feed.

In some embodiments, a recovered olefin, e.g., propylene, can be used for producing polymer, e.g., recovered propylene can be polymerized to produce polymer having segments or units derived from the recovered propylene such as polypropylene, ethylene-propylene copolymer, etc. Recovered isobutene can be used, e.g., for producing one or more of: an oxygenate such as methyl tert-butyl ether, fuel additives such as diisobutene, synthetic elastomeric polymer such as butyl rubber, etc.

EXEMPLARY EMBODIMENTS

FIG. 1 depicts an illustrative system for upgrading a hydrocarbon-containing feed in line 111 that includes a first reactor or first conversion zone 101, a second reactor or second conversion zone 103, a regenerator or combustion zone 105, and an optional reduction reactor or reduction zone 107, according to one or more embodiments. The system can also include a gas-solid separator or separation zone 108 and a catalyst splitter or catalyst splitter zone 109. While the first conversion zone 101 and the second conversion zone 103 are shown as separate conversion zones, the first and second conversion zones 101, 103 can be disposed within a single reactor, e.g., a riser reactor or a downer reactor. The hydrocarbon-containing feed via line 111 can be introduced into the first conversion zone 101. In some embodiments, the hydrocarbon-containing feed via line 111 can be introduced into a bottom end of a riser reactor or a top end of a downer reactor. In some embodiments, a co-reactant, e.g., steam ($H_2O$), and/or diluent gas via line 113 can be mixed with the hydrocarbon-containing feed in line 111. The hydrocarbon-containing feed and optional co-reactant and/or diluent gas can be mixed or otherwise contacted with a stream of recycled catalyst particles introduced via line 110 into the first conversion zone 101. The recycled catalyst particles can have a lower temperature than the regenerated and reduced catalyst particles in line 139 that can be introduced into the second conversion zone 103. As the hydrocarbon-containing feed reacts in the presence of the recycled catalyst particles and moves through the first conversion zone 101, additional hydrocarbon-containing feed and/or additional co-reactant and/or diluent gas can optionally be introduced into the first conversion zone 101. The first conversion zone effluent via line 115 coming out of the first conversion zone 101 can include coked catalyst particles and a gaseous stream rich in the one or more upgraded hydrocarbons, unreacted hydrocarbons, molecular hydrogen, and any other gaseous components. In some embodiments, for propane dehydrogenation, the temperature of first conversion zone effluent in line 115 can be <620° C., <610° C., <600° C., <590° C., <580° C. or <570° C.

The first conversion zone effluent via line 115 and the regenerated and reduced catalyst particles via line 139 can be introduced into the second conversion zone 103. The regenerated and reduced catalyst particles in line 139, when introduced into the second conversion zone 103 can have a higher temperature than the coked catalyst particles in the first conversion zone effluent in line 115. In some embodiments, an amount of the hydrocarbon-containing feed has been converted to the upgraded hydrocarbon in line 115, thermal cracking of the unconverted hydrocarbon-containing feed can be reduced while increasing the temperature within the second conversion zone. The second conversion zone effluent in line 117 can include coked catalyst particles and a gaseous stream rich in the one or more upgraded hydrocarbons, unreacted hydrocarbons, molecular hydrogen, and any other gaseous components. In some embodiments, the temperature of the second conversion zone effluent in line 117 can be >620° C., >630° C., >640° C., >650° C., >660° C., >670° C. or >680° C.

In some embodiments, the first conversion zone 101 and the second conversion zone 103 can be within different parts of a riser reactor. The hydrocarbon-containing feed in line 111, the optional diluent gas 113, the recycled catalyst particles in line 110 can enter at the bottom of the riser reactor. The regenerated and reduced catalyst particles via line 139 can enter through a solid injection point at the middle part of the riser. In this embodiment, the first conversion zone 101 would be from the bottom of the riser reactor up to the solid injection point at the middle part of the riser and the second conversion zone 103 would be from the solid injection point at the middle part of the riser reactor to the top of the riser reactor.

In some embodiments, the first conversion zone 101 can be configured or adapted to produce the first conversion zone effluent in line 115 having a first temperature and the second conversion zone 103 can be configured or adapted to produce the second conversion zone effluent in line 117 having a second temperature, where the second temperature can be greater than the first temperature. In some embodiments, the temperature of the first conversion zone effluent in line 115 can be in a range from 350° C., 400° C., 500° C., or 520° C. to 600° C., 620° C., 670° C., or 700° C. and the temperature of the second conversion zone effluent in line 117 can be in a range from 400° C., 600° C., 650° C., or 660° C. to 725° C., 750° C., 800° C., or 900° C.

The gaseous components and coked catalyst particles contained in the second conversion zone effluent in line 117 can be separated via one or more gas-solid separation zones 108 to produce a first gaseous stream rich in the one or more upgraded hydrocarbons, unreacted hydrocarbons, molecular hydrogen, and any other gaseous components via line 119 and a first particle stream rich in coked catalyst particles via line 121. While such separation zone 108 is shown outside of the second conversion zone 103, the separation zone 108 can also be located inside second conversion zone 103.

The first gaseous stream via line 119 can be sent to product recovery and subjected to additional processing steps. The first particle stream via line 121 can be introduced into the catalyst splitter zone 109, and a second particle stream that can include a first portion of the first catalyst particle stream can be recycled via line 110 to the first conversion zone 101, as mentioned above. A third particle stream that can include a second portion of the coked catalyst particles via line 123 can be introduced into the combustion zone 105. The combustion zone can be disposed within a reactor where the coked catalyst particles can be contacted with an oxidant, e.g., air, introduced via line 125 to combust at least a portion of the coke disposed on the surface of the catalyst particles. In some embodiments, an optional supplemental fuel via line 127 can also be introduced into the combustion zone 105. The supplemental fuel can be combusted to produce additional heat that can further heat the regenerated catalyst particles within the combustion zone 105 to a desired temperature to support the endothermic reactions that occur within the first and second conversion zones 101, 103.

Within combustion zone 105 a gas-solid separation device can be used to separate the regenerated catalyst particles from the combustion gas to produce a second gaseous stream rich in the combustion gas via line 129 and a second particle stream rich in the regenerated catalyst particles via line 131. In some embodiments, the combustion gas in line 129, which can contain fine catalyst particulates, can be directed to a secondary separation device for recovery of the fine catalyst particulates, heat recovery, or disposal.

The regenerated catalyst particles via line 131 and an optional reducing gas via line 137 can be introduced into the optional reduction zone 107. The regenerated catalyst particles can be contacted with the reducing gas within the reduction zone 107 to produce regenerated and reduced catalyst particles. Within the reduction zone 107, a gas-solid separation device can be used to separate the regenerated and reduced catalyst particles from the reducing gas to provide a third gaseous stream via line 135 and a fourth particle stream rich in the regenerated and reduced catalyst particles via line 139. The gaseous stream recovered via line 135, depending, at least in part, on its composition, can be removed from the system, or it may be supplied to the combustion zone 105 as fuel gas, or it may be carried into the second conversion zone with the regenerated and reduced catalyst particles without being separated from regenerated and reduced catalyst particles. In some embodiments, the regenerated catalyst particles contained in line 131 can be cooled before entering into reduction zone 107.

In some embodiments, one or more intermediate conversion zones can be located between the first conversion zone 101 and the second conversion zone 103. The regenerated and reduced catalyst in line 139 can be split into multiple streams of a same flow rate or different flow rates and enter into the one or more intermediate conversion zone. The multiple streams of regenerated and reduced catalyst particles can also be individually cooled/heated before entering into the intermediate conversion zones. In some embodiments, the regenerated and reduced catalyst particles introduced into the second conversion zone 103, when one or more intermediate conversion zones are present can be further heated or can be directly introduced into the second conversion zone 103, with the regenerated and reduced catalyst being cooled prior to introduction into the one or more intermediate conversion zones. Optionally, multiple combustion zones 105 and multiple optional reduction zones 107, operating at different temperatures can be used to create catalyst streams having different temperatures. The catalyst streams of different temperatures can be fed into different reaction zones so that the temperature of the flow exiting each reaction zone increases along the direction of the flow to create a temperature gradient along a length of the riser or downer reactor. The catalyst particles in lines 121, 110, 123, 125, and 129 can be pneumatically moved through the reaction system via a carrier fluid or transport fluid. In some embodiments, the carrier fluid can be or can include steam.

Figure 2:
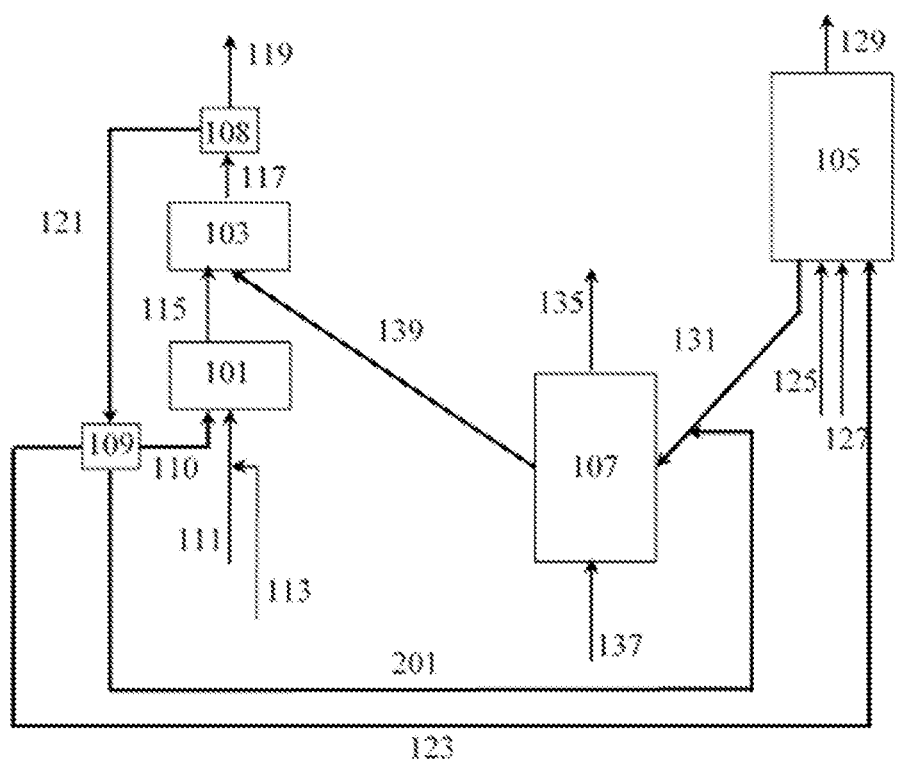
FIG. 2 depicts another illustrative system for upgrading a hydrocarbon-containing feed that is similar to the system shown in FIG. 1, but further includes an additional coked catalyst transfer line, according to one or more embodiments described.

FIG. 2 depicts another illustrative system for upgrading the hydrocarbon-containing feed in line 111 that is similar to the system shown in FIG. 1, but further includes an additional coked catalyst transfer line 201, according to one or more embodiments. In some embodiments, the coked catalyst particles can be further separated within the catalyst splitter zone 109 into an additional coked catalyst particle stream via line 201. As shown, the additional coked catalyst particle stream via line 201 can be mixed with the regenerated catalyst particles in line 131 and introduced into the reduction zone 107. By mixing a portion of the coked catalyst particles with the regenerated catalyst particles in line 131, the temperature of particle stream introduced into the reduction zone 107 can be reduced before introduction into the optional reduction zone 107. If the optional reduction zone 107 is not present, the mixture of the coked catalyst particles and regenerated catalyst particles can be introduced into the second conversion zone 103.

EXAMPLES

The foregoing discussion can be further described with reference to the following non-limiting examples.

Examples 1-3

Laboratory experiments were performed to demonstrate the benefits of a two conversion zone reactor. Fixed bed experiments were conducted at ~100 kPa-absolute, with a hydrocarbon-containing feed consisting of 81 mol % of propane, 9 mol % of Ar and 10 mol % of water.

A gas chromatograph (GC) was used to measure the composition of the reactor effluents. The concentration of each component in the reactor effluents were then used to calculate the $C_3H_6$ yield and selectivity. The $C_3H_6$ yield and selectivity, as reported in these examples, was calculated on the carbon mole basis.

In each example, a certain amount of the catalyst $M_{cat}$ was mixed with an appropriate amount of quartz/SiC diluent and loaded into a quartz reactor. The amount of diluent was determined so that the catalyst bed (catalyst+diluent) overlaps with the isothermal zone of the quartz reactor and the catalyst bed is largely isothermal during operation. The dead volume of the reactor was filled with quartz chips/rods.

The catalyst used in Examples 1-7 was prepared according to the following procedure: Set aside 2.3 g PURALOX® MG 80/150 (Sasol), which was a MgO—$Al_2O_3$ mixed metal oxide with 80 wt % MgO and 20 wt % $Al_2O_3$. Mixed 0.103 g of tin (IV) chloride pentahydrate (Acros Organics), 0.0184 g of chloroplatinic acid hexahydrate (BioXtra), and 1.725 ml of water in a small glass vial to make a solution. The PURALOX® MG 80/150 was impregnated with the solution, the impregnated PURALOX® MG was dried at 110° C. for 6 hours, and calcined at 800° C. for 12 hours. The final product contained nominally 0.3 wt % Pt and 1.5 wt % Sn.

Example 1 consisted of a single conversion zone with experimental conditions specified in Table 1. The temperature, the weight hourly space velocity (WHSV), and homogeneous gas phase residence time were 670° C., 4.7 h$^{-1}$, and 3.4 s, respectively. The WHSV was defined by the mass flow rate of $C_3H_8$ in the feed divided by the mass of the catalyst $M_{cat}$ within the reactor. The homogeneous gas phase residence time was calculated by dividing the volumetric feed flow rate at the experimental temperature and pressure by the void space in the isothermal zone.

Examples 2 and 3 represent the first conversion zone and the second conversion zone of a two-zone reactor connected in series. The catalyst loading and reactor packing of the two zones were identical. The temperature of the first conversion zone and the second conversion zone were 580° C. and 670° C., respectively. The combined WHSV of the two conversion zone reactor was 4.7 h$^{-1}$, which was identical to the single-zone reactor of Example 1. The combined homogeneous gas phase residence time of the two conversion zone reactor was 3.4-3.7 s, depending on whether 580° C. or 670° C. was used for calculation.

TABLE 1

| Example | Feed Flow Rate (ml/min RT, 100 kPa-absolute) | Mcat (g) | T (° C.) | WHSV (h$^{-1}$) | Gas phase RT (s) |
|---|---|---|---|---|---|
| 1 | 4.8 | 0.1 | 670 | 4.7 | 3.4 |
| 2 + 3 | 9.6 | 0.1 + 0.1 | 580 + 670 | 4.7 | 3.4-3.7 |

The $C_3H_6$ yield and $C_3H_6$ selectivity values of the effluent coming out of the single conversion zone reactor (Example 1), the first zone of the two conversion zone reactor (Example 2), and the second zone of the two conversion zone reactor (Example 2+3) are shown in Table 2 below.

TABLE 2

| Example | $C_3H_6$, Yld. (%) | $C_3H_6$, Sel. (%) | $C_3H_8$, conversion |
|---|---|---|---|
| 1 | 51.3 | 86.7 | 59.2 |
| 2 | 35.8 | 98.7 | 36.3 |
| 2+3 | 56.8 | 92.1 | 61.7 |

By comparing Example 1 and Example 2+3, it can be seen that the two conversion zone reactor increased the $C_3H_6$ yield and the $C_3H_6$ selectivity by ~5.5% and ~5.4%, respectively. The effluent from the first zone of the two conversion zone reactor (Example 2) was a partially dehydrogenated mixture with minimal selectivity loss to by-products.

Examples 4-6

Examples 4-6 were similar to Examples 1-3 except that the homogeneous gas phase residence time was reduced (See Table 3) and the mass of the catalyst used in the conversion zones was doubled.

TABLE 3

| Example | Feed Flow Rate (ml/min RT, 100 kPa-absolute) | Mcat (g) | T (° C.) | WHSV (h$^{-1}$) | Gas phase RT (s) |
|---|---|---|---|---|---|
| 4 | 9.6 | 0.2 | 670 | 4.7 | 1.7 |
| 5 + 6 | 19.2 | 0.2 + 0.2 | 580 + 670 | 4.7 | 1.7-1.9 |

The $C_3H_6$ yield and $C_3H_6$ selectivity values of the effluent coming out of the single conversion zone reactor (Example 4), the first zone of the two conversion zone reactor (Example 5), and the second zone of the two conversion zone reactor (Example 5+6) are shown in Table 4 below.

TABLE 4

| Example | $C_3H_6$, Yld. (%) | $C_3H_6$, Sel. (%) | $C_3H_8$, conversion |
|---|---|---|---|
| 4 | 62.2 | 90.5 | 68.7 |
| 5 | 39.1 | 98.8 | 39.6 |
| 5 + 6 | 64.8 | 94.7 | 68.4 |

By comparing Example 4 and Example 5+6, it can be seen that the two conversion zone reactor increased the $C_3H_6$ yield and $C_3H_6$ selectivity by ~2.6% and ~4.2%, respectively.

Examples 7-9

Examples 7-9 are similar to Examples 1-3 except the WHSV was reduced and the mass of the catalyst used in the conversion zones was doubled (See Table 5).

TABLE 5

| Example | Feed Flow Rate (ml/min RT, 100 kPa-absolute) | Mcat (g) | T (° C.) | WHSV (h$^{-1}$) | Gas phase RT (s) |
|---|---|---|---|---|---|
| 7 | 4.8 | 0.2 | 670 | 2.4 | 3.4 |
| 8 + 9 | 9.6 | 0.2 + 0.2 | 580 + 670 | 2.4 | 3.4-3.7 |

The $C_3H_6$ yield and $C_3H_6$ selectivity values of the effluent coming out of the single conversion zone reactor (Example 7), the first zone of the two conversion zone reactor (Example 8), and the second zone of the two conversion zone reactor (Example 8+9) are shown in Table 6 below.

TABLE 6

| Example | $C_3H_6$, Yld. (%) | $C_3H_6$, (Sel. (%) | $C_3H_8$, conversion |
|---|---|---|---|
| 7 | 61.8 | 87.1 | 71 |
| 8 | 40.1 | 99.1 | 40.5 |
| 8 + 9 | 66.1 | 91.7 | 72.1 |

Comparing example 7 and example 8+9 shows that the two-zone reactor concept increased the $C_3H_6$ yield and $C_3H_6$ selectivity by ~4.3% and ~4.6%, respectively.

Example 8. In a prophetic example, engineering calculations are performed to determine a feasible set of reaction conditions for the dehydrogenation of propane to propylene using the embodiment shown in FIG. 1. In this example, the conversion zones (101) and (103) are adiabatic. The hydrocarbon-containing feed is a mixture of 90 mol % of propane and 10 mol % of water at 570° C., with a total flow rate of 137 tonnes/hr. The pressure at the exit of the second conversion zone (103) is 124 kPa-absolute. The temperature at the exit of first conversion zone (101) is 620° C. and the conversion of propane is 55.0%. The temperature at the exit of the second conversion zone (103) is 670° C. and the total conversion of propane is 69.8%. Table 7 shows one set of catalyst flow rates and temperatures that achieves these zone temperatures and propane conversions. It should be noted that for the calculations in this example, the yield of coke is ignored and all of the non-selective reactions are assumed to occur in the first reaction zone. It is not expected these assumptions have a significant effect on the overall heat balance and the demonstration of a feasible example.

catalyst bed was largely isothermal during operation. The dead volume of the reactor was filled with quartz chips/rods.

TABLE 7

| Stream Number | 110 | 111 + 113 | 115 | 117 | 119 | 121 | 123 | 139 |
|---|---|---|---|---|---|---|---|---|
| Temperature, ° C. | 670 | 570 | 620 | 670 | 670 | 670 | 670 | 800 |
| Mass flow rate, T/hr | 4,000 | 143 | 4,143 | 7,143 | 143 | 6,000 | 2,000 | 2,000 |
| Solid particles | 4,000 | | 4,000 | 6,000 | | 6,000 | 2,000 | 2,000 |
| Propane | | 137 | 61.5 | 41.5 | 41.5 | | | |
| Propene | | | 59.3 | 78.4 | 78.4 | | | |
| Hydrogen | | | 2.8 | 4.2 | 4.2 | | | |
| Methane + Ethene | | | 13.7 | 13.7 | 13.7 | | | |
| Steam | | 6.2 | 6.2 | 6.2 | 6.2 | | | |

Example 9—Catalyst Compositions 2-15

Catalyst Compositions 2-15 were prepared according to the following procedure. For each catalyst composition PURALOX® MG 80/150 (3 grams) (Sasol), which was a mixed Mg/Al metal oxide that contained 80 wt % of MgO and 20 wt % of $Al_2O_3$ and had a surface area of 150 $m^2/g$, was calcined under air at 550° C. for 3 hours to form a support. Solutions that contained a proper amount of tin (IV) chloride pentahydrate when used to make the catalyst composition (Acros Organics) and/or chloroplatinic acid when used to make the catalyst composition (Sigma Aldrich), and 1.8 ml of deionized water were prepared in small glass vials. The calcined PURALOX® MG 80/150 supports (2.3 grams) for each catalyst composition were impregnated with the corresponding solution. The impregnated materials were allowed to equilibrate in a closed container at room temperature (RT) for 24 hours, dried at 110° C. for 6 hours, and calcined at 800° C. for 12 hours.

Table 8 shows the nominal Pt and Sn content of each catalyst composition based on the weight of the support.

TABLE 8

| Catalyst | Pt (wt %) | Sn (wt %) |
|---|---|---|
| 2 | 0.4 | 1 |
| 3 | 0.3 | 1 |
| 4 | 0.2 | 1 |
| 5 | 0.1 | 1 |
| 6 | 0.05 | 1 |
| 7 | 0.025 | 1 |
| 8 | 0.0125 | 1 |
| 9 | 0 | 1 |
| 10 | 0.1 | 0.5 |
| 11 | 0.1 | 1 |
| 12 | 0.1 | 2 |
| 13 | 0.0125 | 0 |
| 14 | 0.0125 | 0.5 |
| 15 | 0.0125 | 2 |

Examples using the Catalyst Compositions of Examples 2-15

Fixed bed experiments were conducted at approximately 100 kPa-absolute that used catalysts 2-9. A gas chromatograph (GC) was used to measure the composition of the reactor effluents. The concentrations of each component in the reactor effluents were then used to calculate the $C_3H_6$ yield and selectivity. The $C_3H_6$ yield and selectivity, as reported in these examples, were calculated on the carbon mole basis.

In each example, 0.3 g of the catalyst composition was mixed with an appropriate amount of quartz diluent and loaded into a quartz reactor. The amount of diluent was determined so that the catalyst bed (catalyst+diluent) overlapped with the isothermal zone of the quartz reactor and the The $C_3H_6$ yield and the selectivity at the beginning of $t_{rxn}$ and at the end of $t_{rxn}$ is denoted as $Y_{ini}$, $Y_{end}$, $S_{ini}$, and $S_{end}$, respectively, and reported as percentages in Tables 5 and 6 below for catalysts 7-14.

The process steps for catalysts 2-9 were as follows: 1. The system was flushed with an inert gas. 2. Dry air at a flow rate of 83.9 sccm was passed through a by-pass of the reaction zone, while an inert was passed through the reaction zone. The reaction zone was heated to a regeneration temperature of 800° C. 3. Dry air at a flow rate of 83.9 sccm was then passed through the reaction zone for 10 min to regenerate the catalyst. 4. The system was flushed with an inert gas. 5. A $H_2$ containing gas with 10 vol % $H_2$ and 90 vol % Ar at a flow rate of 46.6 sccm was passed through the by-pass of the reaction zone for a certain period of time, while an inert gas was passed through the reaction zone. This is then followed by flowing the $H_2$ containing gas through the reaction zone at 800° C. for 3 seconds. 6. The system was flushed with an inert gas. During this process, the temperature of the reaction zone was changed from 800° C. to a reaction temperature of 670° C. 7. A hydrocarbon-containing (HCgas) feed that included 81 vol % of $C_3H_8$, 9 vol % of inert gas (Ar or Kr) and 10 vol % of steam at a flow rate of 35.2 sccm was passed through the by-pass of the reaction zone for a certain period of time, while an inert gas was passed through the reaction zone. The hydrocarbon-containing feed was then passed through the reaction zone at 670° C. for 10 min GC sampling of the reaction effluent started as soon as the feed was switched from the by-pass of the reaction zone to the reaction zone.

The above process steps were repeated in cycles until stable performance was obtained. Tables 9 and 10 show that Catalyst 7 that contained only 0.025 wt % of Pt and 1 wt % of Sn had both a similar yield and a similar selectivity as compared to Catalyst 2 that contained 0.4 wt % of Pt and 1 wt % of Sn, which was surprising and unexpected. Catalyst 9 that did not include any Pt did not show an appreciable propylene yield.

TABLE 9

| | | Catalyst 2 | Catalyst 3 | Catalyst 4 | Catalyst 5 |
|---|---|---|---|---|---|
| Performance | $Y_{ini}$ | 61.7 | 61.7 | 60.7 | 63.7 |
| | $Y_{end}$ | 55.2 | 55.7 | 54.2 | 56.7 |
| | $S_{ini}$ | 97.3 | 97.2 | 97.0 | 97.1 |
| | $S_{end}$ | 98.1 | 98.0 | 97.7 | 98.3 |

TABLE 10

|  |  | Catalyst 6 | Catalyst 7 | Catalyst 8 | Catalyst 9 |
|---|---|---|---|---|---|
| Performance | $Y_{ini}$ | 62.4 | 62.0 | 56.7 | 2.0 |
|  | $Y_{end}$ | 57.2 | 54.6 | 45.7 | 1.7 |
|  | $S_{ini}$ | 96.7 | 97.3 | 96.9 | 64.2 |
|  | $S_{end}$ | 97.7 | 98.0 | 97.6 | 49.5 |

Catalyst compositions 10-15 were also tested using the same process steps 1-7 described above with regard to catalysts 2-9. Table 11 shows that the level of Sn should not be too low or too high for optimal propylene yield for the catalyst compositions that included 0.1 wt % of Pt based on the weight of the support.

TABLE 11

|  |  | Catalyst 10<br>0.5 wt % Sn | Catalyst 5<br>1 wt % Sn | Catalyst 11<br>1 wt % Sn | Catalyst 12<br>2 wt % Sn |
|---|---|---|---|---|---|
| Performance | $Y_{ini}$ | 58.4 | 63.7 | 63.4 | 56.5 |
|  | $Y_{end}$ | 49.5 | 56.7 | 55.5 | 47.7 |
|  | $S_{ini}$ | 96.9 | 97.1 | 97.2 | 97.8 |
|  | $S_{end}$ | 97.6 | 98.3 | 98.1 | 98.2 |

Table 12 shows that the level of Sn should not be too high or too low for optimal propylene yield for the catalyst compositions that included 0.0125 wt % of Pt based on the weight of the support.

TABLE 12

|  |  | Catalyst 13<br>0 wt % Sn | Catalyst 14<br>0.5 wt % Sn | Catalyst 8<br>1 wt % Sn | Catalyst 15<br>2 wt % Sn |
|---|---|---|---|---|---|
| Performance | $Y_{ini}$ | 2.6 | 44 | 56.7 | 55.4 |
|  | $Y_{end}$ | 1.7 | 24.4 | 45.7 | 44.1 |
|  | $S_{ini}$ | 63.9 | 96.7 | 96.9 | 96.8 |
|  | $S_{end}$ | 61.1 | 95.6 | 97.6 | 97.6 |

Figure 3:
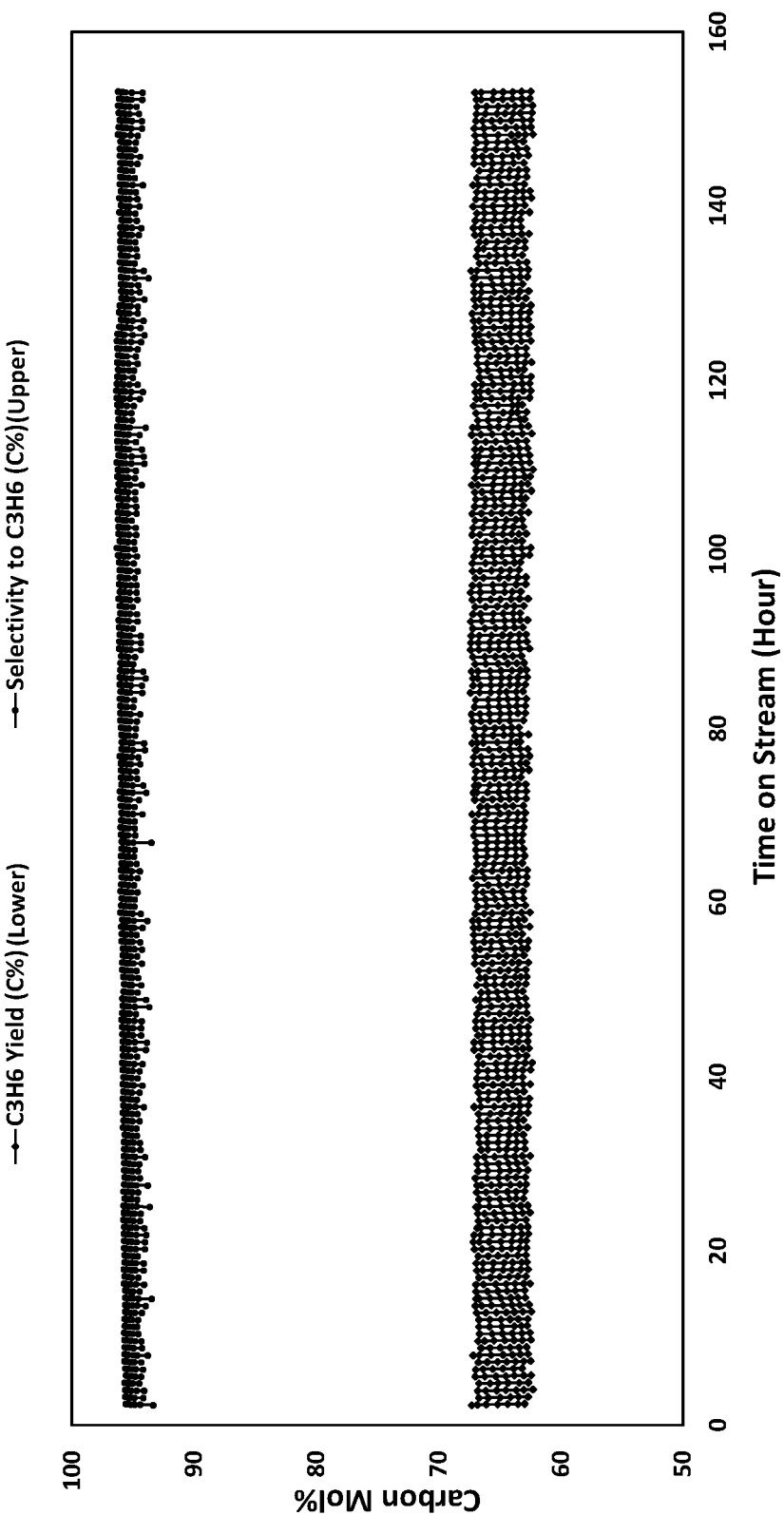
FIG. 3 shows a catalyst composition (catalyst 7) maintained its performance for 204 cycles.

Catalyst composition 7 that contained only 0.025 wt % of Pt and 1 wt % of Sn was also subjected to a longevity test using the same process steps 1-7 described above with regard to catalysts 2-9, except a flow rate of 17.6 sccm was used instead of 35.2 sccm in step 7. FIG. 3 shows that catalyst composition 7 maintained performance for 204 cycles (x-axis is time, y-axis is $C_3H_6$ yield and selectivity to $C_3H_6$, both in carbon mole %).

This disclosure can further include one or more of the following aspects and/or embodiments:

E1. A multi-stage hydrocarbon upgrading process, comprising: (I) contacting a hydrocarbon-containing feed with a first catalyst comprising a Group 8-10 element disposed on a support within a first conversion zone to effect one or more of dehydrogenation, dehydroaromatization, and dehydrocyclization of a portion of the hydrocarbon-containing feed to produce a first conversion zone effluent comprising one or more upgraded hydrocarbons, molecular hydrogen, and unconverted hydrocarbon-containing feed; (II) contacting the first conversion zone effluent with a second catalyst comprising a Group 8-10 element disposed on a support within a second conversion zone to effect one or more of dehydrogenation, dehydroaromatization, and dehydrocyclization of at least a portion of the unconverted hydrocarbon-containing feed to produce a second conversion zone effluent comprising an additional quantity of one or more upgraded hydrocarbons and molecular hydrogen; wherein: the hydrocarbon-containing feed comprises one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof; the hydrocarbon-containing feed and the first catalyst are contacted for a time period in a range from 0.1 seconds to 3 hours, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatic hydrocarbons in the hydrocarbon-containing feed; the first conversion zone effluent and the second catalyst are contacted for a time period in a range from 0.1 seconds to 3 hours, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatic hydrocarbons in the first conversion zone effluent; the first conversion zone effluent has a temperature in a range from 300° C. to 850° C.; the second conversion zone effluent has a temperature in a range from 350° C. to 900° C.; the temperature of the second conversion zone effluent is greater than the temperature of the first conversion zone effluent; the first catalyst and the second catalyst have the same composition or a different composition; the first catalyst and the second catalyst each comprise from 0.001 wt % to 6 wt % of the Group 8-10 element based on the weight of the support; the support comprises: at least one of: w wt % of one or more Group 2 elements, x wt % of one or more Group 4 elements, y wt % of one or more Group 12 elements, and z wt % of one or more elements having an atomic number of 21, 39, or 57-71, based on the weight of the support, wherein w, x, y, and z are independently in a range from 0 to 100, and wherein w+x+y+z is ≤100, wherein: any Group 2 element present is associated with a wt % m based on the weight of the support, any Group 4 element present is associated with a wt % n based on the weight of the support, any group 12 element present is associated with a wt % p based on the weight of the support, and any element having an atomic number of 21, 39, or 57-71 present is associated with a wt % q based on the weight of the support, m, n, p, and q are each equal to 1, 2, 15, or 30, or m=1, n=1, p=15, and q=1, and a sum of w/m+x/n+y/p+z/q is ≥1, based on the weight of the support; and the one or more upgraded hydrocarbons comprise a dehydrogenated hydrocarbon, a dehydroaromatized hydrocarbon, a dehydrocyclized hydrocarbon, or a mixture thereof.

E2. The process of E1, wherein at least one of the first catalyst and the second catalyst is disposed within a fixed bed.

E3. The process of E1 or E2, wherein the first conversion zone and the second conversion zone are disposed within a fixed-bed reactor.

E4. The process of E1 or E2, wherein the first conversion zone and the second conversion zone are disposed within a reverse-flow reactor.

E5. The process of E1 or E2, wherein at least one of the first catalyst and the second catalyst is in the form of fluidized catalyst particles.

E6. The process of E1, wherein first catalyst and the second catalyst are in the form of fluidized catalyst particles.

E7. The process of E6, wherein the first and second conversion zones are substantially adiabatic.

E8. The process of E6 or E7, wherein a ratio of the first catalyst to a combined amount of any $C_2$-$C_{16}$ alkanes and any $C_8$-$C_{16}$ alkyl aromatics in the hydrocarbon-containing feed within the first conversion zone is in a range of 1 to 100 on a weight to weight basis.

E9. The process of any of E6 to E8, wherein a ratio of the second catalyst to a combined amount of any $C_2$-$C_{16}$ alkanes and any $C_8$-$C_{16}$ alkyl aromatics in the first conversion zone effluent within the second conversion zone is in a range of 1 to 50 on a weight to weight basis.

E10. The process of any of E6 to E9, wherein a ratio of a combined amount of the first catalyst and the second catalyst to a combined amount of any $C_2$-$C_{16}$ alkanes and any $C_8$-$C_{16}$ alkyl aromatics in the first conversion zone effluent within the second conversion zone is in a range of 2 to 150.

E11. The process of any of E6 to E10, wherein, when the first catalyst is initially contacted with the hydrocarbon-containing feed, the first catalyst has a temperature that is in a range of from 10° C. to 200° C. greater than a temperature of the first conversion zone effluent.

E12. The process of any of E6 to E11, wherein, when the second catalyst is initially contacted with the first conversion zone effluent, the second catalyst has a temperature that is in a range of 30° C. to 300° C. greater than a temperature of the second conversion zone effluent.

E13. The process of any of E6 to E12, wherein the first conversion zone and the second conversion zone are disposed within a riser reactor or a downer reactor.

E14. The process of any of E6 to E12, wherein the first conversion zone is disposed within a first vortex reactor and the second conversion zone is disposed within a second vortex reactor.

E15. The process of any of E1 to E14, further comprising, after step (I) and before step (II), the following step: (Ia) contacting the first conversion zone effluent with one or more intermediate catalysts comprising a Group 8-10 element disposed on a support within one or more intermediate conversion zones to effect one or more of dehydrogenation, dehydroaromatization, and dehydrocyclization of a portion of the unconverted hydrocarbon-containing feed in the first conversion zone effluent to produce one or more coked intermediate catalysts and one or more intermediate conversion zone effluents having one or more intermediate temperatures comprising unconverted hydrocarbon-containing feed and an additional quantity of one or more upgraded hydrocarbons and molecular hydrogen, wherein a last intermediate conversion zone effluent is contacted with the second catalyst in the second conversion zone in step (II).

E16. The process of E15, wherein the one or more intermediate temperatures of the one or more intermediate conversion zone effluents are greater than the temperature of the first conversion zone effluent, and wherein the temperature of the second conversion zone effluent is greater than the one or more intermediate temperatures of the one or more intermediate conversion zone effluents.

E17. The process of E15, wherein the one or more intermediate catalysts are disposed within one or more fixed beds.

E18. The process of E15, wherein the one or more intermediate conversion zones are disposed within one or more fixed-bed reactors.

E19. The process of E15, wherein the one or more intermediate conversion zones are disposed within a reverse flow reactor.

E20. The process of E15, wherein the one or more intermediate catalysts are in the form of fluidized catalyst particles.

E21. The process of E20, wherein the one or more intermediate conversion zones are substantially adiabatic.

E22. The process of E20 or E21, wherein a ratio of each of the one or more intermediate catalysts to a combined amount of any $C_2$-$C_{16}$ alkanes and any $C_8$-$C_{16}$ alkyl aromatics within each of the one or more intermediate conversion zones is in a range of 1 to 50 on a weight to weight basis.

E23. The process of any of E20 to E22, wherein a ratio of a combined amount of the first catalyst, the one or more intermediate catalysts, and the second catalyst to a combined amount of any $C_2$-$C_{16}$ alkanes and any $C_8$-$C_{16}$ alkyl aromatics in the last intermediate conversion zone effluent within the second conversion zone is in a range of 3 to 300.

E24. The process of any of E20 to E23, wherein, when each of the one or more intermediate catalysts is initially contacted with the first conversion zone effluent or a preceding intermediate conversion zone effluent, each of the one or more intermediate catalysts has a temperature that is in a range of 30° C. to 300° C. greater than a temperature of the first conversion zone effluent or the preceding intermediate conversion zone effluent.

E25. The process of any of E20 to E23, wherein, when the second catalyst is initially contacted with the last intermediate conversion zone effluent, the second catalyst has a temperature that is in a range of 30° C. to 300° C. greater than a temperature of the second conversion zone effluent.

E26. The process of any of E20 to E25, wherein the one or more intermediate conversion zones are disposed within a riser reactor or a downer reactor.

E27. The process of any of E20 to E25, wherein the one or more intermediate conversion zones are disposed within one or more intermediate vortex reactors.

E28. The process of any of E1 to E27, wherein contacting the hydrocarbon-containing feed with the first catalyst produces a coked first catalyst and contacting the first conversion zone effluent with the second catalyst produces a coked second catalyst, the process further comprising: (III) contacting the coked first catalyst, the coked second catalyst, or the coked first catalyst and the coked second catalyst with an oxidant to effect combustion of at least a portion of the coke to produce a combustion gas and a regenerated first catalyst, a regenerated second catalyst, or a regenerated first catalyst and a regenerated second catalyst.

E29. The process of E28, wherein in step (III), the coked first catalyst particles, the coked second catalyst particles, or the coked first catalyst particles and the coked second catalyst particles and oxidant are contacted at a temperature in a range from 580° C. to 1,100° C., preferably from 650° C. to 1,000° C., more preferably from 700° C. to 900° C., or more preferably from 750° C. to 850° C.

E30. The process of E28 or E29, wherein in step (III), the coked first catalyst particles, the coked second catalyst particles, or the coked first catalyst particles and the coked second catalyst particles and oxidant are contacted under an oxidant partial pressure in a range from 5 kPa-absolute to 1,000 kPa-absolute, preferably from 10 kPa-absolute to 500 kPa-absolute, or more preferably from 20 kPa-absolute to 200 kPa-absolute.

E31. The process of any of E28 to 30, further comprising (IV) contacting at least a portion of any regenerated first catalyst, at least a portion of any regenerated second catalyst, or at least a portion of any regenerated first catalyst and at least a portion of any regenerated second catalyst with a reducing gas to produce a regenerated and reduced first catalyst, a regenerated and reduced second catalyst, or a regenerated and reduced first catalyst and a regenerated and reduced second catalyst.

E32. The process of E31, wherein the reducing gas comprises molecular hydrogen, carbon monoxide, methane, ethane, ethylene, propane, propylene, steam, molecular nitrogen, argon, carbon dioxide, or a mixture thereof.

E33. The process of any of E28 to E32, wherein the coked first catalyst and the coked second catalyst each comprise agglomerated Group 8-10 element disposed on the support, and wherein at least a portion of the Group 8-10 element agglomerated on the support is re-dispersed about the support during combustion of the coke in step (III).

E34. The process of any of E31 to E33, wherein in step (IV), the at least a portion of any regenerated first catalyst, the at least a portion of any regenerated second catalyst, or the at least a portion of any regenerated first catalyst and the at least a portion of any regenerated second catalyst and reducing gas are contacted at a temperature in a range from 450° C. to 900° C., preferably 600° C. to 900° C., more preferably 620° C. to 900° C., more preferably 650° C. to 850° C., or more preferably from 670° C. to 800° C.

E35. The process of any of E31 to E34, wherein in step (IV), the at least a portion of any regenerated first catalyst, the at least a portion of any regenerated second catalyst, or the at least a portion of any regenerated first catalyst and the at least a portion of any regenerated second catalyst and reducing gas are contacted under a reducing gas partial pressure in a range from 0.01 kPa-absolute to 1,000 kPa-absolute, preferably from 0.1 kPa-absolute to 500 kPa-absolute, or more preferably from 0.5 kPa-absolute to 300 kPa-absolute, or more preferably from 1 kPa-absolute to 200 kPa-absolute.

E36. The process of any of E1 to E35, wherein in step (I), the hydrocarbon-containing feed and the first catalyst are contacted in the presence of steam at an amount from 0.1 vol % to 50 vol %, preferably from 0.5 vol % to 30 vol %, or more preferably from 1 vol % to 15 vol %, based on a total volume of any $C_2$-$C_{16}$ alkanes, any $C_4$-$C_{16}$ cyclic alkanes, and any $C_8$-$C_{16}$ alkyl aromatics in the hydrocarbon-containing feed.

E37. The process of any of E1 to E36, wherein in step (II), the first conversion zone effluent and the second catalyst are contacted in the presence of steam at an amount from 0.1 vol % to 50 vol %, preferably from 0.5 vol % to 30 vol %, or more preferably from 1 vol % to 15 vol %, based on a total volume of any $C_2$-$C_{16}$ alkanes, any $C_4$-$C_{16}$ cyclic alkanes, and any $C_8$-$C_{16}$ alkyl aromatics in the first conversion zone effluent.

E38. The process of any of E1 to E37, wherein the temperature of the first conversion zone effluent is in a range from 350° C. to 700° C., preferably from 400° C. to 670° C., more preferably from 500° C. to 620° C., or more preferably from 520° C. to 600° C.

E39. The process of any of E1 to E38, wherein in step (I), the hydrocarbon-containing feed and the first catalyst are contacted under a hydrocarbon partial pressure in a range from 20 kPa-absolute to 1,000 kPa-absolute, preferably from 50 kPa-absolute to 500 kPa-absolute, or more preferably 70 kPa-absolute to 300 kPa-absolute.

E40. The process of any of E1 to E39, wherein the temperature of the second conversion zone effluent is in a range from 400° C. to 900° C., preferably from 600° C. to 800° C., more preferably from 620° C. to 750° C., or more preferably from 640° C. to 725° C.

E41. The process of any of E1 to E40, wherein in step (II), the first conversion zone effluent and the second catalyst are contacted under a hydrocarbon partial pressure in a range from 20 kPa-absolute to 1,000 kPa-absolute, preferably from 50 kPa-absolute to 500 kPa-absolute, or more preferably 70 kPa-absolute to 300 kPa-absolute.

E42. The process of any of E1 to E41, wherein at least one of the first catalyst and the second catalyst further comprise a promoter.

E43. The process of E42, wherein the promoter comprises Sn, Ga, Zn, Ge, In, Re, Ag, Au, Cu, a combination thereof, or a mixture thereof.

E44. The process of E42 or E43, wherein the promoter is disposed on the support.

E45. The process of any of E42 to E44, wherein the promoter is associated with the Group 8-10 element.

E46. The process of any of E42 to E45, wherein the promoter and the Group 8-10 element form Group 8-10 element-promoter clusters that are dispersed on the support.

E47. The process of any of E42 to E46, wherein at least one of the first catalyst and the second catalyst comprises up to 10 wt % of the promoter based on the total weight of the support.

E48. The process of any of E1 to E47, wherein at least one of the first catalyst and the second catalyst further comprise an alkali metal element disposed on the support.

E49. The process of E48, wherein the alkali metal element comprises Li, Na, K, Rb, Cs, a combination thereof, or a mixture thereof.

E50. The process of E48 or E49, wherein at least one of the first catalyst and the second catalyst comprise up to 5 wt % of the alkali metal element based on the total weight of the support.

E51. The process of any of E1 to E50, wherein m, n, p, and q are each equal to 1, 15, or 30, or wherein m=1, n=15, p=15, and q=1.

E52. The process of any of E1 to E51, wherein a molar ratio of a combined amount of any Group 2 element, any Group 4 element, any Group 12 element, and any element having an atomic number of 21, 39, or 57-71 to the Group 8-10 element in at least one of the first catalyst and the second catalyst is at least 0.18, at least 0.19, at least 0.24, or at least 0.29.

E53. The process of any of E1 to E52, wherein the support in at least one of the first catalyst and the second catalyst further comprises at least one compound comprising at least one metal element or metalloid element selected from Groups 5, 6, 7, 11, 13, 14, 15, and 16.

E54. The process of any of E1 to E53, wherein at least a portion of any Group 2 element, at least a portion of any Group 4 element, at least a portion of any Group 12 element, and at least a portion of any element having an atomic number of 21, 39, or 57-71 present in the support in at least one of the first catalyst and the second catalyst is an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide.

E55. The process of any of E1 to E54, wherein the support in at least one of the first catalyst and the second catalyst comprises one or more of the following: $Mg_uZn_{1+t}O$, where u is a positive number; $Zn_vAl2O3_{+v}$, where v is a positive number; $Mg_wAl_2O_{3+w}$, where w is a positive number; $Ca_xAl_2O_{3+x}$, where x is a positive number; $Sr_yAl_2O_{3+y}$, where y is a positive number; $Ba_zAl_2O_{3+z}$, where z is a positive number; BeO; MgO; CaO; BaO; SrO; $BeCO_3$; $MgCO_3$; $CaCO_3$; $SrCO_3$, $BaCO_3$; $ZrO_2$; ZrC; ZrN; $ZrSiO_4$; $CaZrO_3$; $Ca_7ZrAl_6O_{18}$; $TiO_2$; TiC; TiN; $TiSiO_4$; $CaTiO_3$; $Ca_7Al_6O_{18}$; $HfO_2$; HfC; HfN; $HfSiO_4$; $HfZrO_3$; $Ca_7HfAl_6O_{18}$; ZnO; $Zn_3(PO_4)_2$; $Zn(ClO_3)_2$; $ZnSO_4$; $B_2O_6Zn_3$; $Zn_3N_2$; $ZnCO_3$; $CeO_2$; $Y_2O_3$; $La_2O_3$; $Sc_2O_3$; $Pr_6O_{11}$; $CePO_4$; $CeZrO_4$; $CeAlO_3$; $BaCeO_3$; $CePO_4$; Yttria-stabilized $ZrO_2$; combinations thereof, and mixtures thereof.

E56. The process of any of E1 to E55, wherein the support in at least one of the first catalyst and the second catalyst further comprises one or more of the following: $B_2O_3$; $Al_2O_3$; $SiO_2$; SiC; $Si_3N_4$; an aluminosilicate; VO; $V_2O_3$; $VO_2$; $V_2O_5$; $Ga_2O_3$; $In_2O_3$; $Mn_2O_3$; $Mn_3O_4$; MnO; a zeolite; combinations thereof; and mixture thereof.

E57. The process of any of E1 to E56, wherein the support in at least one of the first catalyst and the second catalyst is in the form of a plurality of primary particles comprising the Group 8-10 element disposed thereon.

E58. The process of any of E1 to E57, wherein at least one of the first catalyst and the second catalyst comprises primary particles having an average cross-sectional length in a range from 0.2 nm to 500 μm, preferably from 0.5 nm to 300 μm, more preferably from 1 nm to 200 μm, more preferably from 5 nm to 100 μm, and still more preferably from 2 nm to 100 nm, as measured by a transmission electron microscope.

E59. The process of any of E1 to E58, wherein the Group 8-10 element in at least one of the first catalyst and the second catalyst is disposed on the support such that the Group 8-10 element is the active component of the catalyst particles that effects the one or more of dehydrogenation, dehydroaromatization, and dehydrocyclization in at least one of steps (I) and (II).

E60. The process of any of E1 to E59, wherein the support in at least one of the first catalyst and the second catalyst has a surface area in a range from 0.1 m²/g to 1,500 m²/g, preferably from 1 m²/g to 1,000 m²/g, more preferably from 10 m²/g to 800 m²/g, or more preferably from 100 m²/g to 500 m²/g.

E61. The process of any of E1 to E60, wherein the hydrocarbon-containing feed comprises ethane, propane, isobutane, butane, ethylbenzene, propylbenzene, methylethylbenzene, or a mixture thereof.

E62. A multi-stage hydrocarbon upgrading process, comprising: (I) contacting a hydrocarbon-containing feed with a first plurality of fluidized catalyst particles comprising a Group 8-10 element disposed on a support within a first conversion zone to effect one or more of dehydrogenation, dehydroaromatization, and dehydrocyclization of a first portion of the hydrocarbon-containing feed to produce a first conversion zone effluent comprising coked first catalyst particles, one or more upgraded hydrocarbons, molecular hydrogen, and unconverted hydrocarbon-containing feed; (II) contacting the first conversion zone effluent with a second plurality of fluidized catalyst particles comprising a Group 8-10 element disposed on a support within a second conversion zone to effect one or more of dehydrogenation, dehydroaromatization, and dehydrocyclization of at least a portion of the unconverted hydrocarbon-containing feed to produce a second conversion zone effluent comprising coked second catalyst particles, an additional quantity of upgraded hydrocarbons, and an additional quantity of molecular hydrogen, wherein: the hydrocarbon-containing feed comprises one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof; the hydrocarbon-containing feed and the first plurality of fluidized catalyst particles are contacted for a time period in a range from 0.1 seconds to 2 minutes, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatic hydrocarbons in the hydrocarbon-containing feed; the first conversion zone effluent and the second plurality of fluidized catalyst particles are contacted for a time period in a range from 0.1 seconds to 2 minutes, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatic hydrocarbons in the first conversion zone effluent; the first conversion zone effluent has a temperature in a range from 300° C. to 850° C.; the second conversion zone effluent has a temperature in a range from 350° C. to 900° C.; a temperature of the second conversion zone effluent is greater than a temperature of the first conversion zone effluent; and the one or more upgraded hydrocarbons comprise a dehydrogenated hydrocarbon, a dehydroaromatized hydrocarbon, a dehydrocyclized hydrocarbon, or a mixture thereof; (III) obtaining from the second conversion zone effluent a first gaseous stream rich in the upgraded hydrocarbons and molecular hydrogen and a first particle stream rich in the coked first catalyst particles and the coked second catalyst particles; (IV) splitting the first particle stream into a second particle stream and a third particle stream; (V) recycling the second particle stream to the first conversion zone as the first plurality of fluidized particles; (VI) contacting the third particle stream with an oxidant in a combustion zone to effect combustion of at least a portion of the coke to produce a combustion effluent comprising regenerated catalyst particles lean in coke and a combustion gas; (VII) obtaining from the combustion effluent a second gaseous stream rich in the combustion gas and a fourth particle stream rich in the regenerated catalyst particles; and (VIII) recycling the fourth particle stream to the second conversion zone as the second plurality of fluidized catalyst particles.

E63. The process of E62, further comprising, after step (VII) and before step (VIII), the following step: (VIIa) contacting at least a portion of the fourth particle stream with a reducing gas to produce regenerated and reduced catalyst particles, wherein the regenerated and reduced catalyst particles are recycled to the second conversion zone as the second plurality of fluidized catalyst particles in step (VIII).

E64. The process of E63, wherein at least a portion of the Group 8-10 element in the regenerated and reduced catalyst particles is at a lower oxidized state as compared to the Group 8-10 element in the regenerated catalyst particles.

E65. The process of E63 or E64, wherein in step (VIIa), the regenerated catalyst particles and reducing gas are contacted at a temperature in a range from 450° C. to 900° C., preferably 600° C. to 900° C., more preferably 620° C. to 900° C., more preferably 650° C. to 850° C., or more preferably from 670° C. to 800° C.

E66. The process of any of E63 to E65, wherein in step (VIIa), the regenerated catalyst particles and reducing gas are contacted under a reducing gas partial pressure in a range from 0.01 kPa-absolute to 1,000 kPa-absolute, preferably from 0.1 kPa-absolute to 500 kPa-absolute, or more preferably from 0.5 kPa-absolute to 300 kPa-absolute, or more preferably from 1 kPa-absolute to 200 kPa-absolute.

E67. The process of any of E63 to E66, wherein the reducing gas comprises molecular hydrogen, carbon monoxide, methane, ethane, ethylene, propane, propylene, steam, molecular nitrogen, argon, carbon dioxide, or a mixture thereof.

E68. The process of any of E62 to E67, wherein step (IV) further comprises separating a fifth particle stream from the first particle stream, the process further comprising contacting the fourth particle stream with the fifth particle stream to produce a combined particle stream.

E69. The process of any of E62 to E68, wherein the first and second conversion zones are substantially adiabatic.

E70. The process of any of E62 to E69, wherein a ratio of the first plurality of fluidized catalyst particles to a combined amount of any $C_2$-$C_{16}$ alkanes and any $C_8$-$C_{16}$ alkyl aromatics in the hydrocarbon-containing feed within the first conversion zone is in a range of from 1 to 100 on a weight to weight basis.

E71. The process of any of E62 to E70, wherein a ratio of the second plurality of fluidized catalyst particles to a combined amount of any $C_2$-$C_{16}$ alkanes and any $C_8$-$C_{16}$ alkyl aromatics in the first conversion zone effluent within the second conversion zone is in a range of from 1 to 50 on a weight to weight basis.

E72. The process of any of E62 to E71, wherein a ratio of a combined amount of the first plurality of fluidized catalyst particles and the second plurality of fluidized catalyst particles to a combined amount of any $C_2$-$C_{16}$ alkanes and any $C_8$-$C_{16}$ alkyl aromatics in the first conversion zone effluent within the second conversion zone is in a range of from 2 to 150.

E73. The process of any of E62 to E72, wherein, when the first plurality of fluidized catalyst particles is initially contacted with the hydrocarbon-containing feed, the first plurality of fluidized catalyst particles have a temperature that is in a range of 10° C. to 200° C. greater than a temperature of the first conversion zone effluent.

E74. The process of any of E62 to E73, wherein, when the second plurality of fluidized catalyst particles is initially contacted with the first conversion zone effluent, the second plurality of fluidized catalyst particles have a temperature that is in a range of 30° C. to 300° C. greater than a temperature of the second conversion zone effluent.

E75. The process of any of E62 to E74, further comprising, after step (I) and before step (II), the following step: (Ia) contacting the first conversion zone effluent with one or more intermediate pluralities of fluidized catalyst particles comprising a Group 8-10 element disposed on a support within one or more intermediate conversion zones to effect one or more of dehydrogenation, dehydroaromatization, and dehydrocyclization of a portion of the unconverted hydrocarbon-containing feed in the first conversion zone effluent to produce one or more coked intermediate pluralities of fluidized catalyst particles and one or more intermediate conversion zone effluents having one or more intermediate temperatures comprising unconverted hydrocarbon-containing feed and an additional quantity of one or more upgraded hydrocarbons and molecular hydrogen, wherein a last intermediate conversion zone effluent is contacted with the second catalyst in the second conversion zone in step (II).

E76. The process of E75, wherein the one or more intermediate conversion zones are disposed within one or more riser reactors or one or more downer reactors.

E77. The process of E76, wherein the one or more intermediate conversion zones are disposed within one or more intermediate vortex reactors.

E78. The process of any of E75 to E77, wherein the one or more intermediate conversion zones are substantially adiabatic.

E79. The process of any of E75 to E78, wherein a ratio of each of the one or more intermediate pluralities of fluidized catalyst particles to a combined amount of any $C_2$-$C_{16}$ alkanes and any $C_8$-$C_{16}$ alkyl aromatics within each of the one or more intermediate conversion zones is in a range of 1 to 50 on a weight to weight basis.

E80. The process of any of E75 to E79, wherein a ratio of a combined amount of the first plurality of fluidized catalyst particles, the one or more intermediate pluralities of fluidized catalyst particles, and the second plurality of fluidized catalyst particles to a combined amount of any $C_2$-$C_{16}$ alkanes and any $C_8$-$C_{16}$ alkyl aromatics in the last intermediate conversion zone effluent within the second conversion zone is in a range of 3 to 300.

E81. The process of any of E75 to E80, wherein, when each of the one or more intermediate pluralities of fluidized catalyst particles is initially contacted with the first conversion zone effluent or a preceding intermediate conversion zone effluent, each of the one or more intermediate pluralities of fluidized catalyst particles have a temperature that is in a range of 30° C. to 300° C. greater than a temperature of the first conversion zone effluent or the preceding intermediate conversion zone effluent.

E82. The process of any of E75 to E81, wherein, when the second plurality of fluidized catalyst particles is initially contacted with the last intermediate conversion zone effluent, the second plurality of fluidized catalyst particles have a temperature that is in a range of 30° C. to 300° C. greater than a temperature of the second conversion zone effluent.

E83. The process of any of E62 to E82, wherein: the first plurality of fluidized catalyst particles have a temperature greater than the temperature of the first conversion zone effluent when initially contacted with the hydrocarbon-containing feed such that the heat required to achieve the temperature within the first conversion zone is provided by the first plurality of fluidized catalyst particles, the second plurality of fluidized catalyst particles have a temperature greater than the temperature of the second conversion zone effluent when initially contacted with the first conversion zone effluent such that the heat required to achieve the temperature within the second conversion zone is provided by the second plurality of fluidized catalyst particles.

E84. The process of any of E62 to E83, wherein the hydrocarbon-containing feed comprises ethane, propane, isobutane, butane, ethylbenzene, propylbenzene, methylethylbenzene, or a mixture thereof.

E85. The process of any of E62 to E84, wherein the hydrocarbon-containing feed and the first plurality of fluidized catalyst particles are contacted in step (I) for a time period in a range from 0.1 seconds to 1.5 minutes, preferably from of 0.5 seconds to 1 minute, or more preferably from 1 seconds to 30 seconds.

E86. The process of any of E62 to E85, wherein a weight ratio of the first plurality of fluidized catalyst particles to a combined amount of any $C_2$-$C_{16}$ alkanes and any $C_8$-$C_{16}$ aromatic hydrocarbons is in a range from 1 to 150, preferably from 5 to 100, or more preferably from 10 to 80.

E87. The process of any of E62 to E86, wherein the hydrocarbon-containing feed contacts the first plurality of fluidized catalyst particles in step (I) at a weight hourly space velocity in a range from 0.1 $hr^{-1}$ to 100 $hr^{-1}$, preferably from 0.2 $hr^{-1}$ to 64 $hr^{-1}$, or more preferably from 0.4 $hr^{-1}$ to 32 $hr^{-1}$, based on the weight of any $C_2$-$C_{16}$ alkanes and any $C_8$-$C_{16}$ aromatic hydrocarbons in the hydrocarbon-containing feed.

E88. The process of any of E62 to E87, wherein the temperature of the first conversion zone effluent is in a range from 350° C. to 700° C., preferably from 400° C. to 670° C., more preferably from 500° C. to 620° C., or more preferably from 520° C. to 600° C.

E89. The process of any of E62 to E88, wherein in step (I), the hydrocarbon-containing feed and the first plurality of fluidized catalyst particles are contacted under a hydrocarbon partial pressure in a range from 20 kPa-absolute to 1,000 kPa-absolute, preferably from 50 kPa-absolute to 500 kPa-absolute, or more preferably 70 kPa-absolute to 300 kPa-absolute.

E90. The process of any of E62 to E89, wherein in step (I), the hydrocarbon-containing feed and the first plurality of fluidized catalyst particles are contacted in the presence of steam at an amount from 0.1 vol % to 50 vol %, preferably from 0.5 vol % to 30 vol %, or more preferably from 1 vol % to 15 vol %, based on a total volume of any $C_2$-$C_{16}$ alkanes, any $C_4$-$C_{16}$ cyclic alkanes, and any $C_8$-$C_{16}$ alkyl aromatics in the hydrocarbon-containing feed.

E91. The process of any of E62 to E90, wherein the first conversion zone effluent and the second plurality of fluidized catalyst particles are contacted in step (II) for a time period in a range from 0.1 seconds to 1.5 minutes, preferably from of 0.5 seconds to 1 minute, or more preferably from 1 seconds to 30 seconds.

E92. The process of any of E62 to E91, wherein a weight ratio of the second plurality of fluidized catalyst particles to a combined amount of any $C_2$-$C_{16}$ alkanes and any $C_8$-$C_{16}$ aromatic hydrocarbons is in a range from 1 to 150, preferably from 5 to 100, or more preferably from 10 to 80.

E93. The process of any of E62 to E92, wherein the first conversion zone effluent contacts the first plurality of fluidized catalyst particles in step (II) at a weight hourly space velocity in a range from 0.1 $hr^{-1}$ to 100 $hr^{-1}$, preferably from 0.2 $hr^{-1}$ to 64 $hr^{-1}$, or more preferably from 0.4 $hr^{-1}$ to 32 $hr^{-1}$, based on the weight of any $C_2$-$C_{16}$ alkanes and any $C_8$-$C_{16}$ aromatic hydrocarbons in the first conversion zone effluent.

E94. The process of any of E62 to E92, wherein the temperature of the second conversion zone effluent is in a range from 400° C. to 900° C., preferably from 600° C. to 800° C., more preferably from 650° C. to 750° C., or more preferably from 660° C. to 725° C.

E95. The process of any of E62 to E94, wherein in step (II), the first conversion zone effluent and the second plurality of fluidized catalyst particles are contacted under a hydrocarbon partial pressure in a range from 20 kPa-absolute to 1,000 kPa-absolute, preferably from 50 kPa-absolute to 500 kPa-absolute, or more preferably 70 kPa-absolute to 300 kPa-absolute.

E96. The process of any of E62 to E95, wherein in step (II), the first conversion zone effluent and the second plurality of fluidized catalyst particles are contacted in the presence of steam at an amount from 0.1 vol % to 50 vol %, preferably from 0.5 vol % to 30 vol %, or more preferably from 1 vol % to 15 vol %, based on a total volume of any $C_2$-$C_{16}$ alkanes, any $C_4$-$C_{16}$ cyclic alkanes, and any $C_8$-$C_{16}$ alkyl aromatics in the first conversion zone effluent.

E97. The process of any of E62 to E96, wherein in step (VI), the third particle stream and the oxidant are contacted at a temperature in a range from 580° C. to 1,100° C., preferably from 650° C. to 1,000° C., more preferably from 700° C. to 900° C., or more preferably from 750° C. to 850° C.

E98. The process of any of E62 to E97, wherein in step (VI), the third particle stream and the oxidant are contacted under an oxidant partial pressure in a range from 5 kPa-absolute to 1,000 kPa-absolute, preferably from 10 kPa-absolute to 500 kPa-absolute, or more preferably from 20 kPa-absolute to 100 kPa-absolute.

E99. The process of any of E62 to E98, wherein the first plurality of fluidized catalyst and the second plurality of fluidized catalyst each comprise from 0.001 wt % to 6 wt % of the Group 8-10 element based on the weight of the support; and the support comprises: at least one of: w wt % of one or more Group 2 elements, x wt % of one or more Group 4 elements, y wt % of one or more Group 12 elements, and z wt % of one or more elements having an atomic number of 21, 39, or 57-71, based on the weight of the support, wherein w, x, y, and z are independently in a range from 0 to 100, wherein w+x+y+z is ≤100, wherein: any Group 2 element present is associated with a wt % m based on the weight of the support, any Group 4 element present is associated with a wt % n based on the weight of the support, any group 12 element present is associated with a wt % p based on the weight of the support, and any element having an atomic number of 21, 39, or 57-71 present is associated with a wt % q based on the weight of the support, m, n, p, and q are each equal to 1, 15, or 30, or m=1, n=15, p=15, and q=1, and a sum of w/m+x/n+y/p+z/q is ≥1, based on the weight of the support.

E100. The process of any of E62 to E99, wherein at least one of the first plurality of fluidized catalyst particles and the second plurality of fluidized catalyst particles further comprise a promoter.

E101. The process of E100, wherein the promoter comprises Sn, Ga, Zn, Ge, In, Re, Ag, Au, Cu, a combination thereof, or a mixture thereof.

E102. The process of E100 or E101, wherein the promoter is disposed on the support.

E103. The process of any of E100 to E102, wherein the promoter is associated with the Group 8-10 element.

E104. The process of any of E100 to E103, wherein the promoter and the Group 8-10 element form Group 8-10 element-promoter clusters that are dispersed on the support.

E105. The process of any of E100 to E104, wherein at least one of the first catalyst and the second catalyst comprises up to 10 wt % of the promoter based on the total weight of the support.

E106. The process of any of E100 to E105, wherein at least one of the first plurality of fluidized catalyst particles and the second plurality of fluidized catalyst particles further comprise an alkali metal element disposed on the support.

E107. The process of E106, wherein the alkali metal element comprises Li, Na, K, Rb, Cs, a combination thereof, or a mixture thereof.

E108. The process of E106 or E107, wherein at least one of the first plurality of fluidized catalyst particles and the second plurality of fluidized catalyst particles comprise up to 5 wt % of the alkali metal element based on the total weight of the support.

E109. The process of any of E99 to E108, wherein m, n, p, and q are each equal to 1, 15, or 30, or wherein m=1, n=15, p=15, and q=1.

E110. The process of any of E99 to E109, wherein a molar ratio of a combined amount of any Group 2 element, any Group 4 element, any Group 12 element, and any element having an atomic number of 21, 39, or 57-71 to the Group 8-10 element in at least one of the first plurality of fluidized catalyst particles and the second plurality of fluidized catalyst particles is at least 0.18, at least 0.19, at least 0.24, or at least 0.29.

E111. The process of any of E99 to E110, wherein the support in at least one of the first plurality of fluidized catalyst particles and the second plurality of fluidized catalyst particles further comprises at least one compound comprising at least one metal element or metalloid element selected from Groups 5, 6, 7, 11, 13, 14, 15, and 16.

E112. The process of any of E99 to E111, wherein at least a portion of any Group 2 element, at least a portion of any Group 4 element, at least a portion of any Group 12 element, and at least a portion of any element having an atomic number of 21, 39, or 57-71 present in the support in at least one of the first plurality of fluidized catalyst particles and the second plurality of fluidized catalyst particles is an oxide, a phosphate, a halide, a halate, a sulfate, a sulfide, a borate, a nitride, a carbide, an aluminate, an aluminosilicate, a silicate, a carbonate, metaphosphate, a selenide, a tungstate, a molybdate, a chromite, a chromate, a dichromate, or a silicide.

E113. The process of any of E62 to E112, wherein the support in at least one of the first plurality of fluidized catalyst particles and the second plurality of fluidized catalyst particles comprises one or more of the following: $Mg_uZn_{1-u}O$, where u is a positive number; $Zn_vAl2O3_{+v}$, where v is a positive number; $Mg_wAl_2O_{3+w}$, where w is a positive number; $Ca_xAl_2O_{3+x}$, where x is a positive number; $Sr_yAl_2O_{3+y}$, where y is a positive number; $Ba_zAl_2O_{3+z}$, where z is a positive number; BeO; MgO; CaO; BaO; SrO; $BeCO_3$; $MgCO_3$; $CaCO_3$; $SrCO_3$, $BaCO_3$; $ZrO_2$; ZrC; ZrN; $ZrSiO_4$; $CaZrO_3$; $Ca_7ZrAl_6O_{18}$; $TiO_2$; TiC; TiN; $TiSiO_4$; $CaTiO_3$; $Ca_7Al_6O_{18}$; $HfO_2$; HfC; HfN; $HfSiO_4$; $HfZrO_3$; $Ca_7HfAl_6O_{18}$; ZnO; $Zn_3(PO_4)_2$; $Zn(ClO_3)_2$; $ZnSO_4$; $B_2O_6Zn_3$; $Zn_3N_2$; $ZnCO_3$; $CeO_2$; $Y_2O_3$; $La_2O_3$; $Sc_2O_3$; $Pr_6O_{11}$; $CePO_4$; $CeZrO_4$; $CeAlO_3$; $BaCeO_3$; $CePO_4$; Yttria-stabilized $ZrO_2$; combinations thereof, and mixtures thereof.

E114. The process of any of E62 to E113, wherein the support in at least one of the first plurality of fluidized catalyst particles and the second plurality of fluidized catalyst particles further comprises one or more of the following: $B_2O_3$; $Al_2O_3$; $SiO_2$; SiC; $Si_3N_4$; an aluminosilicate; VO; $V_2O_3$; $VO_2$; $V_2O_5$; $Ga_2O_3$; $In_2O_3$; $Mn_2O_3$; $Mn_3O_4$; MnO; a zeolite; combinations thereof; and mixture thereof.

E115. The process of any of E62 to E114, wherein the support in at least one of the first plurality of fluidized catalyst particles and the second plurality of fluidized catalyst particles is in the form of a plurality of primary particles comprising the Group 8-10 element disposed thereon.

E116. The process of any of E62 to E114, wherein at least one of the first plurality of fluidized catalyst particles and the second plurality of fluidized catalyst particles comprise primary particles having an average cross-sectional length in a range from 0.2 nm to 500 μm, preferably from 0.5 nm to 300 μm, more preferably from 1 nm to 200 μm, more preferably from 5 nm to 100 μm, and still more preferably from 2 nm to 100 nm, as measured by a transmission electron microscope.

E117. The process of any of E62 to E116, wherein the Group 8-10 element in at least one of the first plurality of fluidized catalyst particles and the second plurality of fluidized catalyst particles is disposed on the support such that the Group 8-10 element is the active component of the catalyst particles that effects the one or more of dehydrogenation, dehydroaromatization, and dehydrocyclization in at least one of steps (I) and (II).

E118. The process of any of E62 to E117, wherein the support in at least one of the first plurality of fluidized catalyst particles and the second plurality of fluidized catalyst particles has a surface area in a range from 0.1 $m^2/g$ to 1,500 $m^2/g$, preferably from 1 $m^2/g$ to 1,000 $m^2/g$, more preferably from 10 $m^2/g$ to 800 $m^2/g$, or more preferably from 100 $m^2/g$ to 500 $m^2/g$.

E119. The process of any of E62 to E118, wherein the catalyst particles have a particle density in a range from 0.5 $g/cm^3$ to 3 $g/cm^3$, 0.7 $g/cm^3$ to 2 $g/cm^3$, or 0.8 $g/cm^3$ to 1.4 $g/cm^3$.

E120. The process of any of E62 to E119, wherein the catalyst particles have a size and particle density that is consistent with a Geldart A definition.

E121. A multistage hydrocarbon upgrading system, comprising: a first conversion zone adapted for contacting a hydrocarbon-containing feed with a first plurality of fluidized catalyst particles to effect one or more of dehydrogenation, dehydroaromatization, and dehydrocyclization of a first portion of the hydrocarbon-containing feed to produce a first conversion zone effluent comprising first coked catalyst particles, one or more upgraded hydrocarbons, molecular hydrogen, and unconverted hydrocarbon-containing feed; a second conversion zone adapted for contacting the first conversion zone effluent with a second plurality of fluidized catalyst particles to effect one or more of dehydrogenation, dehydroaromatization, and dehydrocyclization of at least a portion of the unconverted hydrocarbon-containing feed to produce a second conversion zone effluent comprising second coked catalyst particles, an additional quantity of upgraded hydrocarbons, and an additional quantity of molecular hydrogen; a first separator adapted for separating the second conversion zone effluent into a first gaseous stream rich in the upgraded hydrocarbons and the molecular hydrogen and a first particle stream rich in the first coked catalyst particles and the second coked catalyst particles; a second separator adapted for separating the first particle stream into a second particle stream comprising a first portion of the first particle stream and a third particle stream comprising a second portion of the first particle stream; a first channel adapted for feeding at least a portion of the second particle stream into the first conversion zone as the first plurality of fluidized catalyst particles; a second channel adapted for feeding at least a portion of the third particle stream into a combustion zone, the combustion zone adapted for contacting the third particle stream and an oxidant to effect combustion of at least a portion of the coke to produce a combustion effluent comprising regenerated catalyst particles lean in coke and a combustion gas; a third separator adapted for separating the combustion effluent into a second gaseous stream rich in the combustion gas and a fourth particle stream rich in the regenerated catalyst particles; and a third channel adapted for feeding at least a portion of the fourth particle stream into the second conversion zone as the second plurality of fluidized catalyst particles.

E122. The system of E121, further comprising a reduction zone adapted for contacting at least a portion of the fourth particle stream with a reducing gas to produce regenerated and reduced catalyst particles, wherein at least a portion of the regenerated and reduced catalyst particles are fed via the third channel into the second conversion zone.

E123. The system of E121 or 122, wherein the first conversion zone is further adapted for producing the first conversion zone effluent having a first temperature, wherein the second conversion zone is further adapted for producing the second conversion zone effluent having a second temperature, and wherein the temperature of the second conversion zone effluent is greater than the temperature of the first conversion zone effluent.

E124. The system of any of E121 to E123, wherein the first conversion zone and the second conversion zone are disposed within a riser reactor or a downer reactor.

E125. The system of any of E121 to E124, wherein the first conversion zone is disposed within a first vortex reactor and the second conversion zone is disposed within a second vortex reactor.

E126. The system of any of E121 to E124, wherein the first conversion zone is adapted for producing the first conversion zone effluent having a first temperature, wherein the second conversion zone is adapted for producing the second conversion zone effluent having at a second temperature, and wherein the second temperature is greater than the first temperature.

E127. The system of E126, wherein the temperature of the first conversion zone effluent is in a range from 350° C. to 700° C., preferably from 400° C. to 670° C., more preferably from 500° C. to 620° C., or more preferably from 520° C. to 600° C., and wherein the temperature of the second conversion zone effluent is in a range from 400° C. to 900° C., preferably from 600° C. to 800° C., more preferably from 650° C. to 750° C., or more preferably from 660° C. to 725° C.

E128. The system of any of E121 to E125, further comprising, one or more intermediate conversion zones adapted for contacting the first conversion zone effluent with one or more intermediate pluralities of fluidized catalyst particles to effect one or more of dehydrogenation, dehydroaromatization, and dehydrocyclization of at least a portion of the unconverted hydrocarbon-containing feed to produce an intermediate conversion zone effluent comprising coked intermediate catalyst particles, an additional quantity of upgraded hydrocarbons, and an additional quantity of molecular hydrogen, wherein the second conversion zone is adapted for contacting the intermediate conversion zone effluent with the second plurality of fluidized catalyst particles.

E129. The system of E128, wherein the one or more intermediate conversion zones are adapted for producing the one or more conversion zone effluents having one or more intermediate conversion zone temperatures, wherein the one or more intermediate conversion zone temperatures is greater than the temperature of the first conversion zone effluent and less than the temperature of the second conversion zone effluent.

E130. The system of E128 or E129, wherein the first conversion zone, the one or more intermediate conversion zones, and the second conversion zone are disposed within a riser reactor or a downer reactor.

E131. The system of E128 or E129, wherein the first conversion zone is disposed within a first vortex reactor, the one or more intermediate conversion zones are disposed within one or more intermediate vortex reactors, and the second conversion zone is disposed within a second vortex reactor.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

While the foregoing is directed to embodiments of the present invention, other and further embodiments of the invention may be devised without departing from the basic scope thereof, and the scope thereof is determined by the claims that follow.

What is claimed is:

1. A multi-stage hydrocarbon upgrading process, comprising:
   (I) contacting a hydrocarbon-containing feed with a first catalyst comprising a Group 8-10 element disposed on a support within a first conversion zone to effect one or more of dehydrogenation, dehydroaromatization, and dehydrocyclization of a portion of the hydrocarbon-containing feed to produce a first conversion zone effluent comprising one or more upgraded hydrocarbons, molecular hydrogen, and unconverted hydrocarbon-containing feed;

(II) contacting the first conversion zone effluent with a second catalyst comprising a Group 8-10 element disposed on a support within a second conversion zone to effect one or more of dehydrogenation, dehydroaromatization, and dehydrocyclization of at least a portion of the unconverted hydrocarbon-containing feed to produce a second conversion zone effluent comprising an additional quantity of one or more upgraded hydrocarbons and molecular hydrogen; wherein:

the hydrocarbon-containing feed comprises one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof;

the hydrocarbon-containing feed and the first catalyst are contacted for a time period in a range from 0.1 seconds to 3 hours, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatic hydrocarbons in the hydrocarbon-containing feed;

the first conversion zone effluent and the second catalyst are contacted for a time period in a range from 0.1 seconds to 3 hours, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatic hydrocarbons in the first conversion zone effluent;

the first conversion zone effluent has a temperature in a range from 300° C. to 850° C.;

the second conversion zone effluent has a temperature in a range from 350° C. to 900° C.;

the temperature of the second conversion zone effluent is greater than the temperature of the first conversion zone effluent;

the first catalyst and the second catalyst have the same composition or a different composition;

the first catalyst and the second catalyst each comprise from 0.001 wt % to 6 wt % of the Group 8-10 element based on the weight of the support;

the one or more upgraded hydrocarbons comprise a dehydrogenated hydrocarbon, a dehydroaromatized hydrocarbon, a dehydrocyclized hydrocarbon, or a mixture thereof; and at least one of the following is met:
(a) in step (I), the hydrocarbon-containing feed and the first catalyst are contacted in the presence of steam at an amount from 0.1 vol % to 50 vol %, based on a total volume of any $C_2$-$C_{16}$ alkanes, any $C_4$-$C_{16}$ cyclic alkanes, and any $C_8$-$C_{16}$ alkyl aromatics in the hydrocarbon-containing feed; and
(b) in step (II), the first conversion zone effluent and the second catalyst are contacted in the presence of steam at an amount from 0.1 vol % to 50 vol %, based on a total volume of any $C_2$-$C_{16}$ alkanes, any $C_4$-$C_{16}$ cyclic alkanes, and any $C_8$-$C_{16}$ alkyl aromatics in the first conversion zone effluent.

2. The process of claim 1, wherein at least one of the first catalyst and the second catalyst is disposed within a fixed bed; and/or a least one of the first conversion zone and the second conversion zone is disposed within a fixed-bed reactor.

3. The process of claim 1, wherein at least one of the first catalyst and the second catalyst is in the form of fluidized catalyst particles.

4. The process of claim 1, wherein at least one of the following is met:
(i) the first catalyst and the second catalyst are in the form of fluidized catalyst particles; and
(ii) and the first and second conversion zones are substantially adiabatic.

5. The process of claim 4, wherein at least one of the following is met:
(i) a ratio of the first catalyst to a combined amount of any $C_2$-$C_{16}$ alkanes and any $C_8$-$C_{16}$ alkyl aromatics in the hydrocarbon-containing feed within the first conversion zone is in a range of 1 to 100 on a weight to weight basis;
(ii) a ratio of the second catalyst to a combined amount of any $C_2$-$C_{16}$ alkanes and any $C_8$-$C_{16}$ alkyl aromatics in the first conversion zone effluent within the second conversion zone is in a range of 1 to 50 on a weight to weight basis; and
(iii) a ratio of a combined amount of the first catalyst and the second catalyst to a combined amount of any $C_2$-$C_{16}$ alkanes and any $C_8$-$C_{16}$ alkyl aromatics in the first conversion zone effluent within the second conversion zone is in a range of 2 to 150.

6. The process of claim 4, wherein at least one of the following is met:
(i) when the first catalyst is initially contacted with the hydrocarbon-containing feed, the first catalyst has a temperature that is in a range of from 10° C. to 200° C. greater than a temperature of the first conversion zone effluent; and
(ii) when the second catalyst is initially contacted with the first conversion zone effluent, the second catalyst has a temperature that is in a range of 30° C. to 300° C. greater than a temperature of the second conversion zone effluent.

7. The process of claim 4, wherein the first conversion zone and the second conversion zone are disposed within a riser reactor or a downer reactor.

8. The process of claim 1, wherein contacting the hydrocarbon-containing feed with the first catalyst produces a coked first catalyst and contacting the first conversion zone effluent with the second catalyst produces a coked second catalyst, the process further comprising:
(III) contacting the coked first catalyst, the coked second catalyst, or the coked first catalyst and the coked second catalyst with an oxidant to effect combustion of at least a portion of the coke to produce a combustion gas and a regenerated first catalyst, a regenerated second catalyst, or a regenerated first catalyst and a regenerated second catalyst.

9. The process of claim 8, wherein in step (III), at least one of the following is met:
(i) the coked first catalyst particles, the coked second catalyst particles, or the coked first catalyst particles and the coked second catalyst particles and oxidant are contacted at a temperature in a range from 580° C. to 1,100° C.; and
(ii) the coked first catalyst particles, the coked second catalyst particles, or the coked first catalyst particles and the coked second catalyst particles and oxidant are contacted under an oxidant partial pressure in a range from 5 kPa-absolute to 1,000 kPa-absolute.

10. The process of claim 8, further comprising (IV) contacting at least a portion of any regenerated first catalyst, at least a portion of any regenerated second catalyst, or at least a portion of any regenerated first catalyst and at least a portion of any regenerated second catalyst with a reducing gas to produce a regenerated and reduced first catalyst, a regenerated and reduced second catalyst, or a regenerated and reduced first catalyst and a regenerated and reduced second catalyst.

11. The process of claim 10, wherein the reducing gas comprises molecular hydrogen, carbon monoxide, methane, ethane, ethylene, propane, propylene, steam, molecular nitrogen, argon, carbon dioxide, or a mixture thereof.

12. The process of claim 10, wherein in step (IV), at least one of the following is met:
   (i) the at least a portion of any regenerated first catalyst, the at least a portion of any regenerated second catalyst, or the at least a portion of any regenerated first catalyst and the at least a portion of any regenerated second catalyst and reducing gas are contacted at a temperature in a range from 450° C. to 900° C.; and
   (ii) the at least a portion of any regenerated first catalyst, the at least a portion of any regenerated second catalyst, or the at least a portion of any regenerated first catalyst and the at least a portion of any regenerated second catalyst and reducing gas are contacted under a reducing gas partial pressure in a range from 0.01 kPa-absolute to 1,000 kPa-absolute.

13. The process of claim 1, wherein each of the following is met:
   (a) in step (I), the hydrocarbon-containing feed and the first catalyst are contacted in the presence of steam at an amount from 0.1 vol % to 50 vol %, based on a total volume of any $C_2$-$C_{16}$ alkanes, any $C_4$-$C_{16}$ cyclic alkanes, and any $C_8$-$C_{16}$ alkyl aromatics in the hydrocarbon-containing feed; and
   (b) in step (II), the first conversion zone effluent and the second catalyst are contacted in the presence of steam at an amount from 0.1 vol % to 50 vol %, based on a total volume of any $C_2$-$C_{16}$ alkanes, any $C_4$-$C_{16}$ cyclic alkanes, and any $C_8$-$C_{16}$ alkyl aromatics in the first conversion zone effluent.

14. The process of claim 1, wherein the temperature of the first conversion zone effluent is in a range from 350° C. to 700° C.

15. The process of claim 1, wherein in step (I), the hydrocarbon-containing feed and the first catalyst are contacted under a hydrocarbon partial pressure in a range from 20 kPa-absolute to 1,000 kPa-absolute.

16. The process of claim 1, wherein the temperature of the second conversion zone effluent is in a range from 400° C. to 900° C.

17. The process of claim 1, wherein in step (11), the first conversion zone effluent and the second catalyst are contacted under a hydrocarbon partial pressure in a range from 20 kPa-absolute to 1,000 kPa-absolute.

18. The process of claim 1, wherein at least one of the first catalyst and the second catalyst further comprise a promoter.

19. The process of claim 18, wherein the promoter comprises Sn, Ga, Zn, Ge, In, Re, Ag, Au, Cu, a combination thereof, or a mixture thereof.

20. The process of claim 19, wherein at least one of the first catalyst and the second catalyst comprises up to 10 wt % of the promoter based on the total weight of the support.

21. The process of claim 1, wherein the support comprises a mixed Mg/Al metal oxide.

22. The process of claim 1, wherein at least one of the following is met:
   (a) in step (I), the hydrocarbon-containing feed and the first catalyst are contacted in the presence of steam at an amount from 0.1 vol % to 50 vol %, based on a total volume of any $C_2$-$C_{16}$ alkanes, any $C_4$-$C_{16}$ cyclic alkanes, and any $C_8$-$C_{16}$ alkyl aromatics in the hydrocarbon-containing feed; and
   (b) in step (II), the first conversion zone effluent and the second catalyst are contacted in the presence of steam at an amount from 0.1 vol % to 50 vol %, based on a total volume of any $C_2$-$C_{16}$ alkanes, any $C_4$-$C_{16}$ cyclic alkanes, and any $C_8$-$C_{16}$ alkyl aromatics in the first conversion zone effluent.

23. A multi-stage hydrocarbon upgrading process, comprising:
   (I) contacting a hydrocarbon-containing feed with a first catalyst comprising a Group 8-10 element disposed on a support within a first conversion zone to effect one or more of dehydrogenation, dehydroaromatization, and dehydrocyclization of a portion of the hydrocarbon-containing feed to produce a first conversion zone effluent comprising one or more upgraded hydrocarbons, molecular hydrogen, and unconverted hydrocarbon-containing feed;
   (II) contacting the first conversion zone effluent with a second catalyst comprising a Group 8-10 element disposed on a support within a second conversion zone to effect one or more of dehydrogenation, dehydroaromatization, and dehydrocyclization of at least a portion of the unconverted hydrocarbon-containing feed to produce a second conversion zone effluent comprising an additional quantity of one or more upgraded hydrocarbons and molecular hydrogen; wherein:
   the hydrocarbon-containing feed comprises one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof;
   the hydrocarbon-containing feed and the first catalyst are contacted for a time period in a range from 0.1 seconds to 3 hours, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatic hydrocarbons in the hydrocarbon-containing feed;
   the first conversion zone effluent and the second catalyst are contacted for a time period in a range from 0.1 seconds to 3 hours, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatic hydrocarbons in the first conversion zone effluent;
   the first conversion zone effluent has a temperature in a range from 300° C. to 850° C.;
   the second conversion zone effluent has a temperature in a range from 350° C. to 900° C.;
   the temperature of the second conversion zone effluent is greater than the temperature of the first conversion zone effluent;
   the first catalyst and the second catalyst have the same composition or a different composition;
   the first catalyst and the second catalyst each comprise from 0.001 wt % to 6 wt % of the Group 8-10 element based on the weight of the support;
   at least one of the first catalyst and the second catalyst comprise an alkali metal element disposed on the support; and
   the one or more upgraded hydrocarbons comprise a dehydrogenated hydrocarbon, a dehydroaromatized hydrocarbon, a dehydrocyclized hydrocarbon, or a mixture thereof.

24. The process of claim 23, wherein the alkali metal element comprises Li, Na, K, Rb, Cs, a combination thereof, or a mixture thereof.

25. The process of claim 24, wherein at least one of the first catalyst and the second catalyst comprise up to 5 wt % of the alkali metal element based on the total weight of the support.

26. A multi-stage hydrocarbon upgrading process, comprising:
(I) contacting a hydrocarbon-containing feed with a first catalyst comprising a Group 8-10 element disposed on a support within a first conversion zone to effect dehydrogenation of a portion of the hydrocarbon-containing feed to produce a first conversion zone effluent comprising one or more upgraded hydrocarbons, molecular hydrogen, and unconverted hydrocarbon-containing feed;
(II) contacting the first conversion zone effluent with a second catalyst comprising a Group 8-10 element disposed on a support within a second conversion zone to effect dehydrogenation of at least a portion of the unconverted hydrocarbon-containing feed to produce a second conversion zone effluent comprising an additional quantity of one or more upgraded hydrocarbons and molecular hydrogen; wherein:
the hydrocarbon-containing feed comprises one or more of $C_2$-$C_{16}$ linear or branched alkanes, one or more of $C_4$-$C_{16}$ cyclic alkanes, one or more of $C_8$-$C_{16}$ alkyl aromatic hydrocarbons, or a mixture thereof;
the hydrocarbon-containing feed and the first catalyst are contacted for a time period in a range from 0.1 seconds to 3 hours, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatic hydrocarbons in the hydrocarbon-containing feed;
the first conversion zone effluent and the second catalyst are contacted for a time period in a range from 0.1 seconds to 3 hours, under a hydrocarbon partial pressure of at least 20 kPa-absolute, wherein the hydrocarbon partial pressure is the total partial pressure of any $C_2$-$C_{16}$ alkanes and any $C_8$-$C_{16}$ alkyl aromatic hydrocarbons in the first conversion zone effluent;
the first conversion zone effluent has a temperature in a range from 300° C. to 850° C.;
the second conversion zone effluent has a temperature in a range from 350° C. to 900° C.;
the temperature of the second conversion zone effluent is greater than the temperature of the first conversion zone effluent;
the first catalyst and the second catalyst have the same composition or a different composition;
the first catalyst and the second catalyst each comprise from 0.001 wt % to 6 wt % of the Group 8-10 element based on the weight of the support;
the support comprises a mixed Mg/Al metal oxide; and
the one or more upgraded hydrocarbons comprise a dehydrogenated hydrocarbon.

* * * * *